(12) United States Patent
Flavell et al.

(10) Patent No.: US 10,925,953 B2
(45) Date of Patent: Feb. 23, 2021

(54) COMPOSITIONS AND METHODS FOR TREATING AN INFLAMMATORY DISEASE OR DISORDER

(71) Applicant: Yale University, New Haven, CT (US)

(72) Inventors: Richard Flavell, Guilford, CT (US); Noah Palm, New Haven, CT (US); Marcel De Zoete, New Haven, CT (US)

(73) Assignee: Yale University, New Haven, CT (US)

( * ) Notice: Subject to any disclaimer, the term of this patent is extended or adjusted under 35 U.S.C. 154(b) by 388 days.

(21) Appl. No.: 15/507,357

(22) PCT Filed: Aug. 28, 2015

(86) PCT No.: PCT/US2015/047400
§ 371 (c)(1),
(2) Date: Feb. 28, 2017

(87) PCT Pub. No.: WO2016/033439
PCT Pub. Date: Mar. 3, 2016

(65) Prior Publication Data
US 2019/0083599 A1 Mar. 21, 2019

Related U.S. Application Data

(60) Provisional application No. 62/042,878, filed on Aug. 28, 2014.

(51) Int. Cl.
*A61K 39/116* (2006.01)
*A61K 39/00* (2006.01)
(Continued)

(52) U.S. Cl.
CPC .......... *A61K 39/116* (2013.01); *A61K 9/0053* (2013.01); *A61K 39/0008* (2013.01);
(Continued)

(58) Field of Classification Search
CPC .............. A61K 39/116; A61K 39/0008; A61K 2039/55544; A61K 2039/577;
(Continued)

(56) References Cited

U.S. PATENT DOCUMENTS 5,599,795 A * 2/1997 McCann ............ A61K 31/4164
424/93.4
6,290,960 B1 * 9/2001 Kink .................... C07K 14/245
424/164.1
(Continued)

FOREIGN PATENT DOCUMENTS

| JP | H05132428 A | 5/1993 |
| KR | 20120082529 A | 7/2012 |

(Continued)

OTHER PUBLICATIONS

Nagaro et al., (Antimicrob Agents Chemother 57: 5266-5270 Epub Aug 12, 2013). (Year: 2013).*
(Continued)

*Primary Examiner* — Jana A Hines
(74) *Attorney, Agent, or Firm* — Riverside Law LLP

(57) ABSTRACT

The invention relates to compositions and methods for treating inflammatory diseases and disorders in a subject in need thereof. In certain aspects, the invention relates to immunogenic compositions (e.g., vaccines) to diminish the number or pathogenic effects of one or more bacteria associated with the development or progression of an inflammatory disease or disorder.

14 Claims, 25 Drawing Sheets
Specification includes a Sequence Listing.

(51) Int. Cl.

| | | |
|---|---|---|
| *A61P 31/04* | (2006.01) | |
| *A61P 29/00* | (2006.01) | |
| *A61K 9/00* | (2006.01) | |
| *A61K 39/39* | (2006.01) | |
| *C12Q 1/689* | (2018.01) | |

(52) U.S. Cl.
CPC .............. *A61K 39/39* (2013.01); *A61P 29/00* (2018.01); *A61P 31/04* (2018.01); *C12Q 1/689* (2013.01); *A61K 2039/55544* (2013.01); *A61K 2039/577* (2013.01); *A61K 2039/58* (2013.01)

(58) Field of Classification Search
CPC .. A61K 39/39; A61K 9/0053; A61K 2039/58; C12Q 1/689; A61P 29/00; A61P 31/04
See application file for complete search history.

(56) References Cited

U.S. PATENT DOCUMENTS

| | | | |
|---|---|---|---|
| 8,211,432 | B2 | 7/2012 | Hoeoek |
| 9,758,838 | B2 | 9/2017 | Flavell |
| 10,428,392 | B2 | 10/2019 | Flavell et al. |
| 2005/0100531 | A1 | 5/2005 | Bienenstock |
| 2006/0073161 | A1 | 4/2006 | Breton |
| 2007/0231336 | A1 | 10/2007 | Thomas |
| 2012/0027799 | A1* | 2/2012 | Sears ................ C07K 16/1203 424/246.1 |
| 2012/0238468 | A1 | 9/2012 | Tuk |
| 2012/0276132 | A1 | 11/2012 | Feng |
| 2016/0017409 | A1 | 1/2016 | Flavell |
| 2018/0030517 | A1 | 2/2018 | Flavell |
| 2020/0002751 | A1 | 1/2020 | Flavell |

FOREIGN PATENT DOCUMENTS

| | | | |
|---|---|---|---|
| WO | 2010005836 | 1/2010 | |
| WO | 2010115092 | 10/2010 | |
| WO | 2011005756 | 1/2011 | |
| WO | 2012103337 | 8/2012 | |
| WO | 2013012332 | 1/2013 | |
| WO | 2013036290 | 3/2013 | |
| WO | 2013166031 | 11/2013 | |
| WO | 2014159510 | 10/2014 | |
| WO | WO-2014159510 A1 * | 10/2014 | ....... C12Q 2563/131 |
| WO | 2016033439 | 3/2016 | |

OTHER PUBLICATIONS

Abraham and Cho, "Inflammatory Bowel Disease," 2009, New Engl. J. Med. 361:2066-2078, downloaded from nejm.org on Jan. 25, 2019.
Atarashi et al., 2011, Induction of Colonic Regulatory T Cells by Indigenous Clostridium Species. Science 331:337.
Barreto et al., "Causes of variation in BCG vaccine efficacy: Examining evidence from the BCG REVAC cluster randomized trial to explore the masking and the blocking hypotheses", Vaccine 32(30):3759-3764 (2014).
Basset, C. et al., "Are Helicobacter species and enterotoxigenic Bacteroides fragilis involved in inflammatory bowel disease?" Dig. Dis. Sci., vol. 49, No. 9, pp. 1425-1432 (2004).
Belkaid and Hand, 2014, "Role of the microbiota in immunity and inflammation," Cell 157(1):121-141.
Bemark et al., 2012, "Induction of gut IgA production through T cell-dependent and T cell-independent pathways," Ann NY Acad Sci 1247:97-116.
Ben-Amor et al., 2005, "Genetic diversity of viable, injured, and dead fecal bacteria assessed by fluorescence-activated cell sorting and 16S rRNA gene analysis.," Appl Environ Microb 71(8):4679-4689, downloaded from http://aem.asm.org on Jan. 25, 2019.
Blumberg and Powrie, (2012), Microbiota, Disease, and Back to Health: A Metastable Journey. Science translational medicine 4:137rv7. (9 pages).
Brandtzaeg, "Secretory IgA: Designed for Anti-Microbial Defense," Frontiers in Immunology, vol. 4, Jan. 1, 2013 (Jan. 1, 2013), Article 222, 17 pages.
Chow et al., 2011, Pathobionts of the Gastrointestinal Microbiota and Inflammatory Disease. Current opinion in immunology 23:473. (14 pages).
Cong et al., 2009, "A dominant, coordinated T regulatory cell-IgA response to the intestinal microbiota," P Natl Acad Sci USA 106(46):19256-19261.
Cullender et al., 2013, "Innate and adaptive immunity interact to quench microbiome flagellar motility in the gut," Cell Host Microbe 14(5):571-581.
D'Auria et al., 2013, "Active and secreted IgA-coated bacterial fractions from the human gut reveal an under-represented microbiota core," Sci Rep 3:3515, 9 pages.
Dantas et al., 2013, "Experimental Approaches for Defining Functional Roles of Microbes in the Human Gut," Annu Rev Microbial 67:459-475.
Database WPI: Week 199326, Thomson Scientific. London. GB; Accession No. AN 1993-208829, and JPH05132428A, Lion Corp., Abstract (May 28, 1993). (1 page).
DePalma et al., 'Intestinal dysbiosis and reduced immunoglobulin-coated bacteria associated with coeliac disease in children', BMC Microbiology, Biomed. Central Ltd. GB, vol. 10, No. 1, pp. 1-7 (Feb. 24, 2010).
Eckmann et al., "Opposing functions of IKKβ during acute and chronic intestinal inflammation", Proc Natl Acad Sci, vol. 105, No. 39, pp. 15058-15063 (2008).
Elinav et al., 2011, NLRP6 Inflammasome Regulates Colonic Microbial Ecology and rish for Colitis. Cell, 145(5):745-757.
Etebu et al., Antibiotics: Classification and mechanisms of action with emphasis on molecular perspectives. (International Journal of Applied Microbiology and Biotechnology Research vol. 4, pp. 90-101) (Year: 2016).
European Extended Search Report for EP18197005.4, dated Dec. 12, 2018, 14 pages.
Everard et al., 2013, Cross-talk between Akkermansia muciniphila and intestinal epithelium controls diet-induced obesity. Proceedings of the National Academy of Sciences of the United States of America 110:9066.
Extended European Search Report issued by the European Patent Office for Application No. 14774155.7, dated Aug. 3, 2016, 10 pages.
Extended European Search Report issued by the European Patent Office for Application No. 15835666.7, dated Feb. 27, 2018, 13 pages.
Extended European Search Report issued by the European Patent Office for Application No. 18197005.4, dated Dec. 12, 2018, 12 pages.
Fujihashi et al., 1996, "gamma/delta T cell-deficient mice have impaired mucosal immunoglobulin A responses," J Exp Med 183(4):1929-1935, Downloaded from jem.rupress.org on Jan. 25, 2019.
Gevers et al., 2014, "The treatment-naive microbiome in new-onset Crohn's disease," Cell Host Microbe 15(3):382-392.
Giada De Palma et al: "Intestinal dysbiosis and reduced immunoglobulin-coated bacteria associated with coeliac disease in children", BMC Microbiology, Biomed Central Ltd, GB, vol. 10, No. 1, Feb. 24, 2010 (Feb. 24, 2010), p. 63.
Hapfelmeier et al., 2010, Reversible microbial colonization of germ-free mice reveals the dynamics of IgA immune responses. Science 328:1705.
Hirota et al., 2013, "TH17 cell plasticity in Peyer's patches is responsible for; induction of T cell-dependent IgA responses," Nat Immunol 14(4):372-379.
Hooper et al., 2012, Interactions between the microbiota and the immune system. Science 336:1268.
Huttenhower and Consortium, 2012, "Structure, function and diversity of the healthy human microbiome," Nature 486:207-214.
International Search Report and Written Opinion issued by the International Searching Authority for Application No. PCT/US2014/023967, dated Jun. 9, 2014, 10 pages.

(56) References Cited

OTHER PUBLICATIONS

International Search Report and Written Opinion issued by the International Searching Authority for Application No. PCT/US2015/047400, dated Feb. 19, 2016, 11 pages.
Ivanov et al., 2009, Induction of intestinal Th17 Cells by Segmented Filamentous Bacteria. Cell 139:485.
Jason M. Shapiro et al., "Bridging the Gap Between Host Immune Response and Intestinal Dysbiosis in Inflammatory Bowel Disease: Does Immunoglobulin A Mark the Spot?", Clinical Gastroenterology and Hepatology, vol. 13, No. 5, May 1, 2015 (May 1, 2015), pp. 842-846.
Jeon et al., 2012, Probiotic Bifidobacterium breve Induces IL-10-Producing Trl Cells in the Colon. PLoS pathogens 8:e1002714. (15 pages).
Kato et al., 2014, "Gut TFH and IgA: key players for regulation of bacterial communities and immune homeostasis," Immunol Cell Biol 92:49-56.
Kawamoto et al., 2012, "The inhibitory receptor PD-1 regulates IgA selection and bacterial composition in the gut," Science 336:485-489.
Knights et al., 2013, "Advances in inflammatory bowel disease pathogenesis: linking host genetics and the microbiome," Gut 62:1505-1510.
Kriegel et al., 2011, Naturally transmitted segmented filamentous bacteria segregate with diabetes protection in nonobese diabetic mice Proceedings of the National Academy of Sciences of the United States of America 108:115488.
Kullberg et al., 1998, "Helicobacter hepaticus triggers colitis in specific-pathogen-free interleukin-10 (IL-10)-deficient mice through an IL-12- and gamma interferon-dependent mechanism," Infect Immun 66(11):5157-5166.
L A Van Der Waaij et al., 'In vivo IgA coating of anaerobic bacteria in human faeces', Gut, vol. 38, pp. 348-354 (1996).
Littman and Pamer, 2011, Role of the Commensal Microbiota in Normal and Pathogenic Host Immune Responses. Cell host & microbe 10:311. (13 pages).
Lozupone et al., 2012, Diversity, stability and resilience of the human gut microbiota. Nature 489:220. (26 pages).
Macpherson 2012, The habitat, double life, citizenship, and forgetfulness of IgA, Immunological reviews 245:132. (15 pages).
Macpherson and Uhr, 2004, Induction of Protective IgA by Intestinal Dendritic Cells Carrying Commensal Bacteria, Science 303:1662. (4 pages).
Macpherson et al., 2000, A Primitive T Cell-Independent Mechanism of Intestinal Mucosal IgA Responses to Commensal Bacteria, Science 288:2222.
Mathias and Corthesy, 2011, "N-Glycans on secretory component: mediators of the interaction between secretory IgA and gram-positive commensals sustaining intestinal homeostasis," Gut Microbes 2(5):287-293.
Maurice et al., 2013, "Xenobiotics shape the physiology and gene expression of the active human gut microbiome," Cell 152(1-2):39-50.
Mauricio Barreto et al., "Causes of variation in BCG vaccine efficacy: Examining evidence from the BCG REVAC cluster randomized trial to explore the masking and the blocking hypotheses", Vaccine, Elsevier, Amsterdam, NL, vol. 32, No. 30, May 20, 2014 (May 20, 2014), pp. 3759-3764.
Mazmanian et al., 2008, A microbial symbiosis factor prevents intestinal inflammatory disease. Nature 453:620. (6 pages).
Nadal et al., 'Shifts in clostridia, bacteroides and immunoglobulin-coating fecal bacteria associated with weight loss in obese adolescents', International Journal of Obesity, vol. 33, No. 7, pp. 758-767 (Jul. 1, 2009).
Nasser et al., "Long-Lasting Protective Antiviral Immunity Induced by Passive Immunotherapies Requires both Neutralizing and Effector Functions of the Administered Monoclonal Antibody" Journal of Virology, Oct. 2010, vol. 84 (19), p. 10169-10181.
Noah W. Palm et al: "Immunoglobulin A Coating Identifies Colitogenic Bacteria in Inflammatory Bowel Disease", Cell, vol. 158, No. 5, Aug. 28, 2014 (Aug. 28, 2014), pp. 1000-1010.
Non-Final Office Action issued by The United States Patent and Trademark Office for U.S. Appl. No. 14/775,328, dated Dec. 7, 2016, 7 pages.
Non-Final Office Action issued by the United States Patent and Trademark Office for U.S. Appl. No. 15/664,150, dated Oct. 22, 2018, 9 pages.
Pabst, 2012, New concepts in the generation and functions of IgA. Nature Reviews Immunology; 12:821. (12 pages).
Packey and Sartor, 2009, "Commensal bacteria, traditional and opportunistic pathogens, dysbiosis and bacterial killing in inflammatory bowel diseases," Curr Opin Infect Dis 22(3):292-301.
Palm et al., 'Immunoglobulin a Coating Identifies Colitogenic Bacteria in Inflammatory Bowel Disease', Cell, vol. 158, No. 5, pp. 1000-1010 (Aug. 28, 2014).
Per Brandtzaeg: "Secretory IgA: Designed for Anti-Microbial Defense", Frontiers in Immunology, vol. 4, Jan. 1, 2013 (Jan. 1, 2013) (17 pages).
Peris-Bondia et al., 2011, "The active human gut microbiota differs from the total microbiota," PLoS One 6(7):e22448, doi: 10.1371/journal.pone.0022448. Epub Jul. 28, 2011, 10 pages.
Peterson et al., 2007, IgA Response to Symbiotic Bacteria as a Mediator of Gut Homeostasis. Cell host & microbe 2:328. (12 pages).
Prindiville, Thomas P., et al., "Bacteroides fragilis Enterotoxin Gene Sequences in Patients with Inflammatory Bowel Disease", Emerging Infectious Diseases, vol. 6, No. 2, p. 171-174. Apr. 1, 2000.
Rabizadeh et al., "Enterotoxigenic Bacteroides fragilis: A Potential Instigator of Colitis", Inflamm Bowel Dis, vol. 13, No. 12, pp. 1475-1483 (2007).
Rabizadeh, S., et al., "STAT3 Is Activated Throughout the Gastrointestinal Tract in Enterotoxigenic Bacteroides Fragilis Induces Colitis", Gastroenterology, vol. 134, No. 4 p. A-651. Apr. 1, 2008.
Rhee et al., "Induction of Persistent Colitis by a Human Commensal, Enterotoxigenic Bacteroides fragilis, in Wild-Type C57BU6 Mice", Infection and Immunity, vol. 77, No. 4, pp. 1708-1718 (2009).
Round and Mazmanian, 2009, "The gut microbiota shapes intestinal immune responses during health and disease," Nat Rev Immunol 9(5):313-323.
Saleh and Elson, 2011, "Experimental inflammatory bowel disease: insights into the host-microbiota dialog.," Immunity 34(3):293-302.
Salzman et al., 2002, Analysis of 16S libraries of mouse gastrointestinal microflora reveals a large new group of mouse intestinal bacteria. Microbiology, 148(11):3651-3660.
Sansonetti, 2011, "To be or not to be a pathogen: that is the mucosally relevant question," Mucosal Immunol 4(1):8-14.
Scher et al., 2013, "Expansion of intestinal Prevotella copri correlates with enhanced susceptibility to arthritis," Elife. Nov. 5, 2013;2:e01202. doi: 10.7554/eLife.01202. (20 pages).
Sears et al., "Association of Enterotoxigenic Bacteroides fragilis Infection with Inflammatory Diarrhea", Clin Infect Des, vol. 47, No. 6, pp. 797-803 (2008).
Sears. Cynthia L., "Enterotoxigenic Bacteroides fragilis: a Rogue among Symbiotes", Clinical Microbiology Reviews, col. 22, No. 2, pp. 349-369. Apr. 1, 2009.
Shapiro et al., "Bridging the Gap Between Host Immune Response and Intestinal Dysbiosis in Inflammatory Bowel Disease: Does Immunoglobulin A Mark the Spot?" Clinical Gastroenterology and Hepatology 13(5):842-846 (2015).
Shinkura et al., 2004, "Separate domains of AID are required for somatic hypermutation and class-switch recombination," Nat Immunol 5:707-712.
Slack et al., 2012, Functional flexibility of intestinal IgA—broadening the fine line, Front. Immun. 3:100. (10 pages).
Stepankova et al., 2007, "Segmented filamentous bacteria in a defined bacterial cocktail induce intestinal inflammation in SCID mice reconstituted with CD45RBhigh CD4+ T cell," Inflamm Bowel Dis 13:1202-1211.
Strober, 2013, Impact of the gut microbiome on mucosal inflammation, Trends in immunology 34:423. (8 pages).

(56) References Cited

OTHER PUBLICATIONS

Strowig et al., 2012, Inflammasomes in health and disease. Nature 481:278-286.
Suzuki et al., 2004, Aberrant expansion of segmented filamentous bacteria in IgA-deficient gut. Proceedings of the National Academy of Sciences of the United States of America, 101:1981. (6 pages).
Takeshi Tsuruta et al., "Development of a Method for the Identification of S-IgA-Coated Bacterial Composition in Mouse and Human Feces", Bioscience Biotechnology Biochemistry., vol. 74, No. 5, May 23, 2010 (May 23, 2010), pp. 968-973.
Talham et al., 1999, Segmented Filamentous Bacteria Are Potent Stimuli of a Physiologically Normal State of the Murine Gut Mucosal Immune System. Infection and Immunity 67:1992-2000.
Tezuka et al., 2007, "Regulation of IgA production by naturally occurring TNF/iNOS-producing dendritic cells," Nature 448(156):929-933.
Toprak, N., et al., "A possible role of Bacteroides fragilis enterotoxin in the aetiology of colorectal cancer", Clinical Microbiology and Infection, vol. 12, No. 8, p. 782-786. Aug. 1, 2006.
Toprak, N., et al., "The distribution of the bft alleles among enterotoxigenic Bacteroides fragilis strains from stool specimens and extraintestinal sites", Anaerobe, vol. 12, No. 2, pp. 71-74 (2005).
Tsuruta et al., 'The amount of secreted IgA may not determine the secretory IgA coating ratio of gastrointestinal', FEMS Immunology Med. Microbiology, vol. 56, No. 2, pp. 185-189 (May 7, 2009).
Umesaki et al., 1999, Differential Roles of Segmented Filamentous Bacteria and Clostridia in Development of the Intestinal Immune System. Infection and Immunity 67:3504-3511.
Van der Waaij et al., 1994, "Direct Flow Cytometry of Anaerobic Bacteria in Human Feces." Cytometry 16:270-279.
Van Der Waaij Laurens A et al: "Immunoglobulin coating of faecal bacteria in inflammatory bowel disease", European Journal of Gastroenterology Hepatol, Lippincott Williams and Wilkins, UK, vol. 16, No. 7, Jul. 1, 2004 (Jul. 1, 2004), pp. 669-674.
Van Der Waaij, Laurens et al., 'Immunoglobulin coating of faecal bacteria in inflammatory bowel disease', European Journal of Gastroenterology & Hepatology, vol. 16, No. 7, pp. 669-674 (Jul. 2004 ).
Weiner et al., "Antibodies and cancer therapy: versatile platforms for cancer immunotherapy" Nat Rev Immunol May 2010; 10(5): 317-327.
Wirtz et al., "Mouse models of inflammatory bowel disease", Advaned Drug Delivery Reviews, vol. 59, No. 11, pp. 1073-1083 (2007).
Wu et al., 2010, Gut-Residing Segmented Filamentous Bacteria Drive Autoimmune Arthritis via T Helper 17 Cell Immunity 32:815.
Wu, S., et al., "A human colonic commensal promotes colon tumorigenesis via activation of T helper 17 T cell response", Nature Medicine, vol. 15, No. 9. p. 1016-1022. Sep. 1, 2009.
Zhang et al., 2009, Human gut microbiota in obesity and after gastric bypass. Proceedings of the National Academy of Sciences 106:2365. (6 pages).
International Search Report and Written Opinion issued by the International Searching Authority for Application No. PCT/US2019/040601, dated Oct. 8, 2019, 12 pages.

* cited by examiner

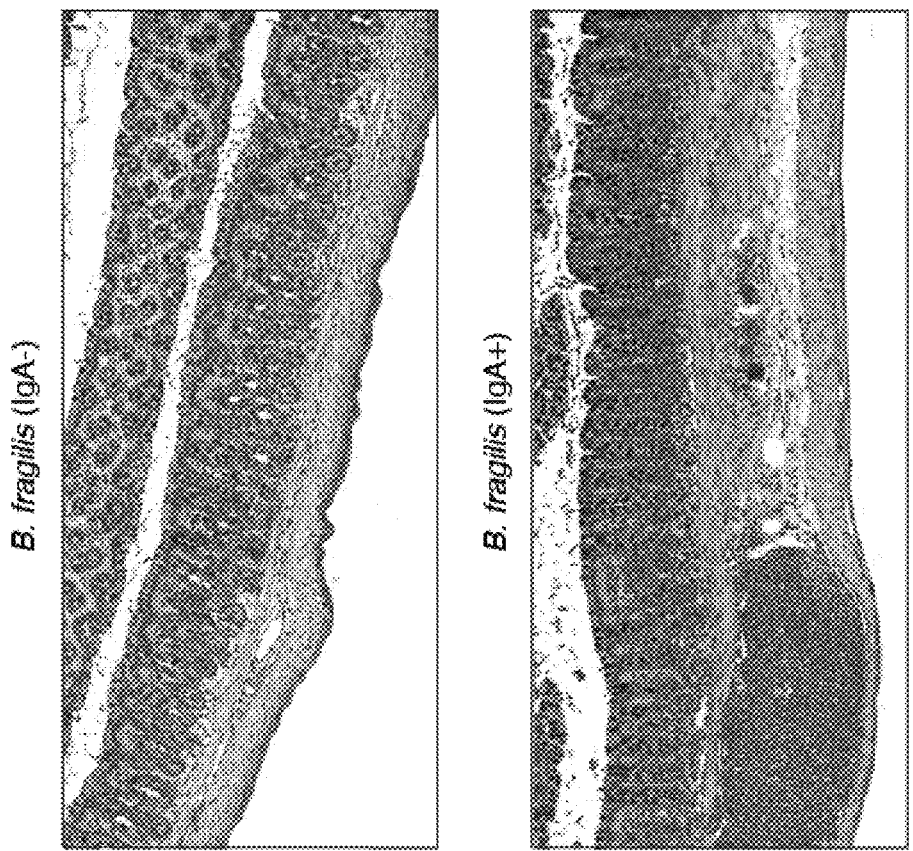
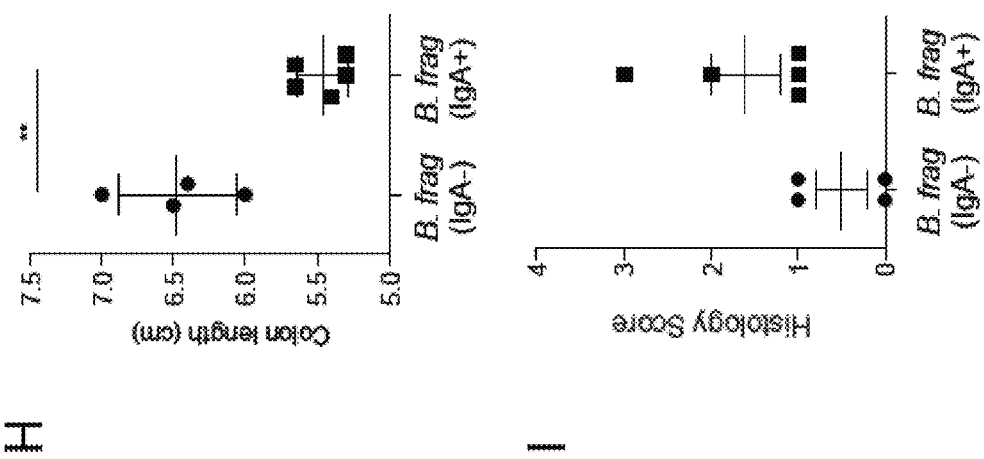
Figure 10H-10J

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 1
gctgcctccc gtaggagt                    18

COMPOSITIONS AND METHODS FOR TREATING AN INFLAMMATORY DISEASE OR DISORDER

CROSS-REFERENCE TO RELATED APPLICATIONS

This application is a U.S. national phase application filed under 35 U.S.C. § 371 claiming benefit to International Patent Application No. PCT/US2015/047400, filed Aug. 28, 2015, which is entitled to priority under 35 U.S.C. § 119(e) to U.S. Provisional Patent Application No. 62/042,878, filed Aug. 28, 2014, each of which applications is hereby incorporated herein by reference in its entirety.

STATEMENT REGARDING FEDERALLY SPONSORED RESEARCH AND DEVELOPMENT

This invention was made with government support under grant number 2T32AR007107-37 awarded by the National Institutes of Health (NIH) and grant number W81XWH-11-1-0745 awarded by the Department of Defense (DoD). The government has certain rights in the invention.

BACKGROUND OF THE INVENTION

The composition of the intestinal microbiota varies substantially between individuals and is thought to be a key determinant of host susceptibility to an increasing variety of diseases (Blumberg and Powrie, 2012, Sci Transl Med 4:137rv7; Chow et al., 2011, Curr Opin Immunol 23:473-480; Hooper et al., 2012, Science 336:1268-1273; Littman and Pamer, 2011, Cell Host Microbe 10:311-323; Lozupone et al., 2012, Nature 489:220-230). In inflammatory bowel disease (IBD), which includes Crohn's disease and ulcerative colitis, it is believed that the intestinal microbiota plays a key role in driving inflammatory responses during disease development and progression (Abraham and Cho, 2009, New Engl J Med 361: 2066-2078; Gevers et al., 2014, Cell Host Microbe 15:382-392; Knights et al., 2013, Gut 62:1505-1510). This is clearly illustrated in mouse models of IBD, where the effects of the composition of the intestinal microbiota on disease have been examined in detail (Saleh and Elson, 2011, Immunity 34:293-302). These studies have revealed that particular bacterial taxa within the intestinal microbiota can be uniquely potent drivers of intestinal disease. For example, *Prevotellaceae* species drive chronic intestinal inflammation in mice with inflammasome-mediated dysbiosis and exacerbate chemically-induced colitis (Elinav et al., 2011, Cell 145:745-757; Scher et al., 2013, eLife 2:e01202), and *Helicobacter* species can drive colitis in mice lacking the immunoregulatory cytokine interleukin-10 (Kullberg et al., 1998, Infect Immun 66:5157-5166). Thus, individual members of the intestinal microbiota vary dramatically in their propensity to induce inflammatory responses and, thereby, influence the development and progression of intestinal disease (Saleh and Elson, 2011, Immunity 34:293-302).

As in mice, specific members of the human intestinal microbiota that impact disease susceptibility and/or severity by stimulating chronic inflammatory responses may also play central roles in the etiology of IBD (Packey and Sartor, 2009, Curr Opin Infect Dis 22:292-301; Round and Mazmanian, 2009, Nat Rev Immunol 9:313-323). However, identifying such potentially disease-driving members of the intestinal microbiota in humans has remained a major challenge (Knights et al., 2013, Gut 62:1505-1510; Round et al., 2009, Nat Rev Immunol 9:313-323).

IgA is the predominant antibody isotype produced at mucosal surfaces and is a critical mediator of intestinal immunity (Pabst, 2012, Nat Rev Immunol 12:821-832; Slack et al., 2012, Front Immnol 3:100). Recognition of enteric pathogens by the intestinal immune system results in the production of high-affinity, T cell-dependent, pathogen-specific IgA, which is transcytosed into the intestinal lumen. In the lumen, these antibodies can bind and 'coat' offending pathogens, and provide protection against infection through neutralization and exclusion. Indigenous members of the intestinal microbiota also can stimulate IgA production and can become coated with IgA (Pabst, 2012, Nat Rev Immunol 12:821-832; Slack et al., 2012, Front Immnol 3:100; van der Waaij et al., 1994, Cytometry 16:270-279). However, as compared to pathogen-induced IgA, commensal-induced IgA is generally believed to be of relatively low-affinity and specificity (Pabst, 2012, Nat Rev Immunol 12:821-832; Slack et al., 2012, Front Immnol 3:100). Thus, relative levels of bacterial coating with IgA might be predicted to correlate with the magnitude of the inflammatory response triggered by a specific intestinal bacterial species.

Despite considerable effort, the identification of specific pathobionts responsible for driving the development of disease in humans has proven difficult due to the complexity and diversity of the microbiota, as well as the influence of host genetics and environment on disease susceptibility. In addition, 16S rRNA based-metagenomic studies comparing the microbiota of diseased and normal individuals does not distinguish between the distinct strains of a bacterial species, some of which may contribute to disease and some of which may not. Since different strains of the same bacterial species often colonize the same niche and share nutrient requirements, one can imagine that non-disease-driving strains might be used to replace or displace disease-driving strains of the same bacterial species. Replacement of a disease-driving bacterial strain with a non-disease-driving strain from the same bacterial species may reduce, reverse or prevent the development of disease. Thus, non-disease-driving strains identified based on low IgA coating may act as 'surgical probiotics,' which specifically target disease-driving bacteria identified based on high IgA coating that are members of the same species.

There is a need in the art to identify the specific bacteria (e.g., genus, species, strain, sub-strain, etc.) in the microbiota of a subject that can lead to the development or progression of diseases and disorders in the subject and to develop compositions and methods to reduce the pathogenic effects of such bacteria. Furthermore, there is a need in the art to identify bacteria that can specifically counteract particular disease-driving members of the microbiota. The present invention addresses this unmet need.

SUMMARY OF THE INVENTION

The invention relates to the discovery that secretory antibodies can be used to detect and identify microbes present in the microbiota of a subject that influence susceptibility to or contribute to the development or progression of diseases or disorders, including inflammatory diseases and disorders.

In one embodiment, the invention provides a method of treating or preventing an inflammatory disease or disorder associated with a secretory antibody-bound bacteria in the microbiota of a subject in need thereof. In one embodiment, the method comprises administering to the subject a vaccine to diminish the number or reduce the pathogenic effects of at least one type of bacteria associated with an inflammatory disease or disorder.

In one embodiment, the at least one type of bacteria is selected from the group consisting of *Acidaminococcus* spp., *Actinomyces* spp., *Akkermansia muciniphila*, *Allobaculum* spp., *Anaerococcus* spp., *Anaerostipes* spp., *Bacteroides* spp., *Bacteroides* Other, *Bacteroides acidifaciens*, *Bacteroides coprophilus*, *Bacteroides fragilis*, *Bacteroides ovatus*, *Bacteroides uniformis*, *Barnesiellaceae* spp., *Bifidobacterium adolescentis*, *Bifidobacterium* Other, *Bifidobacterium* spp., *Bilophila* spp., *Blautia obeum*, *Blautia producta*, *Blautia* Other, *Blautia* spp., *Bulleidia* spp., *Catenibacterium* spp., *Citrobacter* spp., *Clostridiaceae* spp., *Clostridiales* Other, *Clostridiales* spp., *Clostridium perfringens*, *Clostridium* spp., *Clostridium* Other, *Collinsella aerofaciens*, *Collinsella* spp., *Collinsella stercoris*, *Coprococcus catus*, *Coprococcus* spp., *Coriobacteriaceae* spp., *Desulfovibrionaceae* spp., *Dialister* spp., *Dorea formicigenerans*, *Dorea* spp., *Dorea* Other, *Eggerthella lenta*, *Enterobacteriaceae* Other, *Enterobacteriaceae* spp., *Enterococcus* spp., *Erysipelotrichaceae* spp., *Eubacterium biforme*, *Eubacterium biforme*, *Eubacterium dolichum*, *Eubacterium* spp., *Faecalibacterium prausnitzii*, *Fusobacterium* spp., *Gemellaceae* spp., *Haemophilus parainfluenzae*, *Haemophilus* Other, *Helicobacter* spp., *Helicobacter Lachnospiraceae* Other, *Lachnospiraceae* spp., *Lactobacillus reuteri*, *Lactobacillus mucosae*, *Lactobacillus zeae*, *Lactobacillus* spp., *Lactobacillaceae* spp., *Lactococcus* spp., *Leuconostocaceae* spp., *Megamonas* spp., *Megasphaera* spp., *Methanobrevibacter* spp., *Mitsuokella multacida*, *Mitsuokella* spp., *Mucispirillum schaedleri*, *Odoribacter* spp., *Oscillospira* spp., *Parabacteroides distasonis*, *Parabacteroides* spp., *Paraprevotella* spp., *Paraprevotellaceae* spp., *Parvimonas* spp., *Pediococcus* spp., *Pediococcus* Other, *Peptococcus* spp., *Peptoniphilus* spp., *Peptostreptococcus anaerobius*, *Peptostreptococcus* Other, *Phascolarctobacterium* spp., *Prevotella copri*, *Prevotella* spp., *Prevotella stercorea*, *Prevotellaceae*, *Proteus* spp., *Rikenellaceae* spp., *Roseburia faecis*, *Roseburia* spp., *Ruminococcaceae* Other, *Ruminococcaceae* spp., *Ruminococcus bromii*, *Ruminococcus gnavus*, *Ruminococcus* spp., *Ruminococcus* Other, *Ruminococcus torques*, *Slackia* spp., *S24-7* spp., *SMB53* spp., *Streptococcus anginosus*, *Streptococcus luteciae*, *Streptococcus* spp., *Streptococcus* Other, *Sutterella* spp., *Turicibacter* spp., UC *Bulleidia*, UC *Enterobacteriaceae*, UC *Faecalibacterium*, UC *Parabacteroides*, UC *Pediococcus*, *Varibaculum* spp., *Veillonella* spp., *Sutterella*, *Turicibacter*, UC *Clostridiales*, UC *Erysipelotrichaceae*, UC *Ruminococcaceae*, *Veillonella parvula*, *Veillonella* spp., *Veillonella dispar*, and *Weissella*.

In one embodiment, the vaccine comprises an inactivated bacterium. In one embodiment, the vaccine is administered orally to the subject. In some embodiments, the vaccine comprises at least one adjuvant and/or immunomodulator. An adjuvant and/or immunomodulator refers to a compound that enhances an immune response when administered together (or successively) with the immunological composition/vaccine. Examples of suitable adjuvants and/or immunomodulators include, but are not limited to, complete or incomplete Freund's adjuvant, RIBI (e.g., muramyl dipeptides, etc.), KLH peptide, cholera toxin or a portion thereof, *salmonella* toxin or a portion thereof, *E. coli* heat labile enterotoxin or a portion thereof, *E. coli* enterotoxin or a portion thereof, AB5 toxins or a portion thereof, mineral salts, aluminum salts (e.g., hydroxide, phosphate, Alum, etc.), calcium phosphate, liposomes, virosomes (unilamellar liposomal vehicles, immunostimulating reconstituted influenza virosomes [IRIV]), virus-like particles, cochleates, eurocine (e.g., monoglycerides with fatty acids, etc.), archaeal lipids, ISCOMS (e.g., immunostimulating complexes, structured complex of saponins and lipids, etc.), microparticles (e.g., PLG, etc.), emulsions (e.g., MF59, Montanides, etc.), monophosphoryl lipid (MPL) or synthetic derivatives, N-acetyl-muramyl-L-alanyl-D-isoglutamine (MDP) or a derivative, Detox (MPL+CWS), AS04 (Alum+MPL), AS02 (oil-in-water emulsion+MPL+QS21), AS01 (liposomes+MPL+QS21), OM-174 (e.g., Lipid A derivative, *E. coli*, etc.), OM-triacyl, oligonucleotides (e.g., CpG, etc.), double-stranded RNA (dsRNA), pathogen-associated molecular patterns (PAMPs), TLR ligands (e.g., flagellin, monophosphoryl lipid A, etc.), saponins (e.g., Quils, QS-21, etc.), chitosan, α-galactosylceramide, small-molecule immune potentiators (SMIPs) (e.g., imiquimod, resiquimod [R848], etc.), a cytokine or chemokine (e.g., IL-2, IL-12, GM-is, *Barnesiellaceae* spp., *Bifidobacterium adolescentis*, *Bifidobacterium* Other, etc.), DC Chol (e.g., lipoidal immunomodulators able to self-organize into liposomes, etc.), nanoparticle-based adjuvants, PLA (polylactic acid) microparticles, PLG (poly[lactide-co-glycolide]) microparticles, Poly(DL-lactide-co-glycolide) microparticles, polystyrene (latex) microparticles, proteosomes (e.g., hydrophobic, proteinaceous, nanoparticles comprised of purified *N. meningitidis* outer membrane proteins, etc.), and 3',5'-Cyclic diguanylic acid (c-di-GMP). Such example adjuvants and/or immunomodulators, as well as others, are understood by those skilled in the art, are readily described in available literature, and are useful in the compositions and methods of the invention.

In one aspect, the present invention provides an immunological composition for treating or preventing an inflammatory disease or disorder, comprising a vaccine to diminish the number or pathogenic effects of at least one type of bacteria associated with an inflammatory disease or disorder.

In one embodiment, the at least one type of bacteria is selected from the group consisting of *Acidaminococcus* spp., *Actinomyces* spp., *Akkermansia muciniphila*, *Allobaculum* spp., *Anaerococcus* spp., *Anaerostipes* spp., *Bacteroides* spp., *Bacteroides* Other, *Bacteroides acidifaciens*, *Bacteroides coprophilus*, *Bacteroides fragilis*, *Bacteroides ovatus*, *Bacteroides uniformis*, *Barnesiellaceae* spp., *Bifidobacterium adolescentis*, *Bifidobacterium* Other, *Bifidobacterium* spp., *Bilophila* spp., *Blautia obeum*, *Blautia producta*, *Blautia* Other, *Blautia* spp., *Bulleidia* spp., *Catenibacterium* spp., *Citrobacter* spp., *Clostridiaceae* spp., *Clostridiales* Other, *Clostridiales* spp., *Clostridium perfringens*, *Clostridium* spp., *Clostridium* Other, *Collinsella aerofaciens*, *Collinsella* spp., *Collinsella stercoris*, *Coprococcus catus*, *Coprococcus* spp., *Coriobacteriaceae* spp., *Desulfovibrionaceae* spp., *Dialister* spp., *Dorea formicigenerans*, *Dorea* spp., *Dorea* Other, *Eggerthella lenta*, *Enterobacteriaceae* Other, *Enterobacteriaceae* spp., *Enterococcus* spp., *Erysipelotrichaceae* spp., *Eubacterium biforme*, *Eubacterium biforme*, *Eubacterium dolichum*, *Eubacterium* spp., *Faecalibacterium prausnitzii*, *Fusobacterium* spp., *Gemellaceae* spp., *Haemophilus parainfluenzae*, *Haemophilus* Other, *Helicobacter* spp., *Helicobacter Lachnospiraceae* Other, *Lachnospiraceae* spp., *Lactobacillus reuteri*, *Lactobacillus mucosae*, *Lactobacillus zeae*, *Lactobacillus* spp., *Lactobacillaceae* spp., *Lactococcus* spp., *Leuconostocaceae* spp., *Megamonas* spp., *Megasphaera* spp., *Methanobrevibacter* spp., *Mitsuokella multacida*, *Mitsuokella* spp., *Mucispirillum schaedleri*, *Odoribacter* spp., *Oscillospira* spp., *Parabacteroides distasonis*, *Parabacteroides* spp., *Paraprevotella* spp., *Paraprevotellaceae* spp., *Parvimonas* spp., *Pediococcus* spp., *Pedio-

*coccus* Other, *Peptococcus* spp., *Peptoniphilus* spp., *Peptostreptococcus anaerobius*, *Peptostreptococcus* Other, *Phascolarctobacterium* spp., *Prevotella copri*, *Prevotella* spp., *Prevotella stercorea*, *Prevotellaceae*, *Proteus* spp., *Rikenellaceae* spp., *Roseburia faecis*, *Roseburia* spp., *Ruminococcaceae* Other, *Ruminococcaceae* spp., *Ruminococcus bromii*, *Ruminococcus gnavus*, *Ruminococcus* spp., *Ruminococcus* Other, *Ruminococcus torques*, *Slackia* spp., S24-7 spp., SMB53 spp., *Streptococcus anginosus*, *Streptococcus luteciae*, *Streptococcus* spp., *Streptococcus* Other, *Sutterella* spp., *Turicibacter* spp., UC *Bulleidia*, UC *Enterobacteriaceae*, UC *Faecalibacterium*, UC *Parabacteroides*, UC *Pediococcus*, *Varibaculum* spp., *Veillonella* spp., *Sutterella*, *Turicibacter*, UC *Clostridiales*, UC *Erysipelotrichaceae*, UC *Ruminococcaceae*, *Veillonella parvula*, *Veillonella* spp., *Veillonella dispar*, and *Weissella*.

In one embodiment, the vaccine comprises an inactivated bacterium. In some embodiments, the vaccine comprises at least one adjuvant and/or immunomodulator. An adjuvant and/or immunomodulator refers to a compound that enhances an immune response when administered together (or successively) with the immunological composition/vaccine. Examples of suitable adjuvants and/or immunomodulators include, but are not limited to, complete or incomplete Freund's adjuvant, RIBI (e.g., muramyl dipeptides, etc.), KLH peptide, cholera toxin or a portion thereof, *salmonella* toxin or a portion thereof, mineral salts, aluminum salts (e.g., hydroxide, phosphate, Alum, etc.), calcium phosphate, liposomes, virosomes (unilamellar liposomal vehicles, immunostimulating reconstituted influenza virosomes [IRIV]), virus-like particles, cochleates, eurocine (e.g., monoglycerides with fatty acids, etc.), archaeal lipids, ISCOMS (e.g., immunostimulating complexes, structured complex of saponins and lipids, etc.), microparticles (e.g., PLG, etc.), emulsions (e.g., MF59, Montanides, etc.), monophosphoryl lipid (MPL) or synthetic derivatives, N-acetyl-muramyl-L-alanyl-D-isoglutamine (MDP) or a derivative, Detox (MPL+CWS), AS04 (Alum+MPL), AS02 (oil-in-water emulsion+MPL+QS21), AS01 (liposomes+MPL+QS21), OM-174 (e.g., Lipid A derivative, *E. coli*, etc.), OM-triacyl, oligonucleotides (e.g., CpG, etc.), double-stranded RNA (dsRNA), pathogen-associated molecular patterns (PAMPs), *E. coli* heat labile enterotoxin, TLR ligands (e.g., flagellin, monophosphoryl lipid A, etc.), AB5 toxins or a portion thereof, saponins (e.g., Quils, QS-21, etc.), chitosan, α-galactosylceramide, small-molecule immune potentiators (SMIPs) (e.g., imiquimod, resiquimod [R848], etc.), a cytokine or chemokine (e.g., IL-2, IL-12, GM-CSF, Flt3, etc.), an accessory molecule (e.g., B7.1, etc.), liposomes (e.g., DNPC/Chol, etc.), DC Chol (e.g., lipoidal immunomodulators able to self-organize into liposomes, etc.), PLA (polylactic acid) microparticles, PLG (poly[lactide-co-glycolide]) microparticles, Poly(DL-lactide-co-glycolide) microparticles, polystyrene (latex) microparticles, proteosomes (e.g., hydrophobic, proteinaceous, nanoparticles comprised of purified *N. meningitidis* outer membrane proteins, etc.), and 3',5'-Cyclic diguanylic acid (c-di-GMP). Such example adjuvants and/or immunomodulators, as well as others, are understood by those skilled in the art, are readily described in available literature, and are useful in the compositions and methods of the invention.

In one aspect, the present invention provides a method of treating an inflammatory disease or disorder associated with a secretory antibody-bound bacteria in the microbiota of a subject in need thereof, comprising administering to the subject at least one bacterium of a species of bacteria that does not contribute to the development or progression of disease in the subject. In one embodiment, the species of bacteria that does not contribute to the development or progression of disease is a secretory antibody-bound bacteria of a subject who does not have the inflammatory disease or disorder.

In one embodiment, the invention is a method of identifying a type (e.g., genus, species, strain, sub-strain, etc.) of bacteria in the microbiota of a subject that contributes to the development or progression of an inflammatory disease or disorder in the subject, including the steps of: isolating secretory antibody-bound bacteria from the subject's biological sample, amplifying bacterial nucleic acid from secretory antibody-bound bacteria so isolated, determining the sequences of the amplicons, identifying the type (e.g., genus, species, strain, sub-strain, etc.) of antibody-bound bacteria present in the subject's biological sample by identifying nucleic acid sequences that are indicative of particular types (e.g., genus, species, strain, sub-strain, etc.) of bacteria. In some embodiments, strain and sub-strain identification is performed by at least one of anaerobic culturing of specific bacteria from feces, colonization of germ-free mice with bacterial isolates, and whole bacterial genome sequencing. In another embodiment, the invention is a method of identifying a type (e.g., genus, species, strain, sub-strain, etc.) of bacteria in the microbiota of a subject that specifically counteracts the effects of bacteria in the microbiota of a subject that contributes to the development or progression of an inflammatory disease or disorder in the subject (i.e., probiotic), including the steps of: identifying phylogenetically similar bacteria that display differential antibody coating, testing the effects of these bacteria in germ-free mice, and characterizing these bacteria genetically by whole bacterial genome sequencing. In some embodiments, the microbiota of the subject is on or near mucosal surface of the subject selected from the group consisting of the gastrointestinal tract, the respiratory tract, genitourinary tract and mammary gland. In some embodiments, the biological sample is at least one of a fecal sample, a mucus sample, a sputum sample, and a breast milk sample. In some embodiments, the bacterial nucleic acid is 16S rRNA. In some embodiments, the secretory antibody is at least one selected from the group consisting of IgA1, IgA2, and IgM. In some embodiments, the inflammatory disease or disorder is at least one inflammatory disease or disorder selected from the group consisting of inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), and non-alcoholic steatohepatitis (NASH). In some embodiments, the subject is human.

In another embodiment, the invention is a method of identifying a first strain of a species of bacteria in the microbiota of a subject, wherein the first strain of the species of bacteria does not contribute to the development or progression of disease in the subject, and wherein the species of bacteria comprises at least a second strain of bacteria, and wherein the second strain of the species of bacteria does contribute to the development or progression of the inflammatory disease or disorder, including the steps of isolating the first strain of low- or non-secretory antibody-bound bacteria from the subject's biological sample, isolating the second strain of secretory antibody-bound bacteria from the subject's biological sample, amplifying bacterial nucleic acid from the first strain of low- or non-secretory antibody-bound bacteria so isolated, amplifying bacterial nucleic acid from the second strain of secretory antibody-bound bacteria so isolated, determining the sequences of the amplicons so amplified, comparing the sequences of the amplicons so amplified from the first strain to the sequences of the amplicons so amplified from the second strain, determining that the first strain of bacteria and the second strain of bacteria are members of the same species of bacteria, determining that the first strain does not contribute to the development or progression of the inflammatory disease or disorder, and determining that the second strain does contribute to the development or progression of the inflammatory disease or disorder. In some embodiments, the method also comprises the step of culturing at least one of the first strain of bacteria and the second strain of bacteria. In some embodiments, the method also comprises the step functionally and phylogenetically characterizing at least one of the first strain of bacteria and the second strain of bacteria using at least one selected from the group consisting of colonization of germ-free mice and whole genome sequencing. In some embodiments, the microbiota of the subject is on or near mucosal surface of the subject selected from the group consisting of the gastrointestinal tract, the respiratory tract, genitourinary tract and mammary gland. In some embodiments, the biological sample is at least one of a fecal sample, a mucus sample, a sputum sample, and a breast milk sample. In some embodiments, the bacterial nucleic acid is 16S rRNA. In some embodiments, the secretory antibody is at least one selected from the group consisting of IgA1, IgA2, and IgM. In some embodiments, the inflammatory disease or disorder is at least one inflammatory disease or disorder selected from the group consisting of inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), and non-alcoholic steatohepatitis (NASH). In some embodiments, the subject is human.

In another embodiment, the invention is a method of treating an inflammatory disease or disorder of a subject in need thereof, including the step of administering to the subject at least one bacterium that is desired, preferred, neutral, beneficial, and/or under-represented in the subject's microbiota. In some embodiments, the at least one bacterium is at least one bacterium of a first strain of a species of bacteria, wherein the first strain of the species of bacteria does not contribute to the development or progression of disease in the subject, and wherein the species of bacteria comprises at least a second strain of bacteria, and wherein the second strain of the species of bacteria does contribute to the development or progression of the inflammatory disease or disorder.

In another embodiment, the invention is a method of diagnosing an inflammatory disease or disorder in a subject in need thereof by identifying a type (e.g., genus, species, strain, sub-strain, etc.) of bacteria in the microbiota of the subject that contributes to the development or progression of an inflammatory disease or disorder, including the steps of: isolating secretory antibody-bound bacteria from the subject's biological sample, amplifying bacterial nucleic acid from secretory antibody-bound bacteria so isolated, determining the sequences of the amplicons so amplified, and identifying the type (e.g., genus, species, strain, sub-strain, etc.) of antibody-bound bacteria present in the subject's biological sample by identifying nucleic acid sequences that are indicative of particular types (e.g., genus, species, strain, sub-strain, etc.) of bacteria, wherein when the type (e.g., genus, species, strain, sub-strain, etc.) of antibody-bound bacteria present in the subject's biological sample is a type (e.g., genus, species, strain, sub-strain, etc.) of bacteria that contributes to the development or progression of an inflammatory disease or disorder, the subject is diagnosed with the inflammatory disease or disorder. In some embodiments, the microbiota of the subject is on or near mucosal surface of the subject selected from the group consisting of the gastrointestinal tract, the respiratory tract, genitourinary tract and mammary gland. In some embodiments, the biological sample is at least one of a fecal sample, a mucus sample, a sputum sample, and a breast milk sample. In some embodiments, the bacterial nucleic acid is 16S rRNA. In some embodiments, the secretory antibody is at least one selected from the group consisting of IgA1, IgA2, and IgM. In some embodiments, the inflammatory disease or disorder is at least one inflammatory disease or disorder selected from the group consisting of inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), and non-alcoholic steatohepatitis (NASH). In some embodiments, the subject is human.

In one embodiment, the invention is a method of treating an inflammatory disease or disorder associated with a secretory antibody-bound bacteria in the microbiota of a subject in need thereof, the method comprising administering to the subject at least one therapy to diminish the number or pathogenic effects of at least one type and strain of bacteria that is over-represented in the microbiota of the subject. In some embodiments, the at least one therapy is at least one selected from the group consisting of at least one vaccine, at least one antibiotic, and at least one passive immunotherapy. In some embodiments, the microbiota of the subject is on or near mucosal surface of the subject selected from the group consisting of the gastrointestinal tract, the respiratory tract, genitourinary tract and mammary gland. In some embodiments, the biological sample is at least one of a fecal sample, a mucus sample, a sputum sample, and a breast milk sample. In some embodiments, the secretory antibody is at least one selected from the group consisting of IgA1, IgA2, and IgM. In some embodiments, the inflammatory disease or disorder is at least one inflammatory disease or disorder selected from the group consisting of inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), and non-alcoholic steatohepatitis (NASH). In some embodiments, the subject is human. In some embodiments, the therapy induces an immune response directed against at least one type and strain of secretory antibody-bound bacteria present in the microbiota of the subject. In some embodiments, the method further comprises administering to the subject at least one probiotic to increase the number of at least one type and strain of bacteria under-represented in the microbiota of the subject. In some embodiments, the method further comprises administering to the subject at least one 'surgical probiotic,' which is a preferred, desired or beneficial bacterial strain that belongs to the same or related species as a disease-associated strain of bacteria that was identified based on IgA coating.

In one aspect, the present invention provides a method of treating or preventing an inflammatory disease or disorder associated with a secretory antibody-bound bacteria in the microbiota of a subject in need thereof, comprising administering to the subject a composition comprising a vaccine comprising inactivated *Erysipelotrichaceae* spp. and an adjuvant. In one embodiment, the vaccine is administered orally to the subject. In one embodiment, the adjuvant is cholera toxin.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising (FIG. 1A) Overview of IgA-based cell sorting of fecal bacteria combined with 16S rRNA gene sequencing (IgA-SEQ). (FIG. 1B) Representative results and a cartoon of cell sorting of IgA+ and IgA− fecal bacteria from mice. (FIG. 1C) Heatmap depicting IgA Coating Index (ICI) scores and average relative abundance of bacterial genera in Total (Presort), IgA+ and IgA− fractions of fecal bacteria from C57Bl/6 SPF mice (n=17 samples). Relative abundance heatmaps are depicted on a logarithmic scale. Genera that are highly coated with IgA (significantly higher relative abundance in the IgA+ fraction as compared to the IgA− fraction by LEfSe; P<0.05) are marked with an asterisk. Genera with ICI>10 are labeled in red. UC, unclassified in the Greengenes reference database. Gen., classified as a distinct but unnamed genus in the Greengenes reference database. (FIG. 1D) Relative abundance of significantly coated bacterial genera in Presort, IgA+ and IgA− fractions. *P<0.05; ***P<0.001 (Wilcoxon rank-sum). Indicated are mean±standard error of the mean.

FIG. 2, comprising (FIG. 2A) Average relative abundance of bacterial genera of greater than 1% abundance in the intestinal microbiota of SPF and SPF$^{dys}$ mice. UC *Prevotellaceae* is marked with an arrow. SPF$^{dys}$ mice were co-housed with Asc$^{-/-}$ mice to allow for the acquisition of dysbiosis. (FIG. 2B) Dextran Sodium Sulfate (DSS)-induced colitis in SPF (n=5) and SPF$^{dys}$ (n=4) mice. *P<0.05; P<0.01; *P<0.001 (one-way ANOVA). (FIG. 2C) IgA coating of fecal bacteria from 10-16 week old SPF (n=8) and SPF$^{dys}$ (n=9) mice at the steady state. ***P<0.001 (unpaired Student's t-test). (FIG. 2D) Heatmap depicting IgA Coating Index (ICI) scores and average relative abundance of bacterial genera in Total (Presort), IgA+ and IgA− fractions of fecal bacteria from 10-16 week old SPF$^{dys}$ mice (n=14 samples) sampled under steady state conditions. Relative abundance heatmaps are depicted on a logarithmic scale. Genera that are highly coated with IgA (significantly higher relative abundance in the IgA+ fraction as compared to the IgA− fraction by LEfSe; P<0.05) are marked with an asterisk. Genera with ICI>10 are labeled in red. (FIG. 2E) Relative abundance of significantly coated genera in Presort, IgA+ and IgA− fractions. *P<0.05; ***P<0.001 (Wilcoxon rank-sum). Indicated are mean±standard error of the mean. UC, unclassified in the Greengenes reference database. Gen., classified as a distinct but unnamed genus in the Greengenes reference database.

FIG. 3, comprising (FIG. 3A) IgA coating of fecal bacteria from 20 healthy subjects, 27 Crohn's disease patients (CD) and 8 Ulcerative colitis patients (UC). *P<0.05; ***P<0.001 (one-way ANOVA). (FIG. 3B) Venn-diagram depicting the distribution of highly coated bacterial species in healthy, UC and CD patients. Bacterial taxa that showed an ICI score greater than 10 in at least one subject were classified as highly coated within that group. (FIG. 3C) Heatmap depicting IgA coating index (ICI) scores for bacterial species that are uniquely highly coated (ICI>10) in IBD and never highly coated or never present in healthy controls. Bars to the right of the heatmap correspond with the color-coding of the Venn-diagram in panel (3B). Each column represents an individual human subject. UC, unclassified in the Greengenes reference database. Spp., classified as a distinct but unnamed species in the Greengenes reference database.

FIG. 4, comprising (FIG. 4A) Strategy for isolation of personalized IBD-associated gut microbiota culture collections. (FIG. 4B) Selection of individual bacterial isolates comprising IgA+ and IgA− consortia and colonization of germ-free mice. Specific isolates that were included in the consortia are boxed in green (IgA−) or red (IgA+). (FIG. 4C) Barplots depicting relative abundance of bacterial taxa in IgA+ and IgA− consortia pre-gavage (D0) and in the feces of IgA+ and IgA− colonized mice 2 weeks post-colonization. All members of the pre-gavage consortia were detectable in colonized mice except *Peptinophilus* spp. in the IgA− consortium and *Streptococcus* spp. in the IgA+ consortium. UC, unclassified in the Greengenes reference database. Spp., classified as a distinct but unnamed species in the Greengenes reference database. (FIG. 4D) IgA coating of fecal bacteria from germ-free mice colonized with IgA+ (n=5) or IgA− consortia (n=5) on days 7 and 24 post-colonization. Representative plots are shown. ***P<0.005 (unpaired Student's t-test). Indicated are mean±standard error of the mean. (FIG. 4E) Microbiota localization as visualized by 16S rRNA FISH (red) and DAPI (blue) staining. The mucus layer is demarked by two dotted lines.

FIG. 5, comprising (FIG. 5A) Timeline of colonization and DSS treatment in germ-free mice colonized with IgA+ and IgA− consortia. (FIG. 5B) Colon length after DSS. *P<0.05 (unpaired Student's t-test). (FIG. 5C) Gross pathology of large bowels after DSS. Note the extensive bleeding and diarrhea in the IgA+ colonized mice. (FIG. 5D) Colon histopathology scores after DSS. Scores were assigned as follows: 0, Intact colonic architecture. No acute inflammation or epithelial injury; 1, Focal minimal acute inflammation; 2, Focal mild acute inflammation; 3, Severe acute inflammation with multiple crypt abscesses and/or focal ulceration; 4, Severe acute inflammation, multiple crypt abscesses, epithelial loss and extensive ulceration. ***P<0.0001 (unpaired Student's t-test). (FIG. 5E) Representative histology pictures from hematoxylin and eosin stained colons after DSS. Note that IgA+ colonized mice exhibit extensive inflammation, crypt abscesses, epithelial loss, and ulceration, while all IgA− colonized mice showed either no inflammation or minimal/mild focal inflammation. Data are representative of 3 independent experiments.

Figures 3A, 3B, 3C:
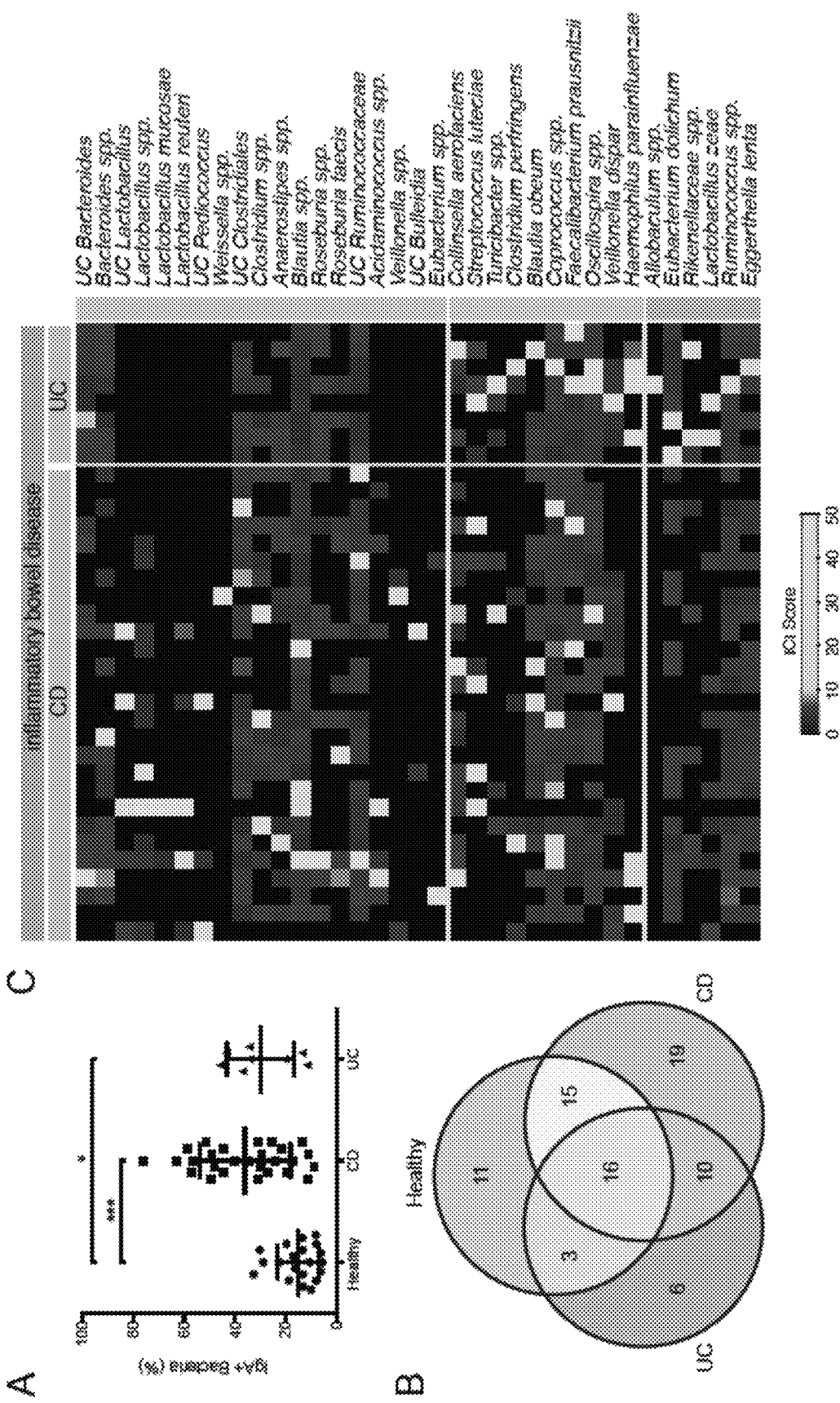
FIGS. 3A-3C, depicts the results of experiments demonstrating the IgA coating of fecal bacteria from healthy humans and inflammatory bowel disease patients.
Figures 6A, 6B, 6C, 6D:
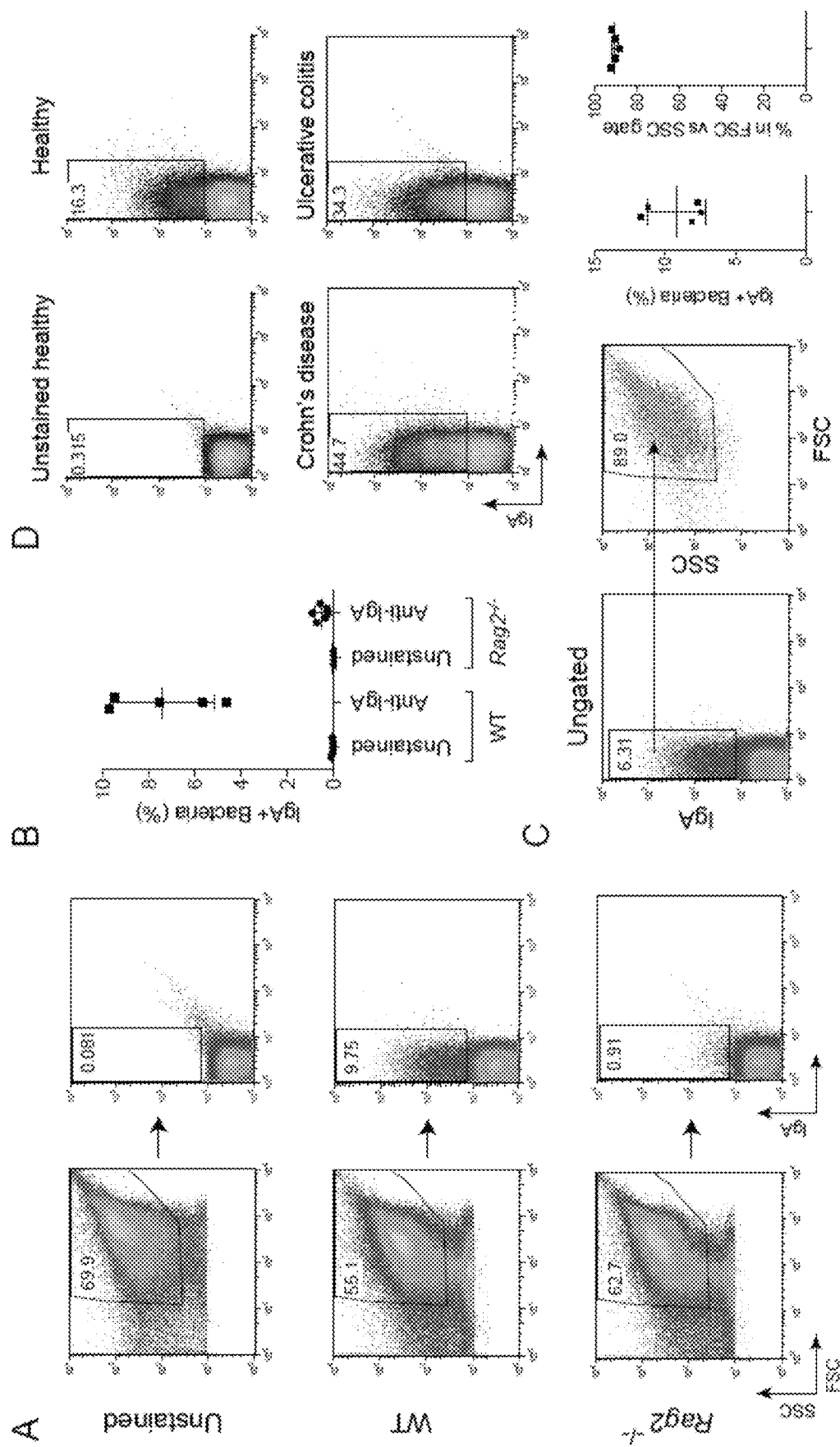
Figures 6E, 6F, 6G:
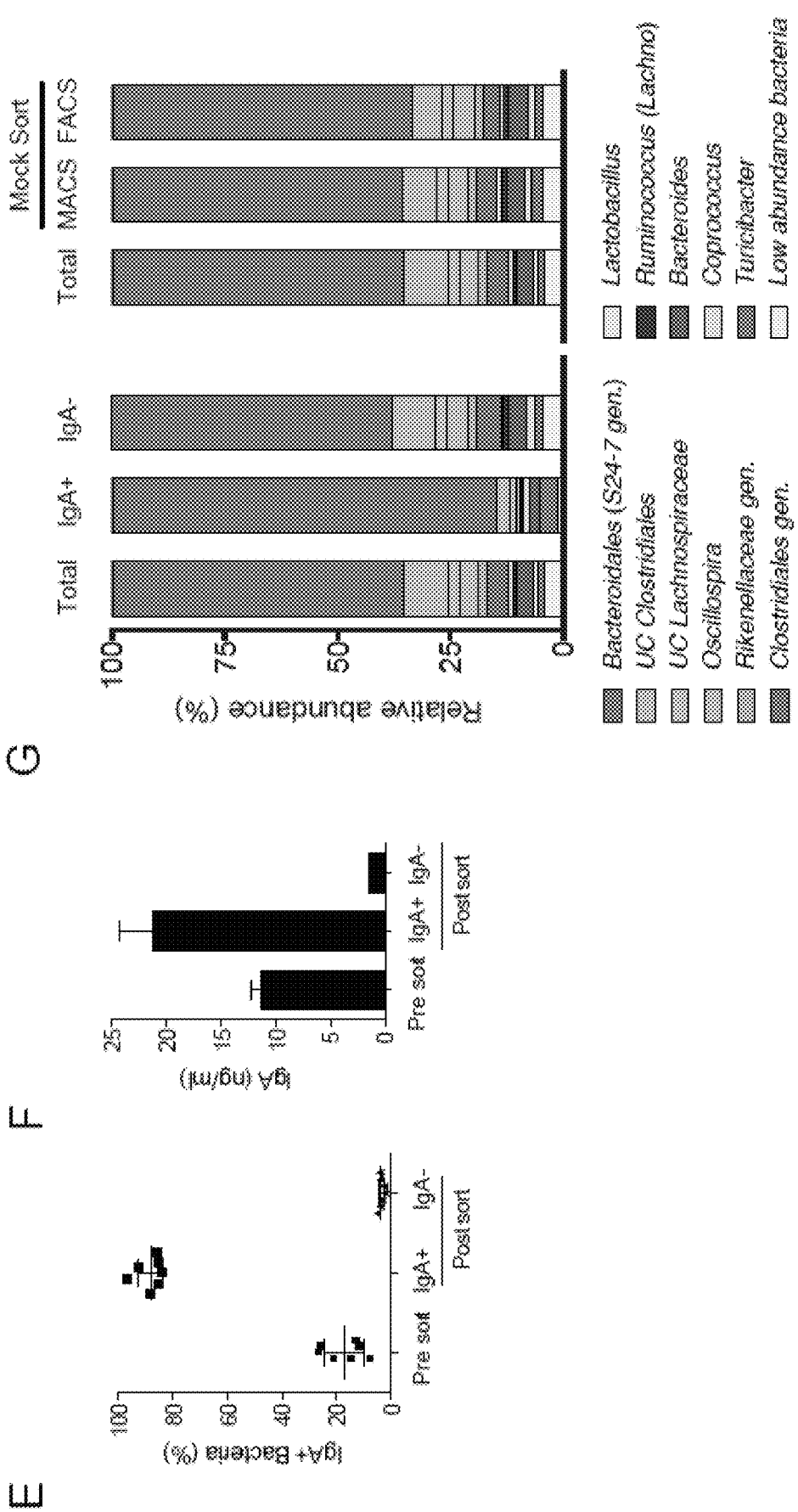
Figures 6H, 6I, 6J:
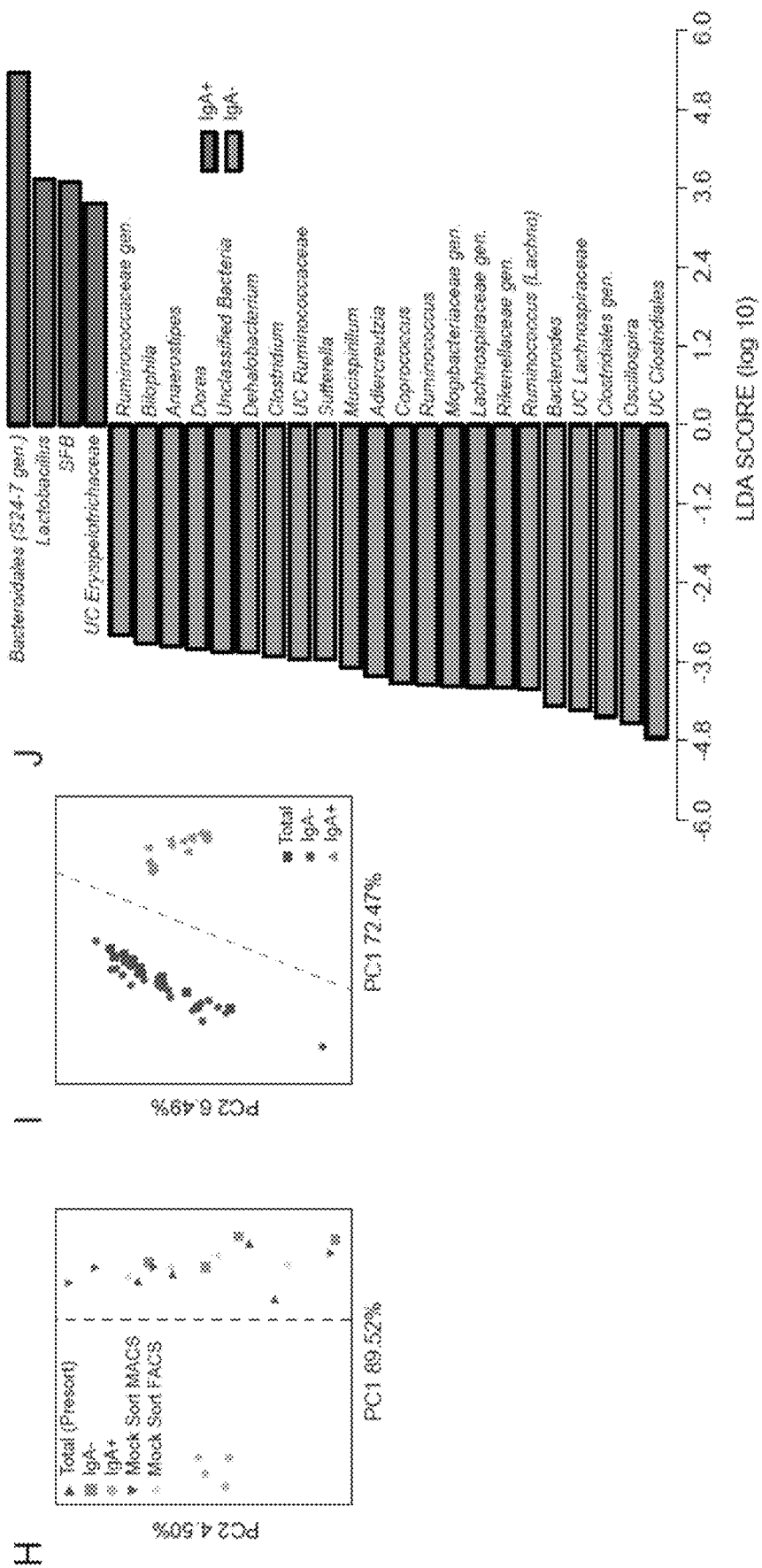

FIG. 6, comprising FIGS. 6A-6J, depicts the results of experiments analyzing the IgA coating of fecal bacteria from SPF C57Bl/6 mice. (FIG. 6A) Representative staining of fecal bacteria from C57Bl/6 SPF (n=5) and Rag2$^{-/-}$ mice (n=6), which lack immunoglobulins, with anti-IgA. Data is representative of more than 5 independent experiments. (FIG. 6B) Dot plot of all mice from (6A). (FIG. 6C) Gating on IgA coated bacteria demonstrates that the vast majority of IgA+ events fall within the designated FSC and SSC gate. SSC, side scatter. FSC, forward scatter. Data is representative of more than 5 independent experiments. (FIG. 6D) Representative staining of fecal bacteria from healthy humans, and Crohn's disease and ulcerative colitis patients with anti-IgA. Data for all patients is shown in FIG. 3A. (FIG. 6E) Purity of IgA+ and IgA− fractions after MACS and FACS sorting as determined by flow cytometry (Presort: 17.2%±2.8; IgA+: 88.3±1.8; IgA−: 3.6±0.4). Indicated are mean±standard error of the mean. (FIG. 6F) IgA concentrations in total, IgA+ and IgA− bacterial fractions after MACS sorting as determined by whole bacterial-cell ELISA. Indicated are mean±standard error of the mean. (FIG. 6G) Average relative abundance of bacterial genera in Presort (Total), IgA+, IgA−, and mock-sorted (MACS and FACS) samples (n=4 mice). Depicted are bacteria of >1% abundance. UC, unclassified in the Greengenes reference database. Gen., classified as a distinct but unnamed genus in the Greengenes reference database. (FIG. 6H) Principal Coordinates Analysis of weighted UniFrac distances of Presort (total fecal bacteria), IgA+, IgA−, and mock-sorted (MACS and FACS) samples. PC, Principal Coordinate. PERMANOVA comparisons of weighted UniFrac distances of Presort, IgA+, IgA−, and mock-sorted samples demonstrated that IgA+ bacteria were distinct from Presort and IgA− fractions (P<0.05), while IgA− bacteria were not significantly different from total bacteria (P=0.266). Mock sorting did not significantly alter the observed phylogenetic composition of fecal bacteria (Presort versus MACS: P=0.655; Presort versus FACS: P=0.606). For MACS mock-sorting, samples were stained with anti-IgA and sorted by MACS before recombining positive and negative fractions (Mock Sort MACS); for FACS mock-sorting, Mock Sort MACS samples were sorted by FACS by gating on total bacteria by FSC/SCC (Mock Sort FACS). (FIG. 6I) Principal Coordinate Analysis of weighted UniFrac distances of Total (Presort), IgA+ and IgA− fecal bacteria from SPF mice (n=17 sampling event). PC, Principal Coordinate. (FIG. 6J) LEfSe comparisons of IgA+ and IgA− bacterial genera from SPF mice. Taxa that are significantly enriched in the IgA+ fraction are depicted in red, and taxa that are significantly enriched in the IgA− fraction are depicted in green. Significance levels for LEfSe were P<0.05 and Linear Discriminant Analysis (LDA) Score >2. UC, unclassified by the Greengenes reference database. Gen., classified as a distinct but unnamed genus by the Greengenes reference database.

Figures 7A, 7B:
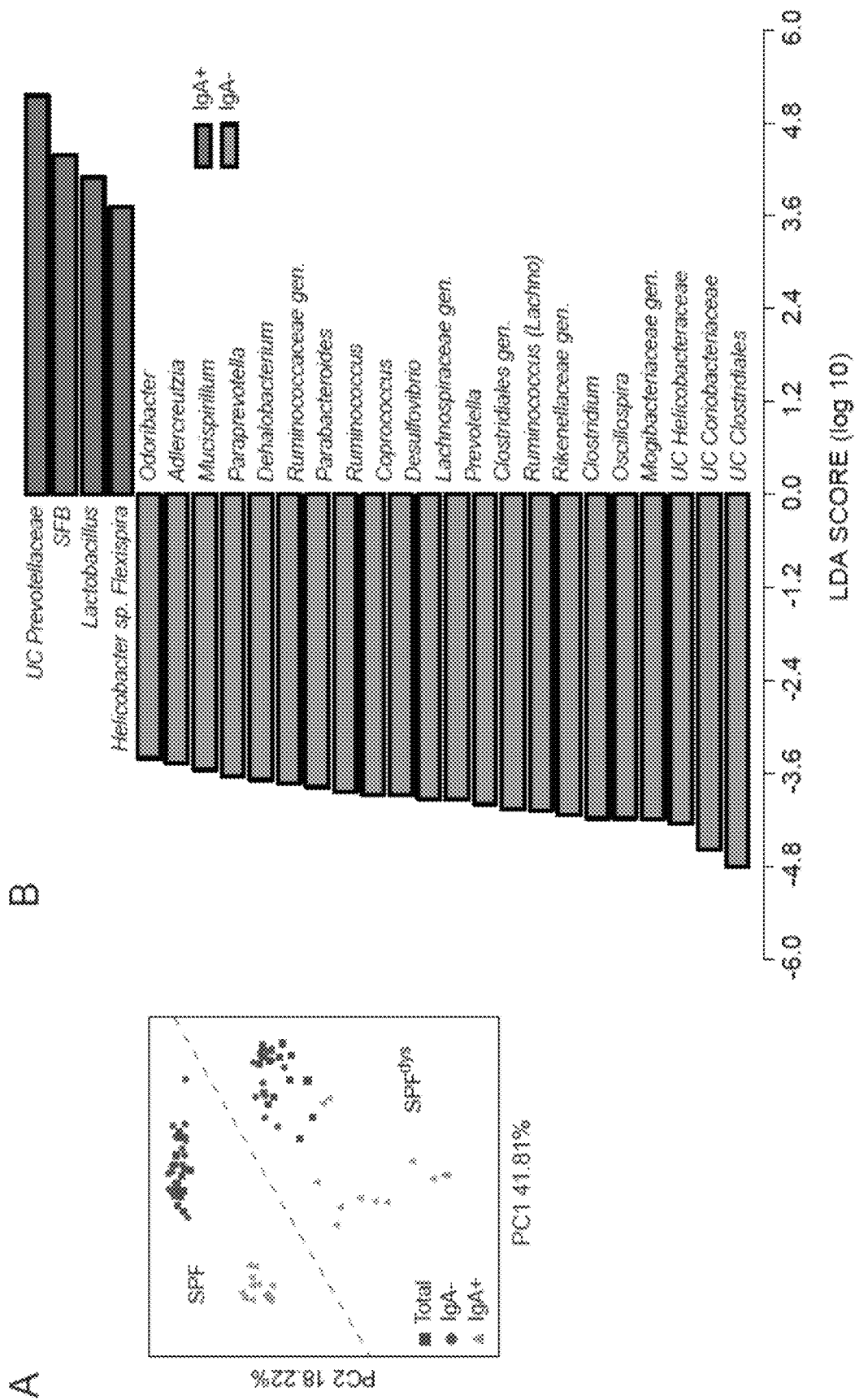
Figure 7C:
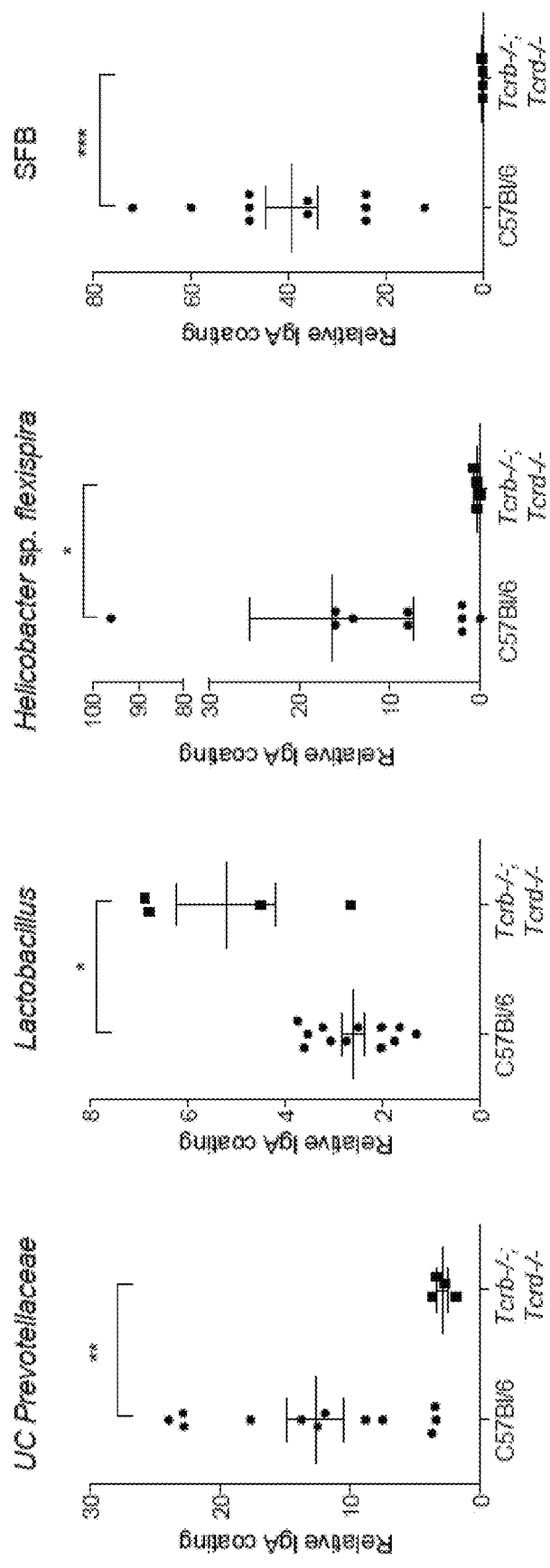

FIG. 7, comprising FIGS. 7A-7C, depicts the results of experiments analyzing the IgA coating of intestinal bacteria from SPF$^{dys}$ mice, and dysbiotic wild-type and T cell-deficient mice. (FIG. 7A) Principal Coordinate Analysis of weighted UniFrac distances of Total (Presort), IgA+ and IgA− fecal bacteria from SPF (n=17 sampling events) and SPF$^{dys}$ mice (n=14 sampling events). PC, Principal Coordinate. (FIG. 7B) LEfSe comparisons of IgA+ and IgA− bacterial genera from SPF$^{dys}$ mice. Taxa that are significantly enriched in the IgA+ fraction are depicted in red, and taxa that are significantly enriched in the IgA− fraction are depicted in green. Significance levels for LEfSe were P<0.05 and Linear Discriminant Analysis (LDA) Score >2. (FIG. 7C) IgA Coating Index (ICI) scores in dysbiotic WT C57Bl/6 and T cell-deficient (Tcrb−/−; Tcrd−/−) mice. C57Bl/6 and Tcrb−/−; Tcrd−/− mice were co-housed with Asc$^{-/-}$ mice for at least 6 weeks to allow for the acquisition of dysbiosis. *P<0.05; P<0.01; *P<0.001 (Wilcoxon rank-sum).

Figure 8:
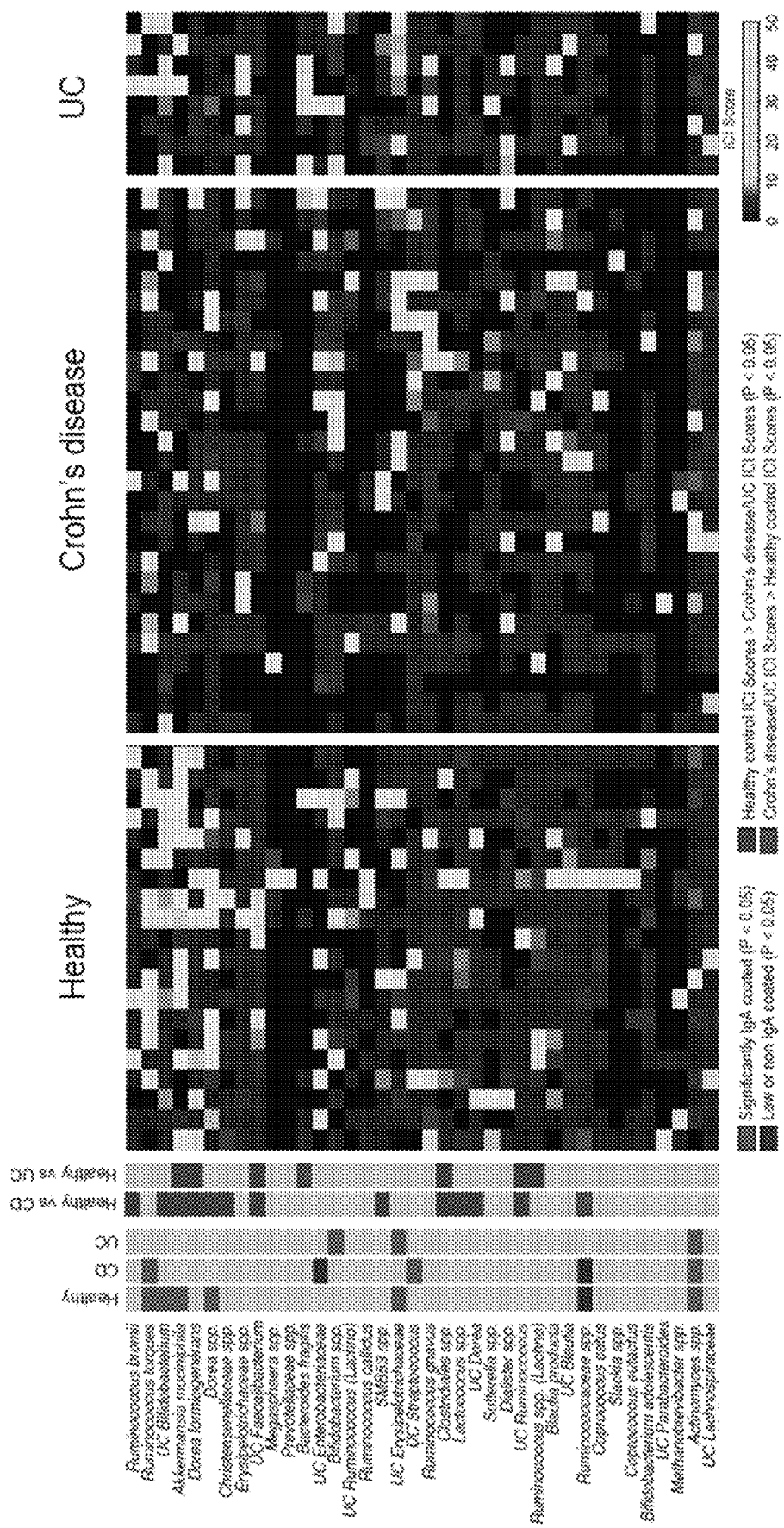
Figure 8:
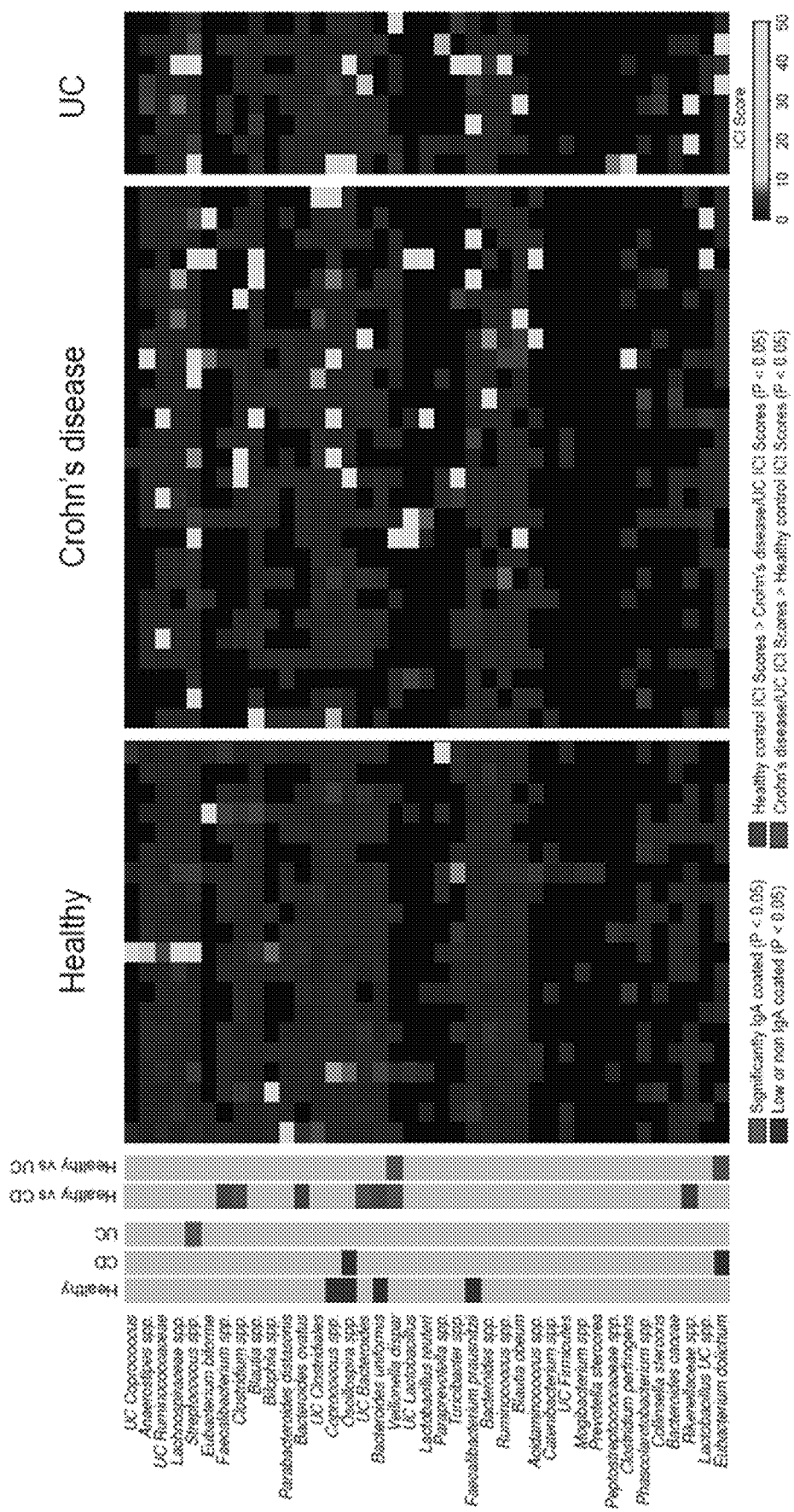
Figure 8:
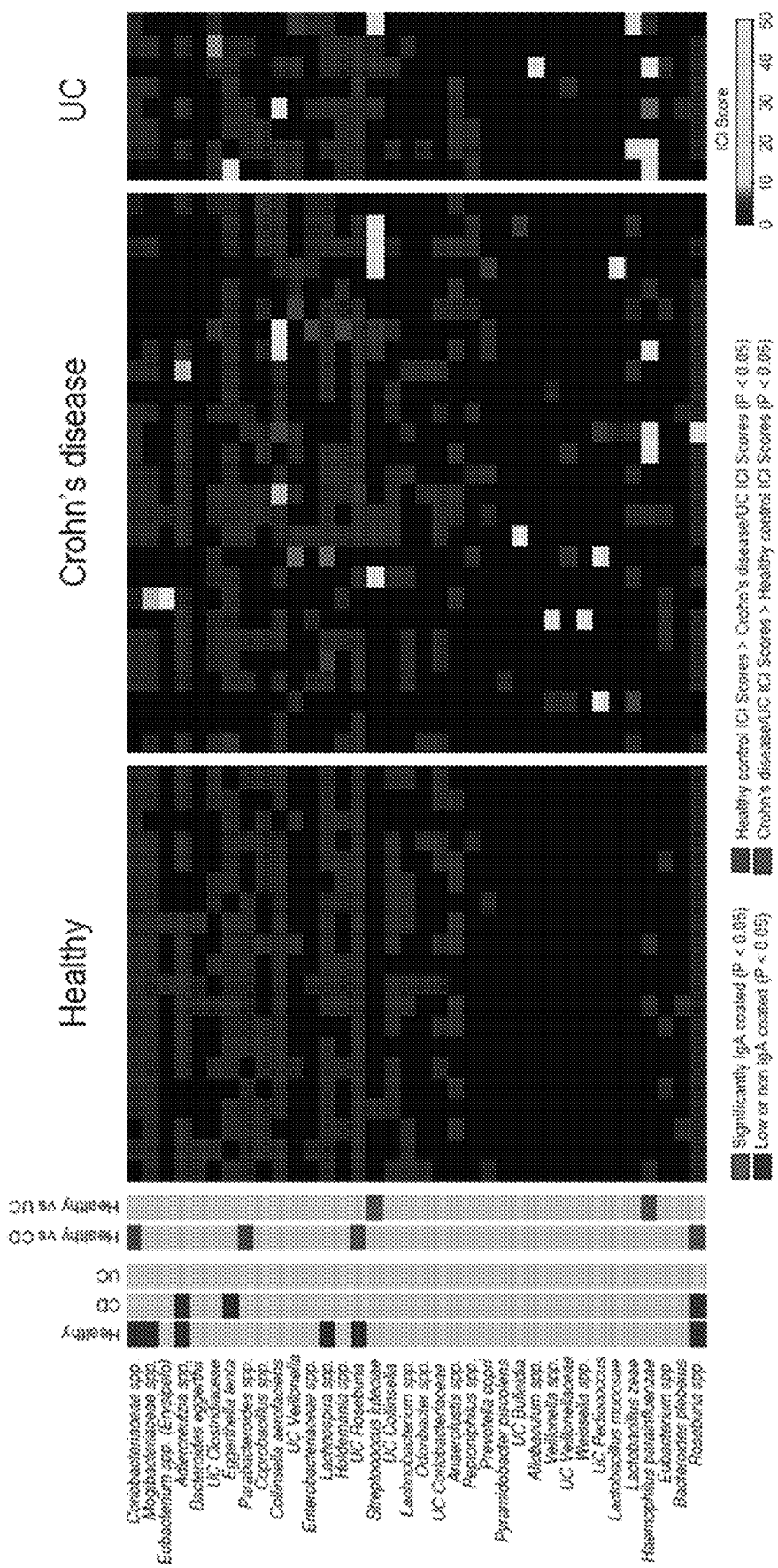

FIG. 8 depicts the results of experiments analyzing the IgA coating of fecal bacteria from healthy humans, Crohn's disease patients, and patients with ulcerative colitis. Depicted in the main heatmap (black, blue, yellow) are IgA coating index (ICI) scores for bacterial species from 20 healthy humans, 27 Crohn's disease (CD) patients, and 8 patients with ulcerative colitis (UC). Each column represents an individual human subject. Bacterial taxa are clustered (complete linkage clustering using Euclidean distance) based on ICI scores observed in healthy humans. The first three columns on the left (red, gray, blue) summarize the statistical comparisons between relative taxonomic abundance in the IgA+ and IgA− fraction in each patient group. Bacterial taxa with significantly higher relative abundance in the IgA+ fraction as compared to the IgA− fraction by LEfSe and Wilcoxon rank-sum are red; bacterial taxa with significantly lower relative abundance in the IgA+ fraction as compared to the IgA− fraction are blue; and bacterial taxa showing no significant difference in abundance in the IgA+ and IgA− fractions are grey. The fourth and fifth columns on the left summarize statistical comparisons between ICI scores in healthy subjects and IBD patients: gray marks no difference between diseased and control, green marks taxa where ICI scores are significantly higher in healthy controls than in diseased patients, and purple marks taxa where ICI scores are significantly lower in healthy controls than in diseased patients. Significance levels for LEfSe and Wilcoxon rank-sum were P<0.05 and Linear Discriminant Analysis Score >2, and P<0.05, respectively. UC, unclassified in the Greengenes reference database. Spp., classified as a distinct but unnamed species in the Greengenes reference database.

Figure 9:
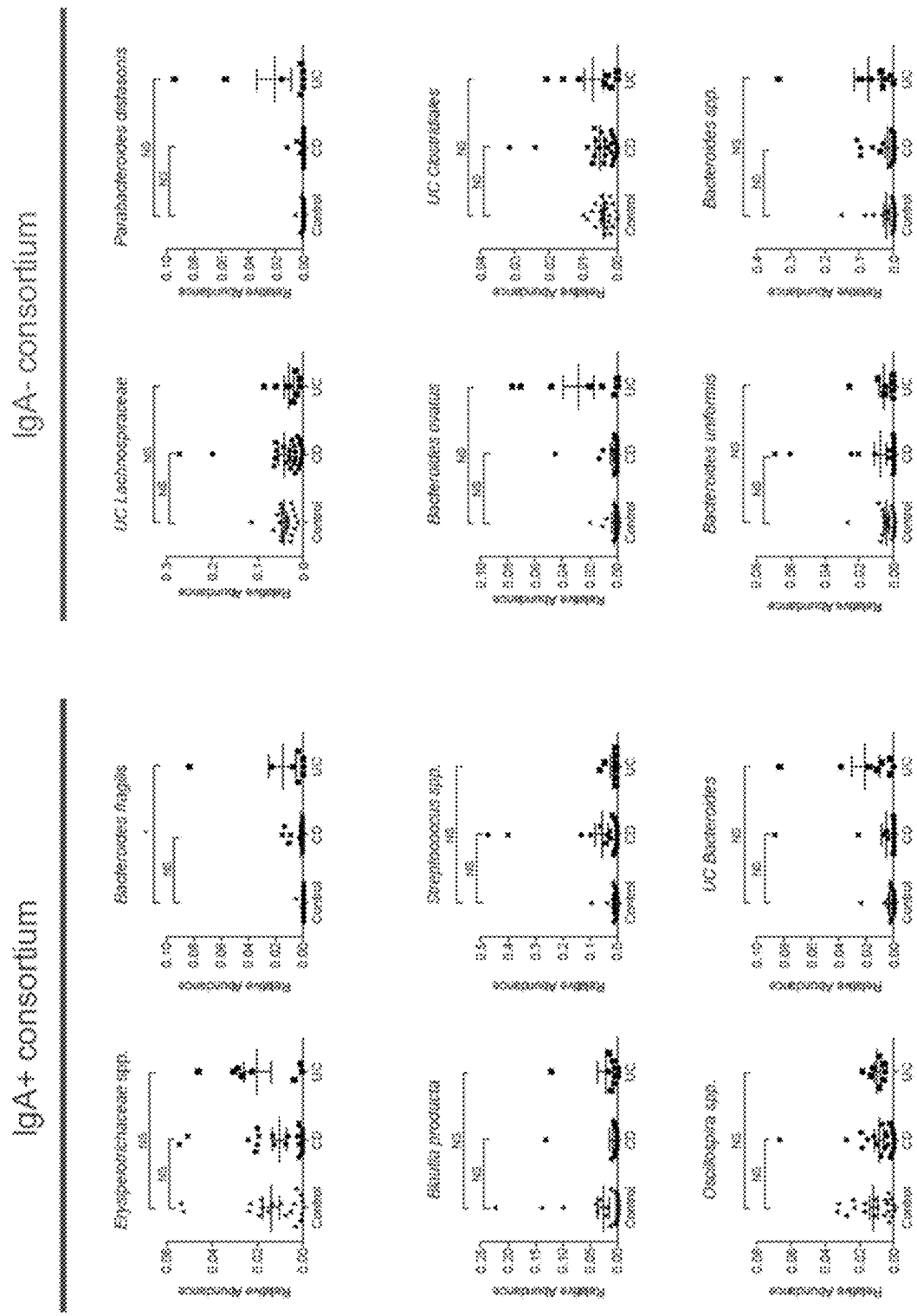
Figure 9:
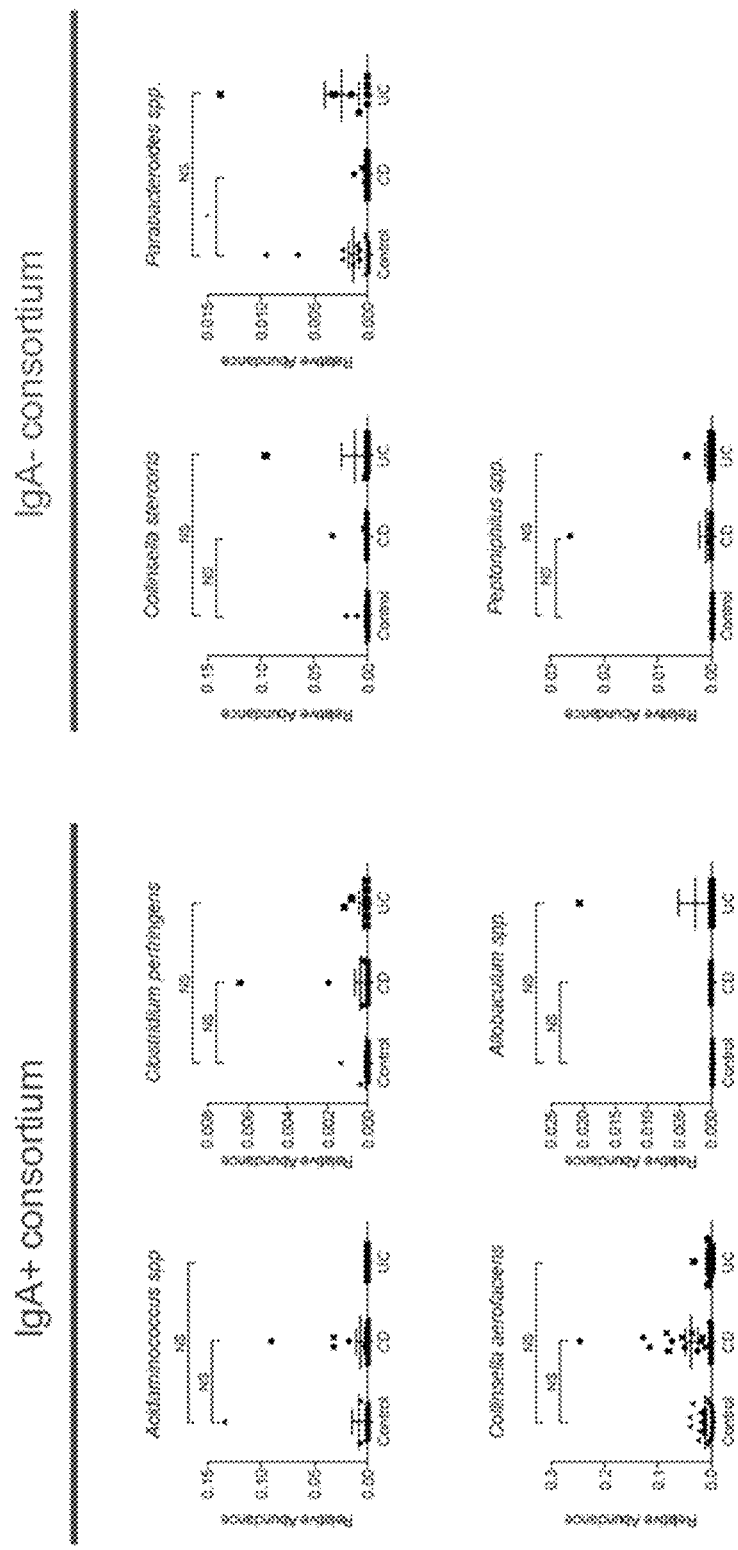

FIG. 9 depicts the results of experiments demonstrating the relative abundance of bacterial taxa comprising the IgA+ and IgA− consortia. NS=not significant; *P<0.05 (Wilcoxon rank-sum). Indicated are mean±standard error of the mean.

Figures 10A, 10B, 10C, 10D, 10E:
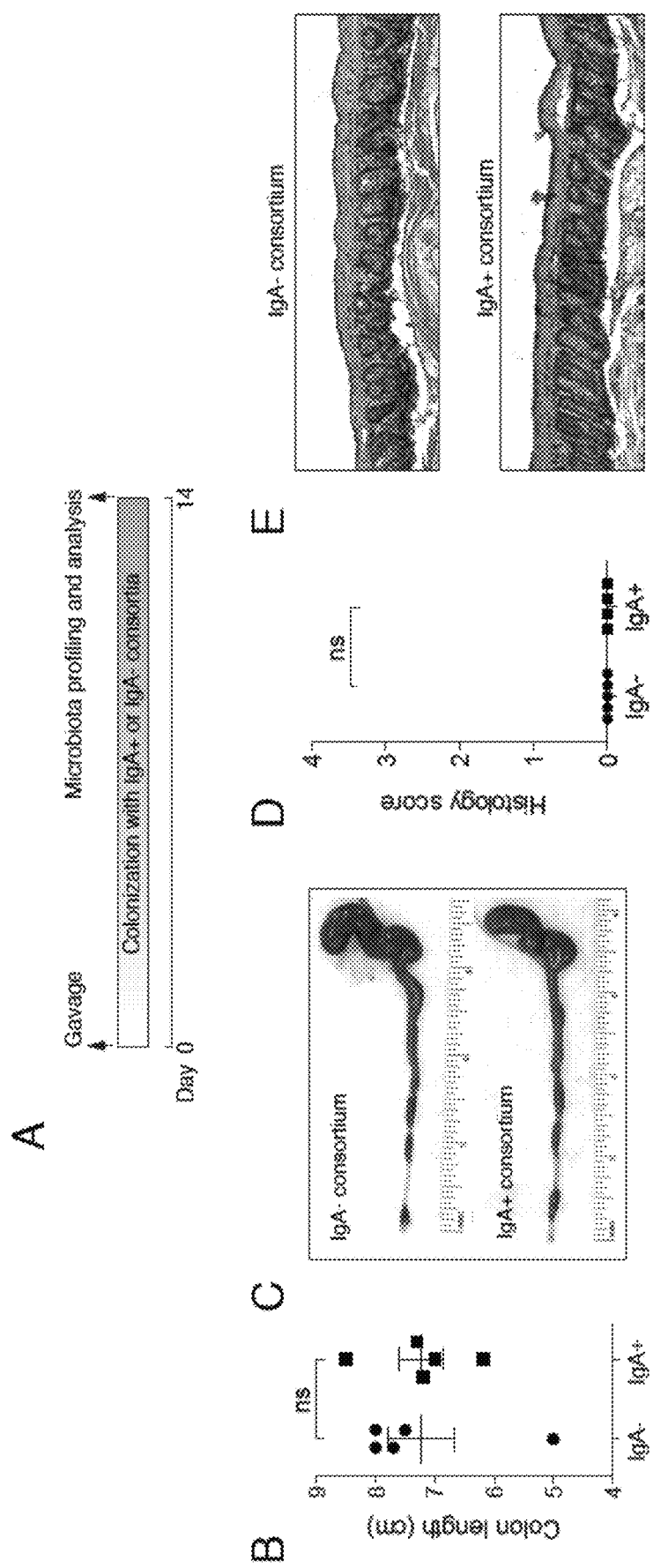
Figures 10F, 10G:
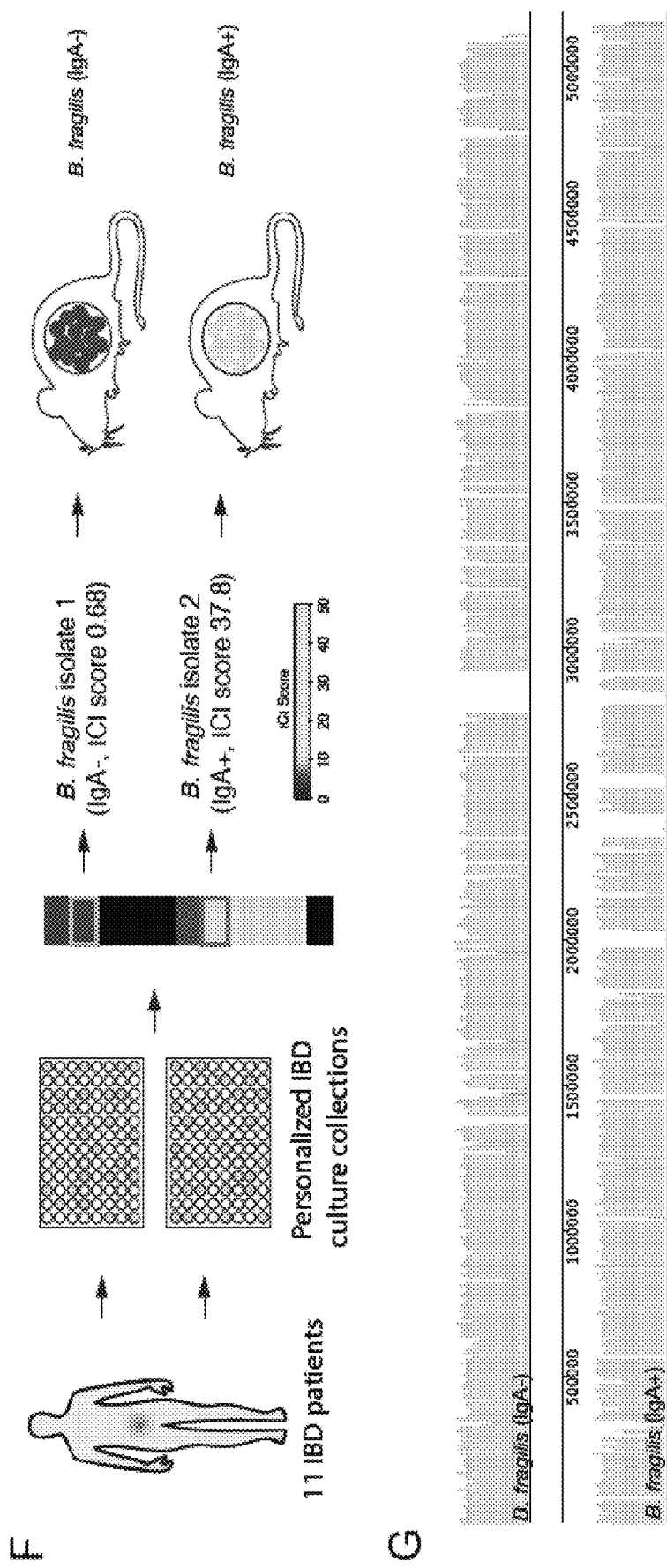

FIG. 10, comprising FIGS. 10A-10J, depicts the results of experiments demonstrating that IBD-associated IgA+ and IgA− bacterial consortia do not induce inflammatory responses under homeostatic conditions in gnotobiotic mice, and differential IgA coating identifies distinct strains of B. fragilis. (FIG. 10A) Colonization of germ-free mice with IgA+ and IgA− consortia. (FIG. 10B) Colon length after 14 days of bacterial colonization. ns, not significant (unpaired Student's t-test). (FIG. 10C) Gross pathology of large bowels. (FIG. 10D) Colon histopathology scores. Scores were assigned as follows: 0, Intact colonic architecture. No acute inflammation or epithelial injury; 1, Focal minimal acute inflammation; 2, Focal mild acute inflammation; 3, Severe acute inflammation with multiple crypt abscesses and/or focal ulceration; 4, Severe acute inflammation, multiple crypt abscesses, epithelial loss and extensive ulceration. ns, not significant (unpaired Student's t-test). (FIG. 10E) Representative histology pictures from hematoxylin and eosin stained colons. (FIG. 10F) Selection of differentially coated isolates/strains of B. fragilis from human gut microbiota culture collections and monocolonization of germ-free mice. (FIG. 10G) Similarity profiles of B. fragilis (IgA−) and B.

*fragilis* (IgA+) draft genomes aligned via progressive Mauve. The height of the profile represents the level of conservation. Sections depicted in white are absent from the comparison strain. (FIG. 10H) Colon length after DSS. **P<0.005 (unpaired Student's t-test). (FIG. 10I) Colon histopathology scores 6 days after DSS. Scores were assigned as follows: 0, Intact colonic architecture. No acute inflammation or epithelial injury; 1, Focal minimal acute inflammation; 2, Focal mild acute inflammation; 3, Severe acute inflammation with multiple crypt abscesses and/or focal ulceration; 4, Severe acute inflammation, multiple crypt abscesses, epithelial loss and extensive ulceration. (FIG. 10J) Representative histology pictures from hematoxylin and eosin stained colons after DSS.

Figure 11:
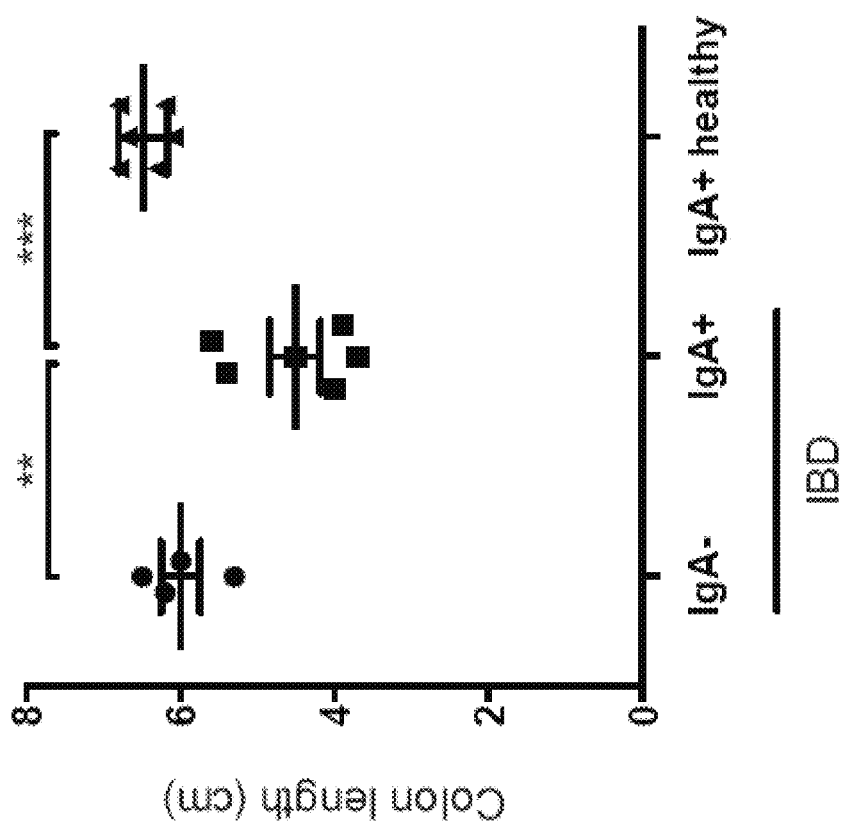

FIG. 11 depicts the results of experiments demonstrating that IgA+ bacteria from healthy humans, unlike IgA+ bacteria from IBD patients, are non-colitogenic. Germ-free mice were colonized with IgA− bacteria or IgA+ bacteria from IBD patients, or IgA+ bacteria from healthy humans. One week post-colonization, mice were treated with 2.5% DSS ad libitum and colon length was measured at day 6 post-DSS. **P<0.01; N.S. not significant. (One way ANOVA).

Figure 12:
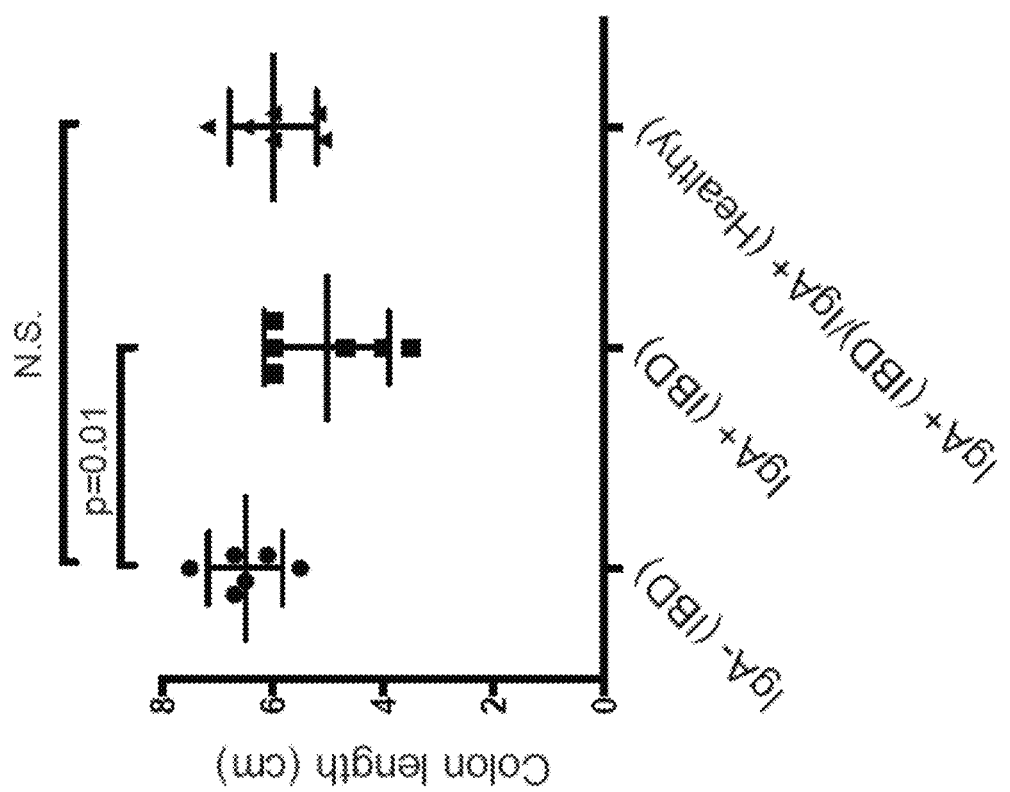

FIG. 12 depicts the results of experiments demonstrating that IgA+ species from healthy humans can protect against colitogenic IgA+ species from patients with IBD. Germ-free mice were colonized with non-colitogenic IgA− bacteria (IgA− (IBD)), or colitogenic IgA+ bacteria from IBD patients with (IgA+(IBD)/IgA+(Healthy)) or without (IgA+ (IBD)) IgA+ bacteria from healthy individuals. One week post-colonization, mice were treated with 2% DSS ad libitum and colon length was measured at day 6 post-DSS. N.S. not significant (One-way ANOVA).

Figure 13:
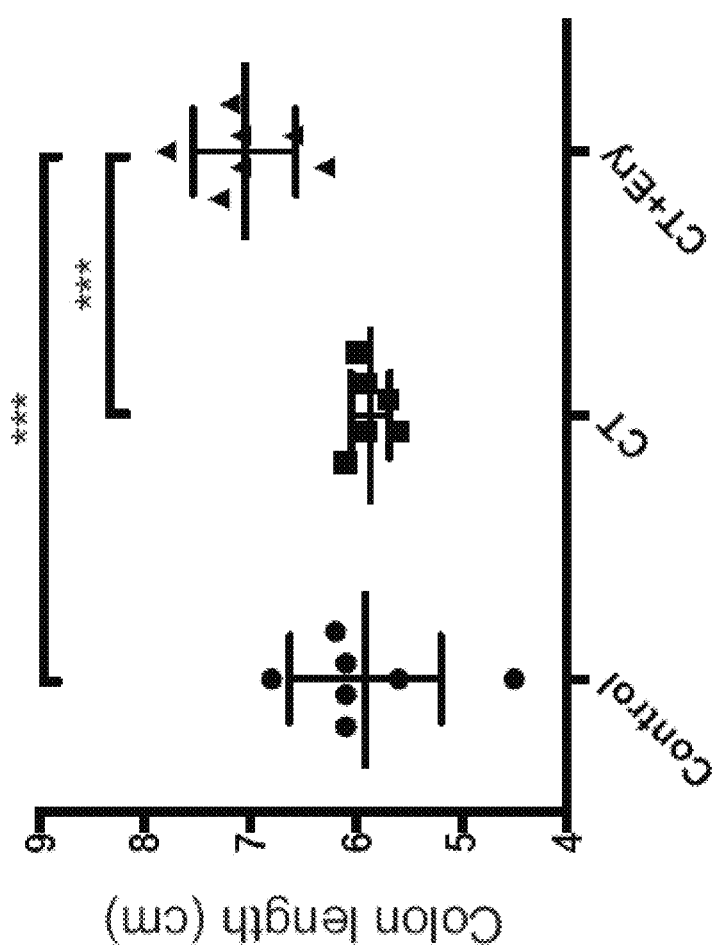

FIG. 13 depicts the results of experiments demonstrating that oral immunization protects against bacterial-driven colitis. Germ-free mice were colonized with a colitogenic microbiota consisting of nine strains of non-colitogenic bacteria (IgA− consortium) and one known colitogenic species (*Erysipelotrichaceae* sp.) that was previously isolated from a patient with IBD and identified based on high IgA-coating. After one week of colonization, mice were immunized with Cholera Toxin (CT) alone or CT plus heat-killed *Erysipelotrichaceae* once weekly for 6 weeks by oral gavage. After 8 weeks, mice were treated with 1.8% DSS to induce colitis and colon length was measured at day 6 post-DSS. ***P<0.001 (One way ANOVA).

DETAILED DESCRIPTION

The present invention relates to the discovery that secretory antibodies can be used to detect and identify microbes present in the microbiota of a subject that influence susceptibility to or contribute to the development or progression of diseases or disorders.

Further, the present invention relates to methods of modifying an altered microbiota having secretory antibody-coated constituents in a subject in need thereof. In some embodiments, the invention provides compositions and methods for diminishing constituents of an altered microbiota that are over-represented in the altered microbiota as compared with a normal microbiota, such as over-represented secretory antibody-coated constituents, to restore the subject's microbiota to a normal microbiota. For example, in certain embodiments, the invention comprises compositions and methods relating to a vaccine which induces an immune response against one or more bacteria associated with the development or progression of a disease or disorder, thereby reducing the amount of the one or more bacteria in a subject. In other embodiments, the invention provides compositions and methods for supplementing constituents of an altered microbiota that are under-represented in the altered microbiota, as compared with a normal microbiota, to restore the subject's microbiota to a normal microbiota. In further embodiments, the invention provides compositions and methods for both supplementing constituents of an altered microbiota that are under-represented in the altered microbiota, as compared with a normal microbiota, as well as diminishing constituents of an altered microbiota that are over-represented in the altered microbiota, as compared with a normal microbiota, to restore the subject's microbiota to a normal microbiota. In further embodiments, the invention provides a method for identifying a "surgical probiotic," which are desired, preferred, neutral or beneficial strains of bacteria that are phylogenetically similar to disease-associated strains of the bacteria.

In certain embodiments, the present invention provides methods that combine flow cytometry-based microbial cell sorting and genetic analyses to detect, to isolate and to identify secretory antibody-coated (e.g., IgA-coated) microbes from the microbiota of a subject. Because disease-causing members of the microbiota, including pathobionts, are recognized by the subject's immune system, their presence triggers an immune response, including antibody production and secretion. In some embodiments of the methods described herein, the presence of an immune response (e.g., antibody production and secretion) in the subject serves as a marker and a means for isolating and identifying pathobionts, and putative pathobionts, that are the targets of the subject's immune response. Thus, the methods described herein can isolate and identify microbes present in the microbiota of a subject that influence susceptibility to or contribute to the development or progression of a disease or disorder. The microbiota of the subject can be any microbiota present on any mucosal surface of subject where antibody is secreted, including the gastrointestinal tract, the respiratory tract, genitourinary tract and mammary gland.

In various embodiments, the present invention relates to the isolation and identification of members of the microbiota that influence the development and progression of a disease or disorder, such as an inflammatory disease or disorder. Thus, the invention relates to compositions and methods for detecting and determining the identity of secretory antibody-coated constituents of a subject's microbiota to determine whether the secretory antibody-coated constituents of a subject's microbiota contribute to an altered microbiota associated with an inflammatory disease or disorder. In various embodiments, the relative proportions of the secretory antibody-coated and uncoated constituents of a subject's microbiota are indicative of an altered microbiota associated with an inflammatory disease or disorder. In some embodiments, the detection and identification of secretory antibody-coated constituents of the microbiota of the subject are used to diagnose the subject as having, or as at risk of developing, an inflammatory disease or disorder. Thus, in some embodiments, the altered microbiota of a subject influences susceptibility to or contributes to the development or progression of a disease or disorder, such as an inflammatory disease or disorder. In various embodiments, the inflammatory diseases and disorders associated with altered microbiota having secretory antibody-coated constituents include, but are not limited to, at least one of: inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), or non-alcoholic steatohepatitis (NASH).

As used throughout herein, constituents of an altered microbiota that are over-represented in the altered microbiota as compared with a normal microbiota, include constituents that are uniquely present in the altered microbiota as compared with a normal microbiota.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "dysbiosis," as used herein, refers to imbalances in quality, absolute quantity, or relative quantity of members of the microbiota of a subject, which is sometimes, but not necessarily, associated with the development or progression of a disease or disorder.

The term "microbiota," as used herein, refers to the population of microorganisms present within or upon a subject. The microbiota of a subject includes commensal microorganisms found in the absence of disease and may also include pathobionts and disease-causing microorganisms found in subjects with or without a disease or disorder.

The term "pathobiont," as used herein, refers to potentially disease-causing members of the microbiota that are present in the microbiota of a non-diseased or a diseased subject, and which has the potential to contribute to the development or progression of a disease or disorder.

An "effective amount" or "therapeutically effective amount" of a compound is that amount of a compound which is sufficient to provide a beneficial effect to the subject to which the compound is administered.

As used herein, an "instructional material" includes a publication, a recording, a diagram, or any other medium of expression which can be used to communicate the usefulness of a compound, composition, or method of the invention in a kit. The instructional material of the kit of the invention can, for example, be affixed to a container which contains the identified compound, composition, or method of the invention or be shipped together with a container which contains the identified compound, composition, or method of the invention. Alternatively, the instructional material can be shipped separately from the container with the intention that the instructional material and the compound, composition, or method of the invention be used cooperatively by the recipient.

The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

The terms "patient," "subject," "individual," and the like are used interchangeably herein, and refer to any animal, or cells thereof whether in vitro or in vivo, amenable to the methods described herein. In certain non-limiting embodiments, the patient, subject or individual is, by way of non-limiting examples, a human, a dog, a cat, a horse, or other domestic mammal.

A "therapeutic" treatment is a treatment administered to a subject who exhibits signs or symptoms of pathology, for the purpose of diminishing or eliminating those signs or symptoms.

As used herein, "treating a disease or disorder" means reducing the severity and/or frequency with which a sign or symptom of the disease or disorder is experienced by a patient. Disease and disorder are used interchangeably herein.

The phrase "biological sample" as used herein, is intended to include any sample comprising a cell, a tissue, feces, or a bodily fluid in which the presence of a microbe, nucleic acid or polypeptide is present or can be detected. Samples that are liquid in nature are referred to herein as "bodily fluids." Biological samples may be obtained from a patient by a variety of techniques including, for example, by scraping or swabbing an area of the subject or by using a needle to obtain bodily fluids. Methods for collecting various body samples are well known in the art.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

The term "antigen" or "Ag" as used herein is defined as a molecule that provokes an adaptive immune response. This immune response may involve either antibody production, or the activation of specific immunogenically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequences or a partial nucleotide sequence encoding a protein that elicits an adaptive immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a microbiota sample, tissue sample, a tumor sample, a cell or a biological fluid.

The term "adjuvant" as used herein is defined as any molecule to enhance an antigen-specific adaptive immune response.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes and binds to a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "probiotic" refers to one or more bacteria that can be administered to a subject to aid in the restoration of a subject's microbiota by increasing the number of bacteria that are desired, preferred, neutral, beneficial and/or under-represented in the subject's microbiota. Similarly, a "surgical probiotic' is a strain of bacteria that is desired, preferred, neutral, beneficial and/or under-represented in the subject's microbiota and that is phylogenetically similar to a disease-associated strain of the bacteria.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the discovery that secretory antibodies, such as IgA1, IgA2 or IgM, can be used to detect and identify microbes present in the microbiota of a subject that influence susceptibility to or contribute to the development or progression of a diseases or disorder, such as an inflammatory disease or disorder. Thus, in certain aspects the present invention relates to methods of modifying an altered microbiota population in a subject in need thereof. For example, in certain embodiments, the present invention relates to compositions and methods of reducing the level of one or more bacteria associated with the development or progression of a disease or disorder. In one embodiment, the invention provides a vaccine that reduces the amount of one or more bacteria associated with the development or progression of a disease or disorder. For example, in certain embodiments, the vaccine comprises an inactivated bacteria associated with the development or progression of a disease or disorder, thereby inducing an immune response against the bacteria.

In one embodiment, the invention relates to compositions and methods for detecting, identifying and determining the absolute number or relative proportions of the secretory antibody-coated and uncoated constituents of a subject's microbiota, to determine whether a subject's microbiota is an altered microbiota associated with a disease or disorder, such as an inflammatory disease or disorder. The microbiota of the subject can be any microbiota present on any mucosal surface of subject where antibody is secreted, including the gastrointestinal tract, the respiratory tract, genitourinary tract and mammary gland.

Methods of Treatment

In some embodiments, the invention relates to methods of modifying an altered microbiota having secretory antibody-coated constituents in a subject in need thereof.

In other embodiments, the invention provides compositions and methods for diminishing constituents of an altered microbiota that are over-represented in the altered microbiota as compared with a normal microbiota, such as over-represented secretory antibody-coated constituents, to restore the subject's microbiota to a normal microbiota. As used throughout herein, constituents of an altered microbiota that are over-represented in the altered microbiota as compared with a normal microbiota, include constituents that are uniquely present in the altered microbiota as compared with a normal microbiota.

In some embodiments, the invention provides compositions and methods for supplementing constituents of an altered microbiota that are desired, preferred, neutral, beneficial and/or under-represented in the altered microbiota, as compared with a normal microbiota, to restore the subject's microbiota to a normal microbiota.

In further embodiments, the invention provides compositions and methods for both supplementing constituents of an altered microbiota that are under-represented in the altered microbiota, as well as diminishing constituents of an altered microbiota that are over-represented in the altered microbiota, as compared with a normal microbiota, to restore the subject's microbiota to a normal microbiota. The microbiota of the subject can be any microbiota present on any mucosal surface of subject where antibody is secreted, including the gastrointestinal tract, the respiratory tract, genitourinary tract and mammary gland.

In conjunction with the diagnostic methods, the present invention also provides therapeutic methods for treating an inflammatory disease or disorder associated with an altered microbiota including secretory antibody-coated microbes, by modifying the microbiota to that observed in a healthy subject. In some embodiments, the methods supplement the numbers of the types of microbes that are under-represented in the altered microbiota. In other embodiments, the methods diminish the numbers or pathogenic effects of the types of microbes, including secretory antibody-coated microbes that are overrepresented in the altered microbiota. In a further embodiment, the methods both supplement the numbers of the types of bacteria that are under-represented in the altered microbiota, and diminish the numbers of the types of bacteria that are overrepresented in the altered microbiota. In various embodiments, the inflammatory diseases and disorders treatable by the methods of the invention include, but are not limited to: inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), or non-alcoholic steatohepatitis (NASH).

Vaccine

In other embodiments, modification of the altered microbiota having over-represented secretory antibody-coated constituents is achieved by administering to a subject in need thereof a therapeutically effective amount of a vaccine to induce an immune response against the over-represented constituent, wherein the administered vaccine and ensuing immune response diminishes the number or pathogenic effects of at least one type (e.g., genus, species, strain, sub-strain, etc.) of secretory antibody-coated bacteria that is over-represented in the altered microbiota, as compared with a normal microbiota. In various embodiments, the at least one type (e.g., genus, species, strain, sub-strain, etc.) of bacteria that is diminished using the methods of the invention includes a Segmented Filamentous Bacteria (SFB) or *Helicobacter flexispira*, or a bacteria from at least one family selected from the group consisting of *Lactobacillus, Helicobacter*, S24-7, *Erysipelotrichaceae* and *Prevotellaceae*. In some embodiments, the bacteria from the family *Prevotellaceae* is a bacteria from the genera of *Paraprevotella* or *Prevotella*. In other embodiments, the secretory antibody-coated constituent of the subject's microbiota associated with the development or progression of an inflammatory disease or disorder in the subject is at least one strain of at least one bacteria selected from *Acidaminococcus* spp., *Actinomyces* spp., *Akkermansia muciniphila, Allobaculum* spp., *Anaerococcus* spp., *Anaerostipes* spp., *Bacteroides* spp., *Bacteroides* Other, *Bacteroides acidifaciens, Bacteroides coprophilus, Bacteroides fragilis, Bacteroides ovatus, Bacteroides uniformis, Barnesiellaceae* spp., *Bifidobacterium adolescentis, Bifidobacterium* Other, *Bifidobacterium* spp., *Bilophila* spp., *Blautia obeum, Blautia producta, Blautia* Other, *Blautia* spp., *Bulleidia* spp., *Catenibacterium* spp., *Citrobacter* spp., *Clostridiaceae* spp., *Clostridiales* Other, *Clostridiales* spp., *Clostridium perfringens, Clostridium* spp., *Clostridium* Other, *Collinsella aerofaciens, Collinsella* spp., *Collinsella stercoris, Coprococcus catus, Coprococcus* spp., *Coriobacteriaceae* spp., *Desulfovibrionaceae* spp., *Dialister* spp., *Dorea formicigenerans, Dorea* spp., *Dorea* Other, *Eggerthella lenta, Enterobacteriaceae* Other, *Enterobacteriaceae* spp., *Enterococcus* spp., *Erysipelotrichaceae* spp., *Eubacterium biforme, Eubacterium biforme, Eubacterium dolichum, Eubacterium* spp., *Faecalibacterium prausnitzii, Fusobacterium* spp., *Gemellaceae* spp., *Haemophilus parainfluenzae, Haemophilus* Other, *Helicobacter* spp., *Helicobacter Lachnospiraceae* Other, *Lachnospiraceae* spp., *Lactobacillus reuteri, Lactobacillus mucosae, Lactobacillus zeae, Lactobacillus* spp., *Lactobacillaceae* spp., *Lactococcus* spp., *Leuconostocaceae* spp., *Megamonas* spp., *Megasphaera* spp., *Methanobrevibacter* spp., *Mitsuokella multacida, Mitsuokella* spp., *Mucispirillum schaedleri, Odoribacter* spp., *Oscillospira* spp., *Parabacteroides distasonis, Parabacteroides* spp., *Paraprevotella* spp., *Paraprevotellaceae* spp., *Parvimonas* spp., *Pediococcus* spp., *Pediococcus* Other, *Peptococcus* spp., *Peptoniphilus* spp., *Peptostreptococcus anaerobius, Peptostreptococcus* Other, *Phascolarctobacterium* spp., *Prevotella copri, Prevotella* spp., *Prevotella stercorea, Prevotellaceae, Proteus* spp., *Rikenellaceae* spp., *Roseburia faecis, Roseburia* spp., *Ruminococcaceae* Other, *Ruminococcaceae* spp., *Ruminococcus bromii, Ruminococcus gnavus, Ruminococcus* spp., *Ruminococcus* Other, *Ruminococcus torques, Slackia* spp., S24-7 spp., SMB53 spp., *Streptococcus anginosus, Streptococcus luteciae, Streptococcus* spp., *Streptococcus* Other, *Sutterella* spp., *Turicibacter* spp., UC *Bulleidia*, UC *Enterobacteriaceae*, UC *Faecalibacterium*, UC *Parabacteroides*, UC *Pediococcus, Varibaculum* spp., *Veillonella* spp., *Sutterella, Turicibacter*, UC *Clostridiales*, UC *Erysipelotrichaceae*, UC *Ruminococcaceae, Veillonella parvula, Veillonella* spp., *Veillonella dispar*, and *Weissella*.

In the context of the present invention, the term "vaccine" (also referred to as an immunogenic composition) refers to a substance that induces immunity upon inoculation into animals. In some instances, the vaccine of the invention can be used to inducing immunity to one or more bacteria types of the over-represented constituent.

In one embodiment, the vaccine comprises at least one bacterium. For example, in certain embodiments, the vaccine comprises an inactivated or killed bacterium. Inactivated or killed indicates the bacterium has lost the ability to cause disease in mammals but retains an immunogenic property thereof, particularly the ability to generate a specific immune response against one or more antigens of the bacterium. The term inactivated bacterium also includes non-virulent bacterium. Methods for preparing or selecting inactivated bacteria are well known in the art. They include heat-inactivation methods, or chemical inactivation methods. Inactivation may be carried out by exposing the bacterium to a chemical agent such as formalin, formaldehyde, paraformaldehyde, β-propiolactone, ethyleneimine, binary ethyleneimine (BEI), thimerosal, or derivatives thereof. Alternatively, inactivation may be carried out by physical treatments such as heat treatment or sonication. Methods of inactivation are well known to those of skill in the art. The inactivated pathogen may be concentrated by conventional concentration techniques, in particular by ultrafiltration, and/or purified by conventional purification means, in particular using chromatography techniques including but not limited to gel-filtration, ultracentrifugation on a sucrose gradient, or selective precipitations.

In one embodiment, the vaccine comprises an antigen (e.g., a peptide or polypeptide), a nucleic acid encoding an antigen (e.g., an antigen expression vector), a cell expressing or presenting an antigen or cellular component. For example, in certain embodiments, the antigen is an antigen of one or more bacteria associated with the development or progression of a disease or disorder, thereby inducing an immune response against the one or more bacteria.

In one embodiment, the vaccine comprises a mixture that comprises an additional immunostimulatory agent or nucleic acids encoding such an agent. Immunostimulatory agents include but are not limited to an antigen, an immunomodulator, an antigen presenting cell or an adjuvant. An adjuvant refers to a compound that enhances the immune response when administered together (or successively) with the immunological composition. Examples of suitable adjuvants include cholera toxin, *E. coli* heat-labile toxin, *E. coli* enterotoxin, *salmonella* toxin, alum, nanoparticle-based adjuvants, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-1, IL-2, IL-4, IL-5, IL-6, IL-10, IL-12, IL-18, MHC, CD80, and CD86.

Examples of suitable adjuvants and/or immunomodulators include, but are not limited to, complete or incomplete Freund's adjuvant, RIBI (e.g., muramyl dipeptides, etc.), KLH peptide, cholera toxin or a portion thereof, *salmonella* toxin or a portion thereof, *E. coli* heat labile enterotoxin or a portion thereof, *E. coli* enterotoxin or a portion thereof, AB5 toxins or a portion thereof, mineral salts, aluminum salts (e.g., hydroxide, phosphate, Alum, etc.), calcium phosphate, liposomes, virosomes (unilamellar liposomal vehicles, immunostimulating reconstituted influenza virosomes [IRIV]), virus-like particles, cochleates, eurocine (e.g., monoglycerides with fatty acids, etc.), archaeal lipids, ISCOMS (e.g., immunostimulating complexes, structured complex of saponins and lipids, etc.), microparticles (e.g., PLG, etc.), emulsions (e.g., MF59, Montanides, etc.), monophosphoryl lipid (MPL) or synthetic derivatives, N-acetyl-muramyl-L-alanyl-D-isoglutamine (MDP) or a derivative, Detox (MPL+CWS), AS04 (Alum+MPL), AS02 (oil-in-water emulsion+MPL+QS21), AS01 (liposomes+MPL+QS21), OM-174 (e.g., Lipid A derivative, *E. coli*, etc.), OM-triacyl, oligonucleotides (e.g., CpG, etc.), double-stranded RNA (dsRNA), pathogen-associated molecular patterns (PAMPs), TLR ligands (e.g., flagellin, monophosphoryl lipid A, etc.), saponins (e.g., Quils, QS-21, etc.), chitosan, α-galactosylceramide, small-molecule immune potentiators (SMIPs) (e.g., imiquimod, resiquimod [R848], etc.), a cytokine or chemokine (e.g., IL-2, IL-12, GM-CSF, Flt3, etc.), an accessory molecule (e.g., B7.1, etc.), liposomes (e.g., DNPC/Chol, etc.), DC Chol (e.g., lipoidal immunomodulators able to self-organize into liposomes, etc.), nanoparticle-based adjuvants, PLA (polylactic acid) microparticles, PLG (poly[lactide-co-glycolide]) microparticles, Poly(DL-lactide-co-glycolide) microparticles, polystyrene (latex) microparticles, proteosomes (e.g., hydrophobic, proteinaceous, nanoparticles comprised of purified *N. meningitidis* outer membrane proteins, etc.), and 3',5'-Cyclic diguanylic acid (c-di-GMP). Such example adjuvants and/or immunomodulators, as well as others, are understood by those skilled in the art, are readily described in available literature, and are useful in the compositions and methods of the invention.

Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations. In one embodiment, the pharmaceutical carrier is an adjuvant.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine can further comprise a pharmaceutically acceptable excipient. The pharmaceutically acceptable excipient can be functional molecules as vehicles, adjuvants, carriers, or diluents.

The vaccine or pharmaceutical composition can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof.

Passive Immunotherapy

In other embodiments, modification of the altered microbiota having over-represented secretory antibody-coated constituents is achieved by administering to a subject in need thereof a therapeutically effective amount of a passive immunotherapy or passive vaccine, such as by the administration of immunoglobulin (e.g., IgA) against the over-represented constituent, wherein the administered passive vaccine and ensuing immune response diminishes the number or pathogenic effects of at least one type (e.g., genus, species, strain, sub-strain, etc.) of secretory antibody-coated bacteria that is over-represented in the altered microbiota, as compared with a normal microbiota. In some embodiments, the immunoglobulin is administered orally. Alternatively, the immunoglobulin can be administered rectally or by enema. In various embodiments, the at least one type (e.g., genus, species, strain, sub-strain, etc.) of bacteria that is diminished using the methods of the invention includes a Segmented Filamentous Bacteria (SFB) or *Helicobacter flexispira*, or a bacteria from at least one family selected from the group consisting of *Lactobacillus, Helicobacter*, S24-7*, Erysipelotrichaceae* and *Prevotellaceae*. In some embodiments, the bacteria from the family *Prevotellaceae* is a bacteria from the genera of *Paraprevotella* or *Prevotella*. In other embodiments, the secretory antibody-coated constituent of the subject's microbiota associated with the development or progression of an inflammatory disease or disorder in the subject is at least one strain of at least one bacteria selected from *Acidaminococcus* spp., *Actinomyces* spp., *Akkermansia muciniphila, Allobaculum* spp., *Anaerococcus* spp., *Anaerostipes* spp., *Bacteroides* spp., *Bacteroides* Other, *Bacteroides acidifaciens, Bacteroides coprophilus, Bacteroides fragilis, Bacteroides ovatus, Bacteroides uniformis, Barnesiellaceae* spp., *Bifidobacterium adolescentis, Bifidobacterium* Other, *Bifidobacterium* spp., *Bilophila* spp., *Blautia obeum, Blautia producta, Blautia* Other, *Blautia* spp., *Bulleidia* spp., *Catenibacterium* spp., *Citrobacter* spp., *Clostridiaceae* spp., *Clostridiales* Other, *Clostridiales* spp., *Clostridium perfringens, Clostridium* spp., *Clostridium* Other, *Collinsella aerofaciens, Collinsella* spp., *Collinsella stercoris, Coprococcus catus, Coprococcus* spp., *Coriobacteriaceae* spp., *Desulfovibrionaceae* spp., *Dialister* spp., *Dorea formicigenerans, Dorea* spp., *Dorea* Other,

*Eggerthella lenta, Enterobacteriaceae* Other, *Enterobacteriaceae* spp., *Enterococcus* spp., *Erysipelotrichaceae* spp., *Eubacterium biforme, Eubacterium biforme, Eubacterium dolichum, Eubacterium* spp., *Faecalibacterium prausnitzii, Fusobacterium* spp., *Gemellaceae* spp., *Haemophilus parainfluenzae, Haemophilus* Other, *Helicobacter* spp., *Helicobacter Lachnospiraceae* Other, *Lachnospiraceae* spp., *Lactobacillus reuteri, Lactobacillus mucosae, Lactobacillus zeae, Lactobacillus* spp., *Lactobacillaceae* spp., *Lactococcus* spp., *Leuconostocaceae* spp., *Megamonas* spp., *Megasphaera* spp., *Methanobrevibacter* spp., *Mitsuokella multacida, Mitsuokella* spp., *Mucispirillum schaedleri, Odoribacter* spp., *Oscillospira* spp., *Parabacteroides distasonis, Parabacteroides* spp., *Paraprevotella* spp., *Paraprevotellaceae* spp., *Parvimonas* spp., *Pediococcus* spp., *Pediococcus* Other, *Peptococcus* spp., *Peptoniphilus* spp., *Peptostreptococcus anaerobius, Peptostreptococcus* Other, *Phascolarctobacterium* spp., *Prevotella copri, Prevotella* spp., *Prevotella stercorea, Prevotellaceae, Proteus* spp., *Rikenellaceae* spp., *Roseburia faecis, Roseburia* spp., *Ruminococcaceae* Other, *Ruminococcaceae* spp., *Ruminococcus bromii, Ruminococcus gnavus, Ruminococcus* spp., *Ruminococcus* Other, *Ruminococcus torques, Slackia* spp., S24-7 spp., SMB53 spp., *Streptococcus anginosus, Streptococcus luteciae, Streptococcus* spp., *Streptococcus* Other, *Sutterella* spp., *Turicibacter* spp., UC *Bulleidia*, UC *Enterobacteriaceae*, UC *Faecalibacterium*, UC *Parabacteroides*, UC *Pediococcus, Varibaculum* spp., *Veillonella* spp., *Sutterella, Turicibacter*, UC *Clostridiales*, UC *Erysipelotrichaceae*, UC *Ruminococcaceae, Veillonella parvula, Veillonella* spp., *Veillonella dispar*, and *Weissella*.

Antibiotics

In other embodiments, modification of the altered microbiota having over-represented secretory antibody-coated constituents is achieved by administering to a subject in need thereof a therapeutically effective amount of antibiotic composition comprising an effective amount of at least one antibiotic, or a combinations of several types of antibiotics, wherein the administered antibiotic diminishes the number or pathogenic effects of at least one type (e.g., genus, species, strain, sub-strain, etc.) of secretory antibody-coated bacteria that is over-represented in the altered microbiota, as compared with a normal microbiota. In various embodiments, the at least one type (e.g., genus, species, strain, sub-strain, etc.) of bacteria that is diminished using the methods of the invention includes a Segmented Filamentous Bacteria (SFB) or *Helicobacter flexispira*, or a bacteria from at least one family selected from the group consisting of *Lactobacillus, Helicobacter*, S24-7, *Erysipelotrichaceae* and *Prevotellaceae*. In some embodiments, the bacteria from the family *Prevotellaceae* is a bacteria from the genera of *Paraprevotella* or *Prevotella*. In other embodiments, the secretory antibody-coated constituent of the subject's microbiota associated with the development or progression of an inflammatory disease or disorder in the subject is at least one strain of at least one bacteria selected from *Acidaminococcus* spp., *Actinomyces* spp., *Akkermansia muciniphila, Allobaculum* spp., *Anaerococcus* spp., *Anaerostipes* spp., *Bacteroides* spp., *Bacteroides* Other, *Bacteroides acidifaciens, Bacteroides coprophilus, Bacteroides fragilis, Bacteroides ovatus, Bacteroides uniformis, Barnesiellaceae* spp., *Bifidobacterium adolescentis, Bifidobacterium* Other, *Bifidobacterium* spp., *Bilophila* spp., *Blautia obeum, Blautia producta, Blautia* Other, *Blautia* spp., *Bulleidia* spp., *Catenibacterium* spp., *Citrobacter* spp., *Clostridiaceae* spp., *Clostridiales* Other, *Clostridiales* spp., *Clostridium perfringens, Clostridium* spp., *Clostridium* Other, *Collinsella aerofaciens, Collinsella* spp., *Collinsella stercoris, Coprococcus catus, Coprococcus* spp., *Coriobacteriaceae* spp., *Desulfovibrionaceae* spp., *Dialister* spp., *Dorea formicigenerans, Dorea* spp., *Dorea* Other, *Eggerthella lenta, Enterobacteriaceae* Other, *Enterobacteriaceae* spp., *Enterococcus* spp., *Erysipelotrichaceae* spp., *Eubacterium biforme, Eubacterium biforme, Eubacterium dolichum, Eubacterium* spp., *Faecalibacterium prausnitzii, Fusobacterium* spp., *Gemellaceae* spp., *Haemophilus parainfluenzae, Haemophilus* Other, *Helicobacter* spp., *Helicobacter Lachnospiraceae* Other, *Lachnospiraceae* spp., *Lactobacillus reuteri, Lactobacillus mucosae, Lactobacillus zeae, Lactobacillus* spp., *Lactobacillaceae* spp., *Lactococcus* spp., *Leuconostocaceae* spp., *Megamonas* spp., *Megasphaera* spp., *Methanobrevibacter* spp., *Mitsuokella multacida, Mitsuokella* spp., *Mucispirillum schaedleri, Odoribacter* spp., *Oscillospira* spp., *Parabacteroides distasonis, Parabacteroides* spp., *Paraprevotella* spp., *Paraprevotellaceae* spp., *Parvimonas* spp., *Pediococcus* spp., *Pediococcus* Other, *Peptococcus* spp., *Peptoniphilus* spp., *Peptostreptococcus anaerobius, Peptostreptococcus* Other, *Phascolarctobacterium* spp., *Prevotella copri, Prevotella* spp., *Prevotella stercorea, Prevotellaceae, Proteus* spp., *Rikenellaceae* spp., *Roseburia faecis, Roseburia* spp., *Ruminococcaceae* Other, *Ruminococcaceae* spp., *Ruminococcus bromii, Ruminococcus gnavus, Ruminococcus* spp., *Ruminococcus* Other, *Ruminococcus torques, Slackia* spp., S24-7 spp., SMB53 spp., *Streptococcus anginosus, Streptococcus luteciae, Streptococcus* spp., *Streptococcus* Other, *Sutterella* spp., *Turicibacter* spp., UC *Bulleidia*, UC *Enterobacteriaceae*, UC *Faecalibacterium*, UC *Parabacteroides*, UC *Pediococcus, Varibaculum* spp., *Veillonella* spp., *Sutterella, Turicibacter*, UC *Clostridiales*, UC *Erysipelotrichaceae*, UC *Ruminococcaceae, Veillonella parvula, Veillonella* spp., *Veillonella dispar*, and *Weissella*.

The type and dosage of the administered antibiotic will vary widely, depending upon the nature of the inflammatory disease or disorder, the character of subject's altered microbiota, the subject's medical history, the frequency of administration, the manner of administration, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In various embodiments, the administered antibiotic is at least one of lipopeptide, fluoroquinolone, ketolide, cephalosporin, amikacin, gentamicin, kanamycin, neomycin, netilmicin, paromomycin, streptomycin, tobramycin, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime cefluprenam, cefoselis, cefozopran, cefpirome, cefquinome, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, ceftaroline, ceftioxide, cefuracetime, imipenem, primaxin, doripenem, meropenem, ertapenem, flumequine, nalidixic acid, oxolinic acid, piromidic acid pipemidic acid, rosoxacin, ciprofloxacin, enoxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, azithromycin, erythromycin, clarithromycin, dirithromycin, roxithromycin, telithromycin, amoxicillin, ampicillin, bacampicillin, carbenicillin, cloxacillin, dicloxacillin, flucloxacillin, mezlocillin, nafcillin, oxacillin, penicillin g, penicillin v, piperacillin, pivampicillin, pivmecillinam, ticarcillin, sulfamethizole, sulfamethoxazole, sulfisoxazole, trimethoprim-sulfamethoxazole, demeclocycline, doxycycline, minocycline, oxytetracycline, tetracycline, linezolid, clindamycin, metronidazole, vancomycin, vancocin, mycobutin, rifampin, nitrofurantoin, chloramphenicol, or derivatives thereof.

Probiotics

In some embodiments, modification of the altered microbiota is achieved by administering to a subject in need thereof a therapeutically effective amount of a probiotic composition comprising an effective amount of at least one type (e.g., genus, species, strain, sub-strain, etc.) of bacteria, or a combinations of several types of bacteria, wherein the administered bacteria supplements the number of the types of bacteria which are under-represented in the altered microbiota, as compared with a normal microbiota. In some embodiments, the probiotic is a surgical probiotic.

In one embodiment, the invention is a method of treating an inflammatory disease or disorder of a subject in need thereof, including the step of administering to the subject at least one type (e.g., genus, species, strain, sub-strain, etc.) of bacteria, or a combinations of several types of bacteria, that is desired, preferred, neutral, beneficial, and/or under-represented in the subject's microbiota.

In some embodiments, the at least one type of bacteria is at least one bacterium of a first strain of a species of bacteria, wherein the first strain of the species of bacteria does not contribute to the development or progression of disease in the subject, and wherein the species of bacteria comprises at least a second strain of bacteria, and wherein the second strain of the species of bacteria does contribute to the development or progression of the inflammatory disease or disorder.

In some embodiments, the at least one type of bacteria is at least one bacterium of a species of bacteria identified from a healthy subject that does not have the disease. For example, in one embodiment, the species or strain of bacteria is a secretory antibody-bound bacteria identified from a healthy subject. As described herein, administration of secretory antibody-bound bacteria from a healthy subject can treat or prevent an inflammatory disease or disorder.

Bacteria administered according to the methods of the present invention can comprise live bacteria. One or several different types of bacteria can be administered concurrently or sequentially. Such bacteria can be obtained from any source, including being isolated from a microbiota and grown in culture using known techniques.

In certain embodiments, the administered bacteria used in the methods of the invention further comprise a buffering agent. Examples of useful buffering agents include sodium bicarbonate, milk, yogurt, infant formula, and other dairy products.

Administration of a bacterium can be accomplished by any method suitable for introducing the organisms into the desired location. The bacteria can be mixed with a carrier and (for easier delivery to the digestive tract) applied to a liquid or to food. The carrier material should be non-toxic to the bacteria as wells as the subject. Preferably, the carrier contains an ingredient that promotes viability of the bacteria during storage. The formulation can include added ingredients to improve palatability, improve shelf-life, impart nutritional benefits, and the like.

The dosage of the administered bacteria (e.g., probiotic, surgical probiotic) will vary widely, depending upon the nature of the inflammatory disease or disorder, the character of subject's altered microbiota, the subject's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the gastrointestinal tract with the desired bacteria. In some embodiments, the dose ranges from about $10^6$ to about $10^{10}$ CFU per administration. In other embodiments, the dose ranges from about $10^4$ to about $10^6$ CFU per administration.

In certain embodiments, the present invention relates to a method for modifying an altered microbiota comprising administering to a subject in need of such treatment, an effective amount of at least one gastric, esophageal, or intestinal bacterium, or combinations thereof. In a preferred embodiment, the bacteria are administered orally. Alternatively, bacteria can be administered rectally or by enema.

The organisms contemplated for administration to modify the altered microbiota include any of the bacteria identified herein as under-represented in an altered microbiota. One of the organisms contemplated for administration to modify the altered microbiota is at least one *Lactobacillus* spp. In certain embodiments, the bacteria administered in the therapeutic methods of the invention comprise administration of a combination of organisms.

While it is possible to administer a bacteria for therapy as is, it may be preferable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the recipient thereof. Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

Although there are no physical limitations to delivery of the formulations of the present invention, oral delivery is preferred for delivery to the digestive tract because of its ease and convenience, and because oral formulations readily accommodate additional mixtures, such as milk, yogurt, and infant formula. For delivery to colon, bacteria can be also administered rectally or by enema.

In a further embodiment, modification of the altered microbiota is achieved by both administering at least one type (e.g., genus, species, strain, sub-strain, etc.) of bacteria to supplement the numbers of at least one type (e.g., genus, species, strain, sub-strain, etc.) of bacteria that is under-represented in the altered microbiota, and administering at least one antibiotic to diminish the numbers of at least one type (e.g., genus, species, strain, sub-strain, etc.) of bacteria that is over-represented in the altered microbiota.

Methods of Identifying

The methods of the invention are useful for detecting, identifying and determining the absolute number or relative proportions of secretory antibody-coated and uncoated constituents of a subject's microbiota, to determine whether a subject's microbiota is an altered microbiota associated with a disease or disorder, such as an inflammatory disease or disorder. In some embodiments, the methods of the invention combine a flow cytometry-based microbial cell sorting and genetic analyses to detect, to isolate and to identify secretory antibody-coated microbes from the microbiota of a subject. Pathobionts, as well as other disease-causing microbes, present in the microbiota of the of the subject are recognized by the subject's immune system, which triggers an immune response, including antibody production and secretion, directed against the pathobionts, and disease-causing microbes. Thus, in some embodiments of the methods of the invention, specifically binding secretory antibodies (e.g., IgA, IgM) produced by the subject and secreted through the mucosa of the subject, serve as a marker and a means for isolating and identifying putative pathobionts, pathobionts, and other disease-causing bacteria, that are the targets of the subject's immune response. In various embodiments of the methods of the invention, the secretory antibody is IgA (i.e., IgA1, IgA2), or IgM, or any combination thereof. The microbiota of the subject can be any microbiota present on any mucosal surface of subject where antibody is secreted, including the gastrointestinal tract, the respiratory tract, genitourinary tract and mammary gland.

In various embodiments, the present invention relates to the isolation and identification of constituents of the microbiota of a subject that influence the development and progression of a disease or disorder, such as an inflammatory disease and disorder. In one embodiment, the invention relates to compositions and methods for detecting and determining the identity of secretory antibody-coated constituents of a subject's microbiota to determine whether the secretory antibody-coated constituents of a subject's microbiota form an altered microbiota associated with an inflammatory disease or disorder. In various embodiments, the relative proportions of the secretory antibody-coated and uncoated constituents of a subject's microbiota are indicative of an altered microbiota associated with an inflammatory disease or disorder. In some embodiments, the detection and identification of secretory antibody-coated constituents of the microbiota of the subject are used to diagnose the subject as having, or as at risk of developing, an inflammatory disease or disorder. In other embodiments, the detection and identification of secretory antibody-coated constituents of the microbiota of the subject are used to diagnose the subject as having, or as at risk of developing, a recurrence or flare of an inflammatory disease or disorder. In other embodiments, the detection and identification of secretory antibody-coated constituents of the microbiota of the subject are used to diagnose the subject as having, or as likely to have, remission or an inflammatory disease or disorder. In various embodiments, the inflammatory diseases and disorders associated with altered microbiota having secretory antibody-coated constituents include, but are not limited to, at least one of: inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), or non-alcoholic steatohepatitis (NASH).

In other various embodiments, the present invention relates to the isolation and identification of constituents of the microbiota of a subject that are not associated with the development and progression of a disease or disorder, such as an inflammatory disease and disorder. In one embodiment, the invention relates to compositions and methods for detecting and determining the identity of constituents of the subject's microbiota that are not substantially bound by secretory antibodies. In various embodiments, the relative proportions of the low-, or non-secretory antibody-coated constituents of a subject's microbiota are indicative of an altered microbiota associated with an inflammatory disease or disorder.

In one embodiment, the invention is a method for determining the relative proportions of the types of secretory antibody-coated constituents of a subject's microbiota, to identify constituents of a subject's microbiota that are, and are not, associated with the development or progression of an inflammatory disease or disorder. In some embodiments, the detection of particular types of secretory antibody-coated constituents of the subject's microbiota is used to diagnose the subject as having, or as at risk of developing, an inflammatory disease or disorder. In various embodiments, the inflammatory disease or disorder associated with secretory antibody-coated constituents of the subject's microbiota include, but are not limited to, at least one of: inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), and non-alcoholic steatohepatitis (NASH). In some embodiments, the secretory antibody-coated constituent of the subject's microbiota associated with the development or progression of an inflammatory disease or disorder in the subject is a Segmented Filamentous Bacteria (SFB) or *Helicobacter flexispira*. In other embodiments, the secretory antibody-coated constituent of the subject's microbiota associated with the development or progression of an inflammatory disease or disorder in the subject is a bacteria from a family selected from the group consisting of *Lactobacillus, Helicobacter*, S24-7, *Erysipelotrichaceae* and *Prevotellaceae*. In some embodiments, the bacteria from the family *Prevotellaceae* is a bacteria from the genera of *Paraprevotella* or *Prevotella*. In other embodiments, the secretory antibody-coated constituent of the subject's microbiota associated with the development or progression of an inflammatory disease or disorder in the subject is at least one strain of at least one bacteria selected from *Acidaminococcus* spp., *Actinomyces* spp., *Akkermansia muciniphila, Allobaculum* spp., *Anaerococcus* spp., *Anaerostipes* spp., *Bacteroides* spp., *Bacteroides* Other, *Bacteroides acidifaciens, Bacteroides coprophilus, Bacteroides fragilis, Bacteroides ovatus, Bacteroides uniformis, Barnesiellaceae* spp., *Bifidobacterium adolescentis, Bifidobacterium* Other, *Bifidobacterium* spp., *Bilophila* spp., *Blautia obeum, Blautia producta, Blautia* Other, *Blautia* spp., *Bulleidia* spp., *Catenibacterium* spp., *Citrobacter* spp., *Clostridiaceae* spp., *Clostridiales* Other, *Clostridiales* spp., *Clostridium perfringens, Clostridium* spp., *Clostridium* Other, *Collinsella aerofaciens, Collinsella* spp., *Collinsella stercoris, Coprococcus catus, Coprococcus* spp., *Coriobacteriaceae* spp., *Desulfovibrionaceae* spp., *Dialister* spp., *Dorea formicigenerans, Dorea* spp., *Dorea* Other, *Eggerthella lenta, Enterobacteriaceae* Other, *Enterobacteriaceae* spp., *Enterococcus* spp., *Erysipelotrichaceae* spp., *Eubacterium biforme, Eubacterium biforme, Eubacterium dolichum, Eubacterium* spp., *Faecalibacterium prausnitzii, Fusobacterium* spp., *Gemellaceae* spp., *Haemophilus parainfluenzae, Haemophilus* Other, *Helicobacter* spp., *Helicobacter Lachnospiraceae*

Other, *Lachnospiraceae* spp., *Lactobacillus reuteri*, *Lactobacillus mucosae*, *Lactobacillus zeae*, *Lactobacillus* spp., *Lactobacillaceae* spp., *Lactococcus* spp., *Leuconostocaceae* spp., *Megamonas* spp., *Megasphaera* spp., *Methanobrevibacter* spp., *Mitsuokella multacida*, *Mitsuokella* spp., *Mucispirillum schaedleri*, *Odoribacter* spp., *Oscillospira* spp., *Parabacteroides distasonis*, *Parabacteroides* spp., *Paraprevotella* spp., *Paraprevotellaceae* spp., *Parvimonas* spp., *Pediococcus* spp., *Pediococcus* Other, *Peptococcus* spp., *Peptoniphilus* spp., *Peptostreptococcus anaerobius*, *Peptostreptococcus* Other, *Phascolarctobacterium* spp., *Prevotella copri*, *Prevotella* spp., *Prevotella stercorea*, *Prevotellaceae*, *Proteus* spp., *Rikenellaceae* spp., *Roseburia faecis*, *Roseburia* spp., *Ruminococcaceae* Other, *Ruminococcaceae* spp., *Ruminococcus bromii*, *Ruminococcus gnavus*, *Ruminococcus* spp., *Ruminococcus* Other, *Ruminococcus torques*, *Slackia* spp., *S24-7* spp., *SMB53* spp., *Streptococcus anginosus*, *Streptococcus luteciae*, *Streptococcus* spp., *Streptococcus* Other, *Sutterella* spp., *Turicibacter* spp., UC *Bulleidia*, UC *Enterobacteriaceae*, UC *Faecalibacterium*, UC *Parabacteroides*, UC *Pediococcus*, *Varibaculum* spp., *Veillonella* spp., *Sutterella*, *Turicibacter*, UC *Clostridiales*, UC *Erysipelotrichaceae*, UC *Ruminococcaceae*, *Veillonella parvula*, *Veillonella* spp., *Veillonella dispar*, and *Weissella*.

In some embodiments, the invention is a method of identifying the type or types of secretory antibody-bound bacteria present in the microbiota of a subject that contribute to the development or progression of an inflammatory disease or disorder in the subject. In other embodiments, the invention is a method of diagnosing an inflammatory disease or disorder in a subject by identifying a type or types of secretory antibody-bound bacteria in the microbiota of the subject that contribute to the development or progression of an inflammatory disease or disorder.

In some embodiments, the invention is a method of identifying the type or types of secretory antibody-bound bacteria present in the microbiota of a subject that does not contribute to the development or progression of an inflammatory disease or disorder in the subject. For example, in one embodiment, the method comprises identifying the type or types of secretory antibody-bound bacteria present in a healthy subject not having an inflammatory disease or disorder. In certain embodiments, the identified type or types of secretory antibody-bound bacteria present in a healthy subject may be used to treat a subject having an inflammatory disease or disorder. In certain embodiments, the identified type or types of secretory antibody-bound bacteria present in a healthy subject may be used to prevent the development of an inflammatory disease or disorder in a subject at risk.

Specific alterations in a subject's microbiota, including the presence of secretory antibody-coated constituents, can be detected using various methods, including without limitation quantitative PCR or high-throughput sequencing methods which detect relative proportions of microbial genetic markers in a total heterogeneous microbial population. In some embodiments, the microbial genetic marker is a bacterial genetic marker. In particular embodiments, the bacterial genetic marker is at least some portion of the 16S rRNA. In some embodiments, the relative proportion of particular constituent bacterial phyla, classes, orders, families, genera, and species present in the microbiota of a subject is determined. In other embodiments, the relative proportion of secretory antibody-coated and/or uncoated constituent bacterial phyla, classes, orders, families, genera, and species present in the microbiota of a subject is determined. In some embodiments, the relative proportion of particular constituent bacterial phyla, classes, orders, families, genera, and species present in the microbiota of a subject is determined and compared with that of a comparator normal microbiota. In other embodiments, the relative proportion of secretory antibody-coated and/or uncoated constituent bacterial phyla, classes, orders, families, genera, and species present in the microbiota of a subject is determined and compared with that of a comparator normal microbiota. In various embodiments, the comparator normal microbiota is, by way of non-limiting examples, a microbiota of a subject known to be free of an inflammatory disorder, or a historical norm, or a typical microbiota of the population of which the subject is a member.

In one embodiment, the method of the invention is a diagnostic assay for diagnosing an inflammatory disease or disorder associated with an altered microbiota in a subject in need thereof, by determining the absolute or relative abundance of particular types of secretory antibody-coated constituents of the subject's microbiota present in a biological sample derived from the subject. In some embodiments, the subject is diagnosed as having an inflammatory disease or disorder when particular types of secretory antibody-coated bacteria are determined to be present in the biological sample derived from the subject with increased relative abundance. In some embodiments, the secretory antibody-coated bacteria determined to be present in the biological sample derived from the subject with increased relative abundance is a Segmented Filamentous Bacteria (SFB) or *Helicobacter flexispira*. In some embodiments, the secretory antibody-coated bacteria determined to be present in the biological sample derived from the subject with increased relative abundance is a bacteria from a family selected from the group consisting of *Lactobacillus*, *Helicobacter*, S24-7, *Erysipelotrichaceae* and *Prevotellaceae*. In some embodiments, the bacteria from the family *Prevotellaceae* is a bacteria from the genera of *Paraprevotella* or *Prevotella*. In other embodiments, the secretory antibody-coated constituent of the subject's microbiota associated with the development or progression of an inflammatory disease or disorder in the subject is at least one strain of at least one bacteria selected from *Acidaminococcus* spp., *Actinomyces* spp., *Akkermansia muciniphila*, *Allobaculum* spp., *Anaerococcus* spp., *Anaerostipes* spp., *Bacteroides* spp., *Bacteroides* Other, *Bacteroides acidifaciens*, *Bacteroides coprophilus*, *Bacteroides fragilis*, *Bacteroides ovatus*, *Bacteroides uniformis*, *Barnesiellaceae* spp., *Bifidobacterium adolescentis*, *Bifidobacterium* Other, *Bifidobacterium* spp., *Bilophila* spp., *Blautia obeum*, *Blautia producta*, *Blautia* Other, *Blautia* spp., *Bulleidia* spp., *Catenibacterium* spp., *Citrobacter* spp., *Clostridiaceae* spp., *Clostridiales* Other, *Clostridiales* spp., *Clostridium perfringens*, *Clostridium* spp., *Clostridium* Other, *Collinsella aerofaciens*, *Collinsella* spp., *Collinsella stercoris*, *Coprococcus catus*, *Coprococcus* spp., *Coriobacteriaceae* spp., *Desulfovibrionaceae* spp., *Dialister* spp., *Dorea formicigenerans*, *Dorea* spp., *Dorea* Other, *Eggerthella lenta*, *Enterobacteriaceae* Other, *Enterobacteriaceae* spp., *Enterococcus* spp., *Erysipelotrichaceae* spp., *Eubacterium biforme*, *Eubacterium biforme*, *Eubacterium dolichum*, *Eubacterium* spp., *Faecalibacterium prausnitzii*, *Fusobacterium* spp., *Gemellaceae* spp., *Haemophilus parainfluenzae*, *Haemophilus* Other, *Helicobacter* spp., *Helicobacter Lachnospiraceae* Other, *Lachnospiraceae* spp., *Lactobacillus reuteri*, *Lactobacillus mucosae*, *Lactobacillus zeae*, *Lactobacillus* spp., *Lactobacillaceae* spp., *Lactococcus* spp., *Leuconostocaceae* spp., *Megamonas* spp., *Megasphaera* spp., *Methanobrevibacter* spp., *Mitsuokella*

*multacida, Mitsuokella* spp., *Mucispirillum schaedleri, Odoribacter* spp., *Oscillospira* spp., *Parabacteroides distasonis, Parabacteroides* spp., *Paraprevotella* spp., *Paraprevotellaceae* spp., *Parvimonas* spp., *Pediococcus* spp., *Pediococcus* Other, *Peptococcus* spp., *Peptoniphilus* spp., *Peptostreptococcus anaerobius, Peptostreptococcus* Other, *Phascolarctobacterium* spp., *Prevotella copri, Prevotella* spp., *Prevotella stercorea, Prevotellaceae, Proteus* spp., *Rikenellaceae* spp., *Roseburia faecis, Roseburia* spp., *Ruminococcaceae* Other, *Ruminococcaceae* spp., *Ruminococcus bromii, Ruminococcus gnavus, Ruminococcus* spp., *Ruminococcus* Other, *Ruminococcus torques, Slackia* spp., *S24-7* spp., *SMB53* spp., *Streptococcus anginosus, Streptococcus luteciae, Streptococcus* spp., *Streptococcus* Other, *Sutterella* spp., *Turicibacter* spp., UC *Bulleidia*, UC *Enterobacteriaceae*, UC *Faecalibacterium*, UC *Parabacteroides*, UC *Pediococcus, Varibaculum* spp., *Veillonella* spp., *Sutterella, Turicibacter*, UC *Clostridiales*, UC *Erysipelotrichaceae*, UC *Ruminococcaceae, Veillonella parvula, Veillonella* spp., *Veillonella dispar*, and *Weissella*.

The results of the diagnostic assay can be used alone, or in combination with other information from the subject, or from the biological sample derived from the subject.

In the assay methods of the invention, a test biological sample from a subject is assessed for the absolute or relative abundance of secretory antibody-coated and uncoated constituents of the microbiota. The test biological sample can be an in vitro sample or an in vivo sample. In various embodiments, the subject is a human subject, and may be of any race, sex and age. Representative subjects include those who are suspected of having an altered microbiota associated with an inflammatory disease or disorder, those who have been diagnosed with an altered microbiota associated with an inflammatory disease or disorder, those whose have an altered microbiota associated with an inflammatory disease or disorder, those who have had an altered microbiota associated with an inflammatory disease or disorder, those who at risk of a recurrence of an altered microbiota associated with an inflammatory disease or disorder, those who at risk of a flare of an altered microbiota associated with an inflammatory disease or disorder, and those who are at risk of developing an altered microbiota associated with an inflammatory disease or disorder.

In some embodiments, the test sample is prepared from a biological sample obtained from the subject. In some instances, a heterogeneous population of microbes will be present in the biological samples. Enrichment of a microbial population for microbes (e.g., bacteria) bound by secretory antibody (e.g., IgA, IgM) may be accomplished using separation technique. For example, microbes of interest may be enriched by separation the microbes of interest from the initial population using affinity separation techniques. Techniques for affinity separation may include magnetic separation using magnetic beads conjugated with an affinity reagent, affinity chromatography, "panning" with an affinity reagent attached to a solid matrix, e.g. plate, or other convenient technique. Other techniques providing separation include fluorescence activated cell sorting, which can have varying degrees of sophistication, such as multiple color channels, low angle and obtuse light scattering detecting channels, impedance channels, etc. One example of an affinity reagent useful in the methods of the invention is an antibody, such as anti-species antibody or anti-isotype (e.g., anti-IgA, anti-IgM) antibody. The details of the preparation of such antibodies and their suitability for use as affinity reagents are well-known to those skilled in the art. In some embodiments, labeled antibodies are used as affinity reagents. Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type.

In various embodiments, the initial population of microbes is contacted with one or more affinity reagent(s) and incubated for a period of time sufficient to permit the affinity reagent to specifically bind to its target. The microbes in the contacted population that become labeled by the affinity reagent are selected for by any convenient affinity separation technique, e.g. as described elsewhere herein or as known in the art. Compositions highly enriched for a microbe of interest (e.g., secretory antibody-bound bacteria) are achieved in this manner. The affinity enriched microbes will be about 70%, about 75%, about 80%, about 85% about 90%, about 95% or more of the composition. In other words, the enriched composition can be a substantially pure composition of the microbes of interest.

In one embodiment, the test sample is a sample containing at least a fragment of a bacterial nucleic acid. The term, "fragment," as used herein, indicates that the portion of a nucleic acid (e.g., DNA, RNA) that is sufficient to identify it as comprising a bacterial nucleic acid.

In some embodiments, the test sample is prepared from a biological sample obtained from the subject. The biological sample can be a sample from any source which contains a bacterial nucleic acid (e.g., DNA, RNA), such as a bodily fluid or fecal sample, or a combination thereof. A biological sample can be obtained by any suitable method. In some embodiments, a biological sample containing bacterial DNA is used. In other embodiments, a biological sample containing bacterial RNA is used. The biological sample can be used as the test sample; alternatively, the biological sample can be processed to enhance access to nucleic acids, or copies of nucleic acids, and the processed biological sample can then be used as the test sample. For example, in various embodiments, nucleic acid is prepared from a biological sample, for use in the methods. Alternatively or in addition, if desired, an amplification method can be used to amplify nucleic acids comprising all or a fragment of an RNA or DNA in a biological sample, for use as the test sample in the assessment of the presence, absence and proportion of particular types of bacteria present in the sample.

In some embodiments, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of nucleic acid from a particular type of bacteria can be determined by hybridization of nucleic acid to a nucleic acid probe. A "nucleic acid probe," as used herein, can be a DNA probe or an RNA probe.

The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target RNA or DNA. The hybridization sample is maintained under conditions which are sufficient to allow specific hybridization of the nucleic acid probe to RNA or DNA. Specific hybridization can be performed under high stringency conditions or moderate stringency conditions, as appropriate. In a preferred embodiment, the hybridization conditions for specific hybridization are high stringency. More than one nucleic acid probe can also be used concurrently in this method. Specific hybridization of any one of the nucleic acid probes is indicative of the presence of the particular type of bacteria of interest, as described herein.

In Northern analysis (see Current Protocols in Molecular Biology, Ausubel, F. et al., eds., John Wiley & Sons, supra), the hybridization methods described above are used to identify the presence of a sequence of interest in an RNA, such as unprocessed, partially processed or fully processed rRNA. For Northern analysis, a test sample comprising RNA is prepared from a biological sample from the subject by appropriate means. Specific hybridization of a nucleic acid probe, as described above, to RNA from the biological sample is indicative of the presence of the particular type of bacteria of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a particular bacterial nucleic acid sequence. Hybridization of the PNA probe to a nucleic acid sequence is indicative of the particular type of bacteria of interest.

Direct sequence analysis can also be used to detect a bacterial nucleic acid of interest. A sample comprising DNA or RNA can be used, and PCR or other appropriate methods can be used to amplify all or a fragment of the nucleic acid, and/or its flanking sequences, if desired. The bacterial nucleic acid, or a fragment thereof, is determined, using standard methods.

In another embodiment, arrays of oligonucleotide probes that are complementary to target microbial nucleic acid sequences can be used to detect and identify microbial nucleic acids. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and scanned for particular bacterial nucleic acids. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target bacterial nucleic acid sequence is amplified by well-known amplification techniques, e.g., PCR. Typically, this involves the use of primer sequences that are complementary to the target sequence. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Other methods of nucleic acid analysis can be used to detect microbial nucleic acids of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (1981, Sheffield et al., Proc. Natl. Acad. Sci. USA 86:232-236), mobility shift analysis (1989, Orita et al., Proc. Natl. Acad. Sci. USA 86:2766-2770; 1987, Rosenbaum and Reissner, Biophys. Chem. 265:1275; 1991, Keen et al., Trends Genet. 7:5); restriction enzyme analysis (1978, Flavell et al., Cell 15:25; 1981, Geever, et al., Proc. Natl. Acad. Sci. USA 78:5081); heteroduplex analysis; chemical mismatch cleavage (CMC) (1985, Cotton et al., Proc. Natl. Acad. Sci. USA 85:4397-4401); RNase protection assays (1985, Myers, et al., Science 230:1242); use of polypeptides which recognize nucleotide mismatches, such as *E. coli* mutS protein (see, for example, U.S. Pat. No. 5,459,039); Luminex xMAP™ technology; high-throughput sequencing (HTS) (2011, Gundry and Vijg, Mutat Res, doi:10.1016/j.mrfmmm.2011.10.001); next-generation sequencing (NGS) (2009, Voelkerding et al., Clinical Chemistry 55:641-658; 2011, Su et al., Expert Rev Mol Diagn. 11:333-343; 2011, Ji and Myllykangas, Biotechnol Genet Eng Rev 27:135-158); ion semiconductor sequencing (2011, Rusk, Nature Methods doi:10.1038/nmeth.f.330; 2011, Rothberg et al., Nature 475:348-352) and/or allele-specific PCR, for example. These and other methods can be used to identify the presence of one or more microbial nucleic acids of interest, in a biological sample derived from a subject. In various embodiments of the invention, the methods of assessing a biological sample for the presence or absence of a particular nucleic acid sequence, as described herein, are used to detect, identify or quantify particular constituents of a subject's microbiota, and to aid in the diagnosis of an altered microbiota associated with an inflammatory disease or disorder in a subject in need thereof.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. Nucleic acid herein refers to RNA, including mRNA, and DNA, including genomic DNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a fresh or fixed biological sample.

Routine methods also can be used to extract DNA from a biological sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

There are many methods known in the art for the detection of specific nucleic acid sequences and new methods are continually reported. A great majority of the known specific nucleic acid detection methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, preferably at least 15 nucleotides, more preferably at least 25 nucleotides, having a sequence complementary to a desired region of the target nucleic acid of interest is hybridized in a sample, subjected to depolymerizing conditions, and the sample is treated with an ATP/luciferase system, which will luminesce if the nucleic sequence is present. In quantitative Southern blotting, levels of the target nucleic acid can be determined.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. Most preferably the detection of the duplex is done using at least one primer directed to the target nucleic acid. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

The expression "specifically hybridizing in stringent conditions" refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. Preferably, the Tm for the amplification step is in the range of about 59° C. to about 72° C. Most preferably, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1997, eds Current Protocols in Molecular Biology).

In a preferred embodiment, the process for determining the quantitative and qualitative profile according to the present invention is characterized in that the amplifications are real-time amplifications performed using a labeled probe, preferably a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a target bacterial nucleic acid, and more particularly the primer includes 12 or more contiguous nucleotides substantially complementary to the sequence flanking the nucleic acid sequence of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence. In another aspect, the length of the primer can vary in length, preferably about 15 to 28 nucleotides in length (e.g., 16, 17, 18, 19, 20, 21, 22, 23, 24, 25, 26, or 27 nucleotides in length).

The present invention also pertains to kits useful in the methods of the invention. Such kits comprise components useful in any of the methods described herein, including for example, hybridization probes or primers (e.g., labeled probes or primers), reagents for detection of labeled molecules, means for amplification of nucleic acids, means for analyzing a nucleic acid sequence, and instructional materials. For example, in one embodiment, the kit comprises components useful for analysis of a bacterial nucleic acid of interest present in a biological sample obtained from a subject. In a preferred embodiment of the invention, the kit comprises components for detecting one or more of the bacterial nucleic acids of interest present in a biological sample derived from a subject.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Immunoglobulin A Coating Identifies Colitogenic Bacteria in Inflammatory Bowel Disease The results presented herein are based on the application of flow cytometry-based bacterial cell sorting and 16S sequencing to characterize taxa-specific coating of the intestinal microbiota with immunoglobulin A (IgA-SEQ) and show that high IgA-coating uniquely identifies colitogenic intestinal bacteria in a mouse model of microbiota-driven colitis (see also Palm et al., 2014, Cell). IgA-SEQ and extensive anaerobic culturing of fecal bacteria from IBD patients was used to create personalized disease-associated gut microbiota culture collections with pre-defined levels of IgA coating. Using these collections, intestinal bacteria selected on the basis of high coating with IgA was found to confer dramatic susceptibility to colitis in germ-free mice. These studies demonstrate that IgA-coating identifies inflammatory commensals that preferentially drive intestinal disease. Targeted elimination of such bacteria may reduce, reverse, or even prevent disease development.

The materials and methods used in these experiments are now described.

Animals

Asc-/-, Rag2-/-, and Tcrb-/-; Tcrd-/- mice were bred and maintained at the Yale School of Medicine and all treatments were in accordance with Yale Animal Care and Use Committee guidelines. Mice were strictly maintained under SPF conditions with consistent monitoring for and exclusion of viral, fungal and bacterial pathogens, as well as helminths and ectoparasites. Wild type C57Bl/6 mice were from the National Cancer Institute (NCI), and germ-free C57Bl/6 mice were purchased from the University of Michigan and the University of North Carolina germ-free facilities. Germ-free mice were singly housed, and age and sex matched mice were used for all studies.

Inflammasome-Mediated Intestinal Dysbiosis

Intestinal dysbiosis was induced by co-housing two wild type C57Bl/6 mice from NCI with two Asc-/- mice for at least 6 weeks.

DSS Colitis

SPF and SPF$^{dys}$ mice were treated with 2% Dextran Sodium Sulfate (MP Biomedicals) in the drinking water ad libitum for 7 days to induce colitis. Weight was measured daily for 14 days. Gnotobiotic mice were treated with filter sterilized 2.5% DSS in the drinking water ad libitum for 6 days before end-point euthanasia.

ELISA

Pre-sort, IgA+ and IgA− fractions (after MACS sorting) were probed for IgA by ELISA (Coating: MP Biomedicals 55478, Detection: Sigma B2766).

Fecal IgA Flow Cytometry and Sorting of IgA+ and IgA− Bacteria

Fecal homogenates were stained with PE-conjugated Anti-Mouse IgA (eBioscience clone mA-6E1) or PE-conjugated Anti-Human IgA (Miltenyi Biotec clone IS11-8E10) prior to flow cytometric analysis or MACS and FACS sorting. Fecal pellets collected directly from two co-housed mice or ~100 mg of frozen human fecal material were placed in Fast Prep Lysing Matrix D tubes containing ceramic beads (MP Biomedicals) and incubated in 1 mL Phosphate Buffered Saline (PBS) per 100 mg fecal material on ice for 1 hour. Fecal pellets were homogenized by bead beating for 5 seconds (Minibeadbeater; Biospec) and then centrifuged (50×g, 15 min, 4° C.) to remove large particles. Fecal bacteria in the supernatants were removed (100 µl/sample), washed with 1 mL PBS containing 1% (w/v) Bovine Serum Albumin (BSA, American Bioanalytical; staining buffer) and centrifuged for 5 min (8,000×g, 4° C.) before resuspension in 1 mL staining buffer. A sample of this bacterial suspension (20 µl) was saved as the Pre-sort sample for 16S sequencing analysis. After an additional wash, bacterial pellets were resuspended in 100 µl blocking buffer (staining buffer containing 20% Normal Rat Serum for mouse samples or 20% Normal Mouse Serum for human samples, both from Jackson ImmunoResearch), incubated for 20 min on ice, and then stained with 100 μl staining buffer containing PE-conjugated Anti-Mouse IgA (1:12.5; eBioscience clone mA-6E1) or PE-conjugated Anti-Human IgA (1:10; Miltenyi Biotec clone IS11-8E10) for 30 minutes on ice. Samples were then washed 3 times with 1 mL staining buffer before flow cytometric analysis or cell separation.

Anti-IgA stained fecal bacteria were incubated in 1 ml staining buffer containing 50 μl Anti-PE Magnetic Activated Cell Sorting (MACS) beads (Miltenyi Biotec) (15 min at 4° C.), washed twice with 1 ml Staining Buffer (10,000×g, 5 min, 4° C.), and then sorted by MACS (Possel_s program on an AutoMACS pro; Miltenyi). After MACS separation, 50 μl of the negative fraction was collected for 16S sequencing analysis (IgA negative fraction). The positive fraction was then further purified via Fluorescence Activated Cell Sorting (FACSAria; BD Biosciences). For each sample, 2 million IgA-positive bacteria were collected, pelleted (10,000×g, 5 min, 4° C.), and frozen along with the Pre-sort and IgA-negative samples at −80° C. for future use.

16S rRNA Gene Sequencing, Bacterial Genome Sequencing and Statistical Analyses 16S rRNA sequencing of the V4 region and bacterial genome sequencing were performed on an Illumina miSeq using barcoded primers. Microbial diversity and statistical analyses were performed with QIIME, the Vegan package for R and LEfSe (Caporaso et al., 2010, Nat Methods 7:335-336; Segata et al., 2011, Genome Biol 12:R60). All bacterial samples were suspended in 400 μl staining buffer before adding 250 μl 0.1 mm zirconia/silica beads (Biospec), 300 μl Lysis buffer (200 mM NaCl, 200 mM Tris, 20 mM EDTA, pH 8), 200 μl 20% SDS and 500 μl phenol:chloroform:isoamylalcohol (25:24:1, pH 7.9; Sigma). Samples were chilled on ice for 4 min and then homogenized by beat beating (2 min bead beating, 2 min on ice, 2 min bead beating). After centrifugation (6000×g, 4° C.), the aqueous phase was transferred to a Phase Lock Gel tube (Light; 5 PRIME), an equal volume of phenol:chloroform:isoamylalcohol was added, and samples were mixed by inversion and then centrifuged for 3 min (16,100×g, room temperature). The DNA was then precipitated by adding 1/10 volume of 3M NaOAc (pH5.5) and 1 volume Isopropanol to the aqueous phase before incubation at −20° C. overnight. Precipitated DNA was pelleted (20 min, 16,100×g, 4° C.), washed with 500 μl 100% EtOH (3 min, 16,100×g, 4° C.), dried (miVac GeneVac 15 min, no heat, Auto Run setting), and resuspended in 100 μl TE buffer (pH 7; 50° C. for 30 min). The DNA was then treated with 35 U/ml RNase A (Qiagen) before purification (QIAquick PCR purification; Qiagen), and elution in 40 μl Elution Buffer. The V4 region of 16S ribosomal RNA was then PCR amplified (28 cycles; primer pair F515/R806) in triplicate (10 μl purified DNA per reaction; Phusion polymerase, New England Bioscience) (Caporaso et al., 2012, ISME J 6:1621-1624; Caporaso et al., 2011, P Natl Acad Sci USA 108(Suppl 1):4516-4522). After amplification, PCR triplicates were pooled, purified (MinElute, Qiagen), and resuspended in 20 μl $H_2O$. PCR products were then quantified with Picogreen (Invitrogen) and pooled at a final concentration of 10 nM before sequencing on a miSeq sequencer (Illumina, 2×250 bp paired-end reads, up to 200 samples per sequencing run)

Paired end reads were assembled with a novel pipeline that uses PANDA-seq (Masella et al., 2012, BMC Bioinformatics 13:31) and assigns consensus Q scores to the assembled reads (P.D. and A.L.G., manuscript in preparation). Microbial diversity was analyzed with the Quantitative Insights Into Microbial Ecology (QIIME version 1.7) analysis suite. Reads were demultiplexed and quality filtered with a Q-score cutoff of 30. The open-reference OTU picking workflow in QIIME and the Greengenes reference database were used to cluster the reads into 97% identity Operational Taxonomic Units (OTUs). The Ribosomal Database Project classifier (RDP) and the May 2013 Greengenes taxonomy were used to assign taxonomy to representative OTUs (Caporaso et al., 2010, Nat Methods 7:335-336; Lozupone and Knight, 2005, Appl Environ Microb 71:8228-8235; Wang et al., 2007, Appl Environ Microb 73:5261-5267). OTUs of less than 0.01% relative abundance, and contaminating OTUs that were also found after sequencing of 16S amplicons from PCR samples without template DNA, were filtered from OTU tables. Filtered OTU tables were rarefied to a depth of 5000 sequences per sample for all further analyses.

QIIME and the Vegan package for R (version 2.1-21) were used for all microbial ecology analyses (beta diversity, PCoA, PERMANOVA/adonis) (Caporaso et al., 2010, Nat Methods 7:335-336). The Linear Discriminant Analysis Effect Size (LEfSe) Galaxy module (http://huttenhower.sph.harvard.edu/galaxy/) was used for additional statistical analyses (Segata et al., 2011, Genome Biol 12:R60). Wilcoxon rank-sum tests were performed using R or Prism (Graphpad Software). Taxa that were undetectable in both the IgA+ and IgA− fractions in a given sample were considered not present and were assigned as missing-values for Wilcoxon rank-sum tests. As LEfSe cannot handle missing values, these missing-values were replaced with zeros for all LEfSe analyses. To allow for the calculation of ICI scores for taxa that were undetectable in the IgA− fraction but detected in the IgA+ fraction, and which are therefore highly-coated, zeroes in the negative fraction were replaced with a relative abundance of 0.0002, which is the limit of detection (1 sequence in 5000). The results presented for mice are combined from at least 4 independent experiments.

Genomic DNA for whole genome bacterial sequencing was isolated using a QIAmp DNA isolation kit (Qiagen). A Nextera XT kit (Illumina) was used to prepare barcoded genomic DNA libraries, and paired-end (2×300) sequencing was performed on a MiSeq (Illumina). Sequences were assembled into contigs with the SPAdes genome assembler 3.0 (Bankevich et al., 2012, J Comput Biol 19:455-477) on Basespace (Illumina) and aligned with progressive Mauve (Darling et al., 2004, Genome Res 14:1394-1403).

Human Fecal Samples

The human study protocol was approved by the Institutional Review Board (Protocol No. 10-1047) of the Icahn Medical School at Mount Sinai, N.Y. The healthy subjects were recruited through the Mount Sinai Biobank or an advertisement. Fresh fecal samples were collected at home, stored at −20° C. in an insulated foam shipper, mailed to Mount Sinai overnight and then stored at −80° C. for further analysis. A short questionnaire was also administrated to collect participants' health information. Informed consent was obtained from all subjects.

Culturing of Human Fecal Bacteria and Generation of Personalized Microbiota Culture Collections Culture methods were essentially as in Goodman et al. (Goodman et al., 2011, P Natl Acad Sci USA 108:6252-6257) with minor modifications. Briefly, serial dilutions of fecal material from 11 IBD patients were plated on three types of media: CDC Anaerobe 5% Sheep Blood Agar with or without Kanamycin and Vancomycin (BD Bioscience), and Gut Microbiota Medium (GMM) Agar. 100 to 200 colonies per patient were picked and cultured individually in GMM for 5 days to establish Culture Collections.

Assembly of IgA+ and IgA− Consortia and Colonization of Germ-Free Mice

Members of the IgA+ and IgA− consortia were selected from our IBD microbiota culture collections based on ICI scores determined by IgA-SEQ. The criteria for selecting the members of these consortia were as follows: Strains comprising the IgA+ consortium were selected based on high coating in the patient from whom they were isolated (ICI>10), and were rarely or never highly coated in healthy controls; in other words, they were selected to represent bacteria that are uniquely or preferentially highly coated in IBD. Strains comprising the IgA− consortium were selected based on low coating (ICI<1) in the patient from whom they were isolated and were rarely or never highly coated in IBD patients or controls. Bacterial strains that met these criteria were cultured in GMM for 4 days before mixing to form consortia. Singly housed germ-free C57Bl/6 mice were colonized with 100 µl of the appropriate consortium by oral gavage.

Fluorescence In Situ Hybridization 16S rRNA FISH was performed with a universal bacterial probe (EUB388; 5'G*CTGCCTCCCGTAGGAGT-3'[Cy5]) on sections fixed with Carnoy's solution to preserve the mucus layer as described previously (Canny et al., 2006, Method Mol Cell Biol 341:17-35).

Histology

Colons were fixed in Bouin's solution and embedded in paraffin. Sections were stained with hematoxylin and eosin and scored in a blinded manner by a trained pathologist.

Monocolonization with B. fragilis Isolates

Germ-free C57Bl/6 mice were monocolonized with B. fragilis strains by oral gavage. Mice were treated with 2.5% DSS in the drinking water starting at 5 days after colonization. Monocolonization was confirmed by 16S sequencing of feces.

The results of the experiments are now described.

IgA-SEQ Identifies Highly IgA Coated Members of the Intestinal Microbiota

Figures 1A, 1B, 1C, 1D:
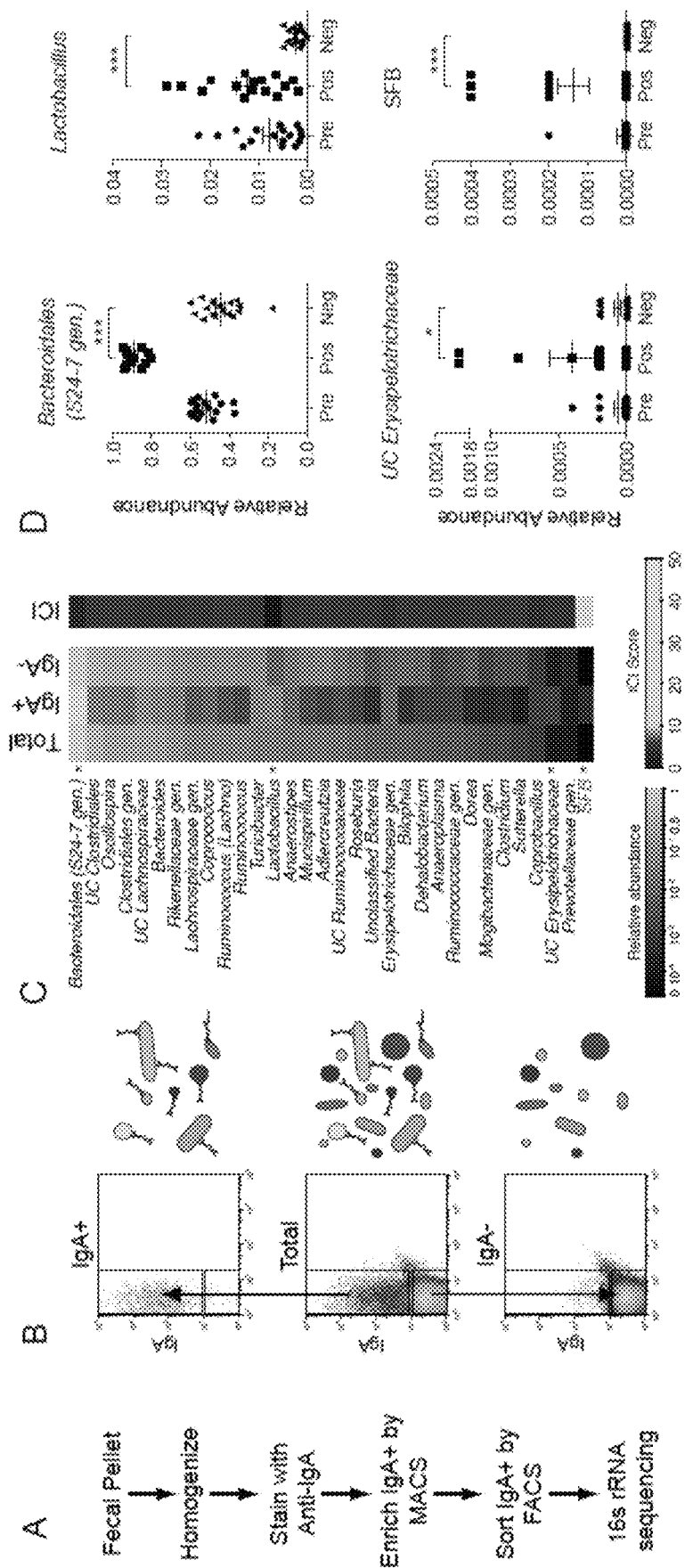
FIGS. 1A-1D, depicts the results of experiments demonstrating that IgA-based sorting and 16S sequencing of fecal bacteria from specific pathogen free (SPF) mice.

To measure taxa-specific IgA coating in an unbiased and comprehensive manner, an approach was devised that combines antibody-based bacterial cell sorting and 16S ribosomal RNA (rRNA) gene sequencing to isolate and identify IgA coated bacteria from fecal material (IgA-SEQ, FIG. 1A). First, fecal bacteria from specific pathogen free (SPF) mice were stained for IgA and it was confirmed that only a fraction of intestinal bacteria are measurably IgA coated, as determined by flow cytometry (7.4%±2.2; FIG. 6A-FIG. 6C) (Kawamoto et al., 2012, Science 336:485-489; Tsuruta et al., 2009, FEMS Immunol Med Mic 56:185-189; van der Waaij et al., 1994, Cytometry 16:270-279); importantly, intestinal bacteria from recombination activating gene 2 (Rag2)-deficient mice, which cannot produce antibodies, showed minimal staining for IgA (0.5%±0.3). Highly IgA coated (IgA+) and non-coated (IgA−) bacteria were subsequently isolated using a combination of magnetic activated cell sorting (MACS) and fluorescence activated cell sorting (FACS). The specificity and efficacy of the sorting was confirmed by reanalyzing sorted fractions via flow cytometry (FIG. 1B and FIG. 6E) and ELISA (FIG. 6F). After 16S rRNA gene sequencing, microbial compositions were compared and visualized using Principal Coordinates Analysis (PCoA) of weighted UniFrac distances, which revealed that, rather than comprising a random sampling of all intestinal bacteria, IgA+ bacteria represent a distinct sub-community within the intestinal microbiota (P<0.05, PERMANOVA) (FIG. 6G and FIG. 6H). Importantly, as was observed in other recent studies using FACS to sort fecal bacteria (Ben-Amor et al., 2005, Appl Environ Microb 71:4679-4689; Maurice et al., 2013, Cell 152:39-50; Peris-Bondia et al., 2011, PLoS One 6:e22448), sorting itself did not artificially alter microbial composition (P>0.05, PERMANOVA). These data demonstrate that IgA coating of the intestinal microbiota is selective across microbial taxa, and show that IgA coated bacteria represent a taxonomically distinct subset of intestinal bacteria in mice.

To identify which specific bacterial taxa were highly coated with IgA, the relative abundance of bacterial genera in total, IgA+ and IgA− bacterial fractions isolated from the feces of SPF mice was examined (FIG. 1C, FIG. 1D, FIG. 6I, and Table 1). To quantify and compare relative levels of IgA coating between taxa, an IgA Coating Index (ICI) was calculated for each individual bacterial taxon as follows: ICI=relative abundance (IgA+)/relative abundance (IgA−). Taxonomic abundance was then compared using the Wilcoxon rank-sum test and Linear Discriminant Analysis Effect Size (LEfSe; (Segata et al., 2011, Genome Biol 12:R60)) to determine which taxa were enriched in either the IgA+ or IgA− fractions (FIG. 6J and Table 1). These analyses revealed that only four genera were significantly enriched in the IgA+ fraction in SPF mice ('significantly coated'; P<0.05): an unclassified genus of the family S24-7 from the order Bacteroidales, Lactobacillus, SFB, and an unclassified Erysipelotrichaceae (FIG. 1C and FIG. 1D). Among these bacteria, only SFB was significantly enriched in the IgA+ fraction and showed an ICI score greater than 10, which was defined as 'highly coated' (P<0.05; ICI>10). In addition, 22 taxa were significantly enriched in the IgA− fraction ('low- or non-coated'; P<0.05), while the remaining taxa were neither enriched nor depleted by IgA-based separation.

TABLE 1

| Taxa | Average ICI score | P value |
|---|---|---|
| Bacteroidales (S24-7 gen.) | 1.995277226 | 6.75E−07 |
| UC Clostridiales | 0.079145127 | 6.72E−07 |
| Oscillospira | 0.10337211 | 6.72E−07 |
| Clostridiales gen. | 0.1022536 | 6.74E−07 |
| UC Lachnospiraceae | 0.329611522 | 2.04E−06 |
| Bacteroides | 0.255545029 | 8.52E−06 |
| Rikenellaceae gen. | 0.292006876 | 9.21E−06 |
| Lachnospiraceae gen. | 0.081503842 | 2.04E−06 |
| Coprococcus | 0.139659611 | 1.33E−06 |
| Ruminococcus (Lachno) | 0.04645315 | 6.55E−07 |
| Ruminococcus | 0.038383995 | 6.54E−07 |
| Turicibacter | 0.637961763 | ns |
| Lactobacillus | 5.145068807 | 1.37E−05 |
| Anaerostipes | 0.463344316 | 0.004148803 |
| Mucispirillum | 0.082908163 | 8.13E−07 |
| Adlercreutzia | 0.03927932 | 6.48E−07 |
| UC Ruminococcaceae | 0.133643617 | 0.006426379 |
| Roseburia | 0.144031142 | ns |
| Unclassified Bacteria | 0.171195652 | 2.21E−05 |
| Erysipelotrichaceae gen. | 1.188981043 | ns |
| Bilophila | 0.09375 | 5.48E−07 |
| Dehalobacterium | 0.205078125 | 1.37E−05 |
| Anaeroplasma | 0.61875 | ns |
| Ruminococcaceae gen. | 0.457417582 | 0.006426379 |
| Dorea | 0.090604027 | 1.91E−06 |
| Mogibacteriaceae gen. | 0.166666667 | 1.13E−05 |
| Clostridium | 0.1875 | 0.000131466 |
| Sutterella | 0.066964286 | 1.30E−06 |
| Coprobacillus | 1.125 | ns |
| UC Erysipelotrichaceae | 6 | 0.013299629 |
| Prevotellaceae gen. | 0.625 | ns |
| SFB | 12.375 | 0.000803781 |

Figures 2A, 2B, 2C:
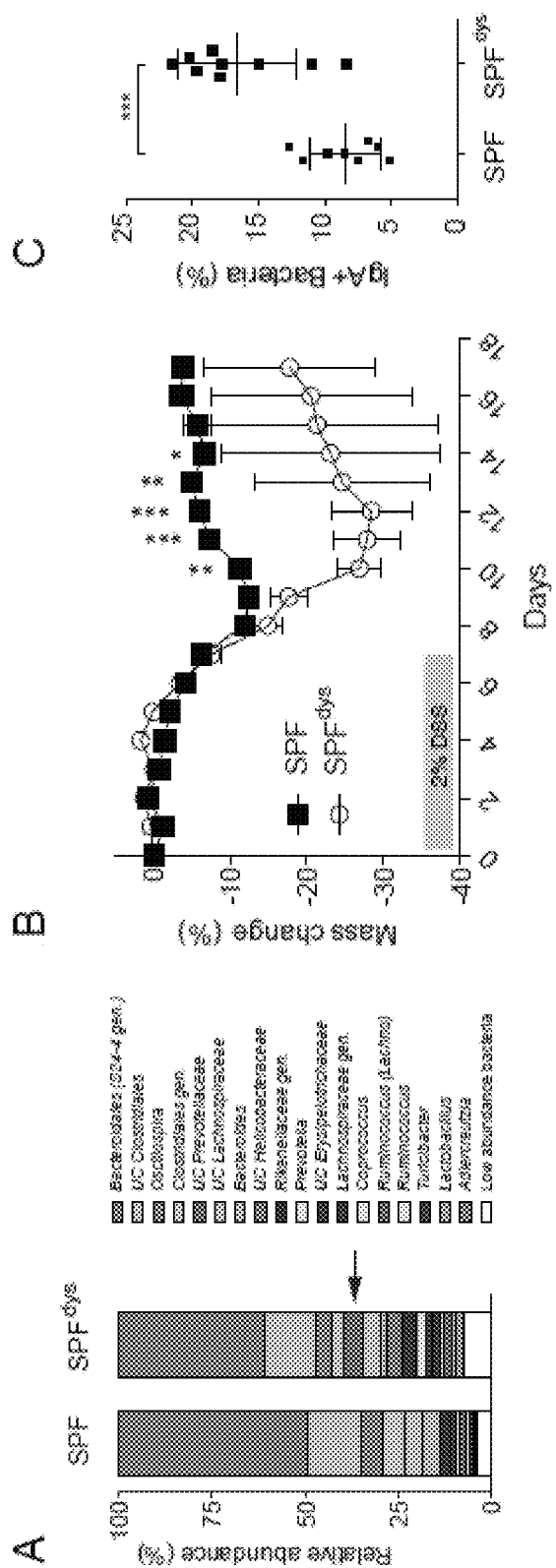
FIGS. 2A-2E, depicts the results of experiments demonstrating that IgA coating identifies colitogenic bacteria in mice with inflammasome-mediated intestinal dysbiosis (SPF$^{dys}$).
Figures 2D, 2E:
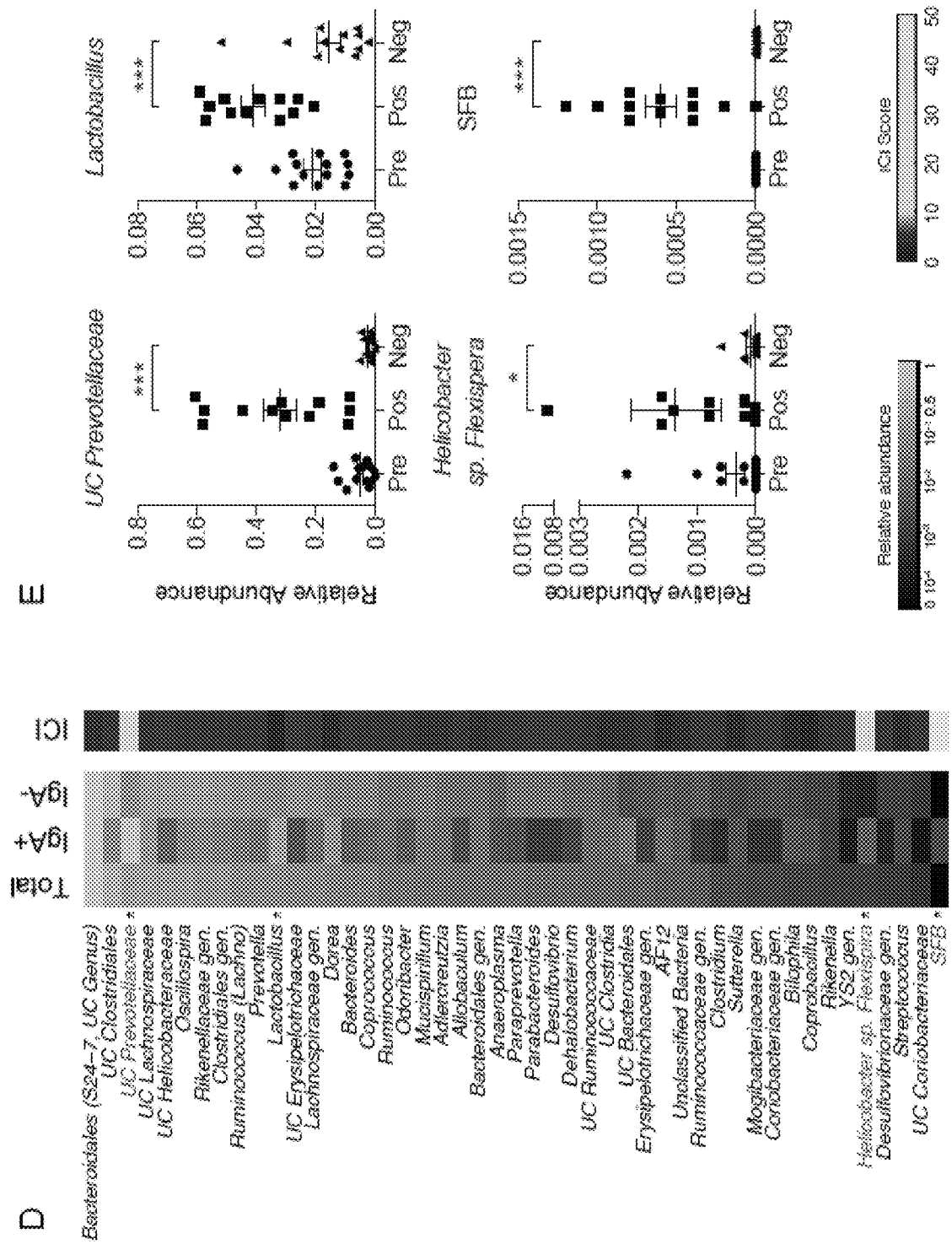

Colitogenic Members of the Intestinal Microbiota are Highly Coated with IgA in Mice with Inflammasome-Mediated Intestinal Dysbiosis Next tested was whether IgA coating would identify disease-driving members of the intestinal microbiota in the context of a colitogenic intestinal dysbiosis. It was recently found that mice lacking components of the inflammasome, which is a critical mediator of innate immunity, harbor a colitogenic intestinal microbiota that can be transmitted to wild type SPF mice through co-housing. In this model, susceptibility to colitis is driven by *Prevotellaceae* species (Elinav et al., 2011, Cell 145:745-757). Therefore, IgA-SEQ was performed on SPF mice that had acquired inflammasome-mediated intestinal dysbiosis through co-housing with Asc$^{-/-}$ mice (SPF$^{dys}$). As previously reported, co-housing with Asc$^{-/-}$ mice altered the composition of the SPF intestinal microbiota and strongly increased susceptibility to chemically-induced colitis (FIG. 2A, FIG. 2B and FIG. 7A). Flow cytometric analysis of IgA coating of the intestinal microbiota of SPF$^{dys}$ mice at the steady state revealed an increase in the percentage of intestinal bacteria coated with IgA as compared to SPF mice, which is consistent with the explanation that acquisition of the colitogenic microbiota altered the pattern and/or extent of IgA coating (FIG. 2C). Indeed, IgA+ bacteria in SPF$^{dys}$ mice were distinct from IgA− bacteria and from IgA+ bacteria in control SPF mice sampled under identical conditions (FIG. 7A; P<0.05, PERMANOVA). Although 23 taxa in SPF$^{dys}$ mice showed significant expansion as a result of co-housing, only two of these taxa were highly coated with IgA (Table 2, FIG. 2D, FIG. 2E and FIG. 7B; P<0.05 LEfSe); remarkably, the most abundant highly IgA coated taxon was an unclassified genus from the *Prevotellaceae* family, which is the defining taxon in inflammasome-mediated intestinal dysbiosis and the main driver of colitis in this model (Elinav et al., 2011, Cell 145:745-757). Furthermore, *Helicobacter* sp. *flexispira*, which is also acquired during co-housing, was highly coated with IgA in SPF$^{dys}$ mice. As in SPF mice, *Lactobacillus* remained coated and SFB remained highly coated in SPF$^{dys}$ mice.

TABLE 2

| Taxa | SPF (Mean Abundance) | SPF-Dys (Mean Abundance) | P value |
|---|---|---|---|
| UC Bacteroidales | 0 | 0.002514286 | 2.33E-07 |
| *Odoribacter* | 0 | 0.007171429 | 2.35E-07 |
| *Parabacteroides* | 0 | 0.003742857 | 2.35E-07 |
| Bacteroidales gen. | 0 | 0.004457143 | 2.35E-07 |
| *Paraprevotella* | 0 | 0.003885714 | 2.37E-07 |
| *Prevotella* | 0 | 0.0218 | 2.37E-07 |
| *Desulfovibrio* | 0 | 0.0034 | 2.37E-07 |
| UC Helicobacteraceae | 0 | 0.044285714 | 2.37E-07 |
| AF12 | 1.17647E-05 | 0.001628571 | 5.51E-07 |
| UC Prevotellaceae | 5.88235E-05 | 0.051957143 | 9.14E-07 |
| UC Clostridia | 0 | 0.001828571 | 1.00E-06 |
| *Rikenella* | 0 | 0.000371429 | 1.34E-05 |
| *Dorea* | 0.000988235 | 0.005414286 | 2.26E-05 |
| *Allobaculum* | 1.17647E-05 | 0.004542857 | 3.14E-05 |
| UC Erysipelotrichaceae | 5.88235E-05 | 0.018457143 | 3.58E-05 |
| *Streptococcus* | 0 | 0.000257143 | 4.59E-05 |
| Desulfovibrionaceae gen. | 0 | 0.000271429 | 0.000144935 |
| *Lactobacillus* | 0.007670588 | 0.021142857 | 0.000379843 |
| YS2 gen | 0 | 0.000357143 | 0.000445906 |
| *Dehalobacterium* | 0.001717647 | 0.003114286 | 0.001100491 |
| Coriobacteriaceae gen. | 8.23529E-05 | 0.000528571 | 0.001875312 |
| *Helicobacter* sp. *flexispira* | 0 | 0.000342857 | 0.003324003 |
| *Ruminococcus* (Lachno) | 0.0124 | 0.021985714 | 0.006514397 |

Strikingly, all of the bacteria that were found to be highly coated in SPF$^{dys}$ mice (*Prevotellaceae, Helicobacter* and SFB) are known to drive intestinal inflammation and disease development in mouse models of colitis (Elinav et al., 2011, Cell 145:745-757; Kullberg et al., 1998, Infect Immun 66:5157-5166; Stepankova et al., 2007, Inflamm Bowel Dis 13:1202-1211). In addition, SFB is a potent driver of intestinal T helper 17 (Th17) cell responses in mice and has been shown to exacerbate development of arthritis (Ivanov et al., 2009, Cell 139:485-498; Wu et al., 2010, Immunity 32:815-827).

Antigen-specific binding of IgA to the intestinal microbiota can result from both high affinity, T cell-dependent responses and lower affinity, T cell-independent responses (Bemark et al., 2012, Ann NY Acad Sci 1247:97-116). In addition, IgA can bind members of the intestinal microbiota non-specifically, for example through glycan-dependent binding to certain Gram-positive bacteria (Mathias and Corthesy, 2011, Gut Microbes 2:287-293). Importantly, IgA coating of SFB, UC *Prevotellaceae*, and *Helicobacter* sp. *flexispira* was found to be significantly reduced in SPF$^{dys}$ mice lacking T cells, which shows that high IgA coating detected via IgA-SEQ is largely the result of high-affinity, antigen-specific, T cell-dependent antibody responses rather than low-affinity T cell-independent responses (FIG. 7C). In contrast, coating of *Lactobacillus*, which was significantly but not highly coated (ICI<10), was increased in T cell-deficient mice, demonstrating that these IgA antibodies resulted from either T cell-independent immune responses or non-specific binding.

IgA-SEQ Identifies Highly Coated Members of the Intestinal Microbiota in IBD Patients Interactions between the intestinal microbiota and the immune system play a critical role in IBD development and progression in humans; however, the specific bacteria responsible for these effects have remained elusive (Abraham and Cho, 2009, New Engl J Med 361: 2066-2078; Knights et al., 2013, Gut 62:1505-1510; Round and Mazmanian, 2009, Nat Rev Immunol 9:313-323). Since the data show that IgA coating can identify colitogenic members of the intestinal microbiota in mice, coating of fecal bacteria from 27 patients with Crohn's disease (CD), 8 patients with ulcerative colitis (UC) and 20 healthy controls was next examined to identify such organisms in human disease. Similar to mice with intestinal dysbiosis, and as previously reported (van der Waaij et al., 2004, Eur J Gastroen Hepat 16:669-674), the proportion of intestinal bacteria that are coated with IgA was significantly increased in CD and UC patients as compared to healthy controls (FIG. 3A and FIG. 6D). As expected, both healthy control subjects and IBD patients exhibited considerable diversity in their gut microbiota compositions and patterns of IgA coating (FIG. 8). Individual ICI scores for bacteria in each subject can be found in Table S3 of Palm et al. (Palm et al., 2014, Cell, 158(5): 1000-1010) and in Table 3 of U.S. Provisional Patent Application No. 62/042,878, each of which is herein incorporated by reference. While many species were highly coated (ICI>10) in both IBD and control groups, 35 species were uniquely highly coated in patients with IBD (FIG. 3B and FIG. 3C). For example, *Streptococcus luteciae, Haemophilus parainfluenzae*, and *Collinsella aerofaciens* were detected in both IBD patients and some healthy controls, but were only highly coated in IBD. In addition, multiple species that were uniquely present in IBD were highly coated in at least one patient (e.g., unclassified *Bulleidia, Allobaculum* spp., *Lactobacillus mucosae*, unclassified *Pediococcus*, and *Weissella* spp.). Finally, both CD- and UC-specific highly IgA coated bacterial species could be observed; for instance, unclassified *Clostridiales*, unclassified *Ruminococcaceae*, and *Blautia* spp. were uniquely coated in CD, and *Eubacterium dolichum* and *Eggerthella lenta* were uniquely coated in UC.

Figure 4A:
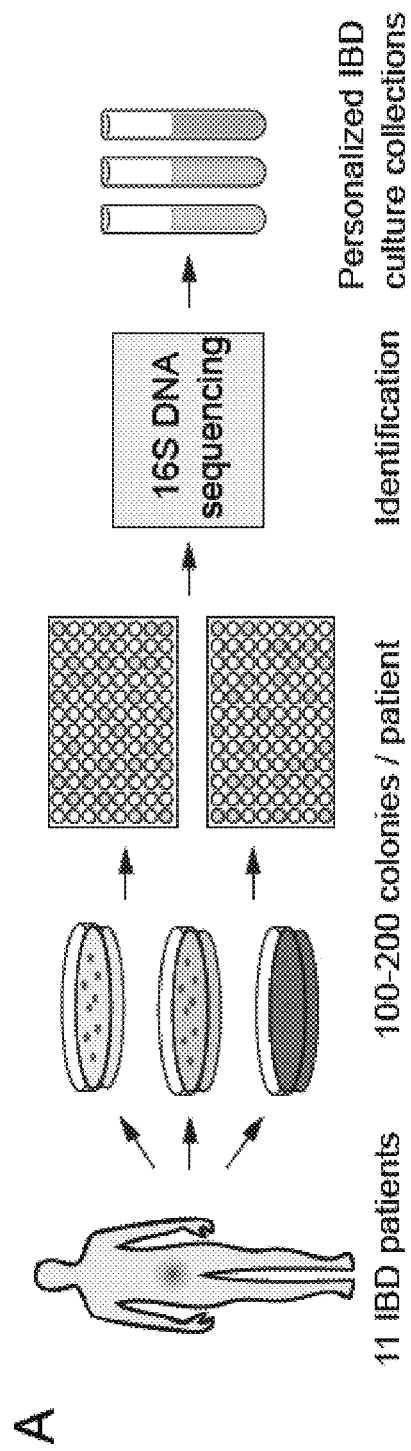
FIGS. 4A-4E, depicts the results of experiments demonstrating the isolation of personalized IBD-associated gut microbiota culture collections, assembly of IgA+ and IgA− consortia and colonization of germ-free mice.

Establishment of a Gnotobiotic Mouse Model to Evaluate the Effects of IgA+ and IgA− Members of the Human Microbiota on Intestinal Inflammation In order to directly test whether IgA coating marks human intestinal bacteria that preferentially drive intestinal inflammation, isolation of representative IgA coated and non-coated bacteria from human IBD patients was attempted. Personalized gut microbiota culture collections were assembled from eleven IBD patients using standard anaerobic culture media and a custom rich medium designed to recover intestinal bacterial species from humans (Goodman et al., 2011, P Natl Acad Sci USA 108:6252-6257). First, 100-200 single colonies were selected and cultured per patient sample, and these isolates were taxonomically classified through high-throughput 16S sequencing (FIG. 4A). The individual bacterial isolates in each of the personalized gut microbiota culture collections were then cross-referenced with the matching data from the IgA-SEQ studies to classify all isolates based on their level of IgA coating. Finally, individual isolates from these culture collections were rationally selected and combined to assemble representative consortia consisting of either isolates that were classified as highly coated (IgA+ consortium) or isolates that were classified as low coated (IgA− consortium) (FIG. 4B; see methods for criteria used to select the IgA+ and IgA− consortia). Importantly, the taxa comprising the IgA+ and IgA− consortia would not have been chosen simply based on traditional evaluations of the relative abundance of these taxa in healthy versus sick individuals (FIG. 9).

Figures 4B, 4C:
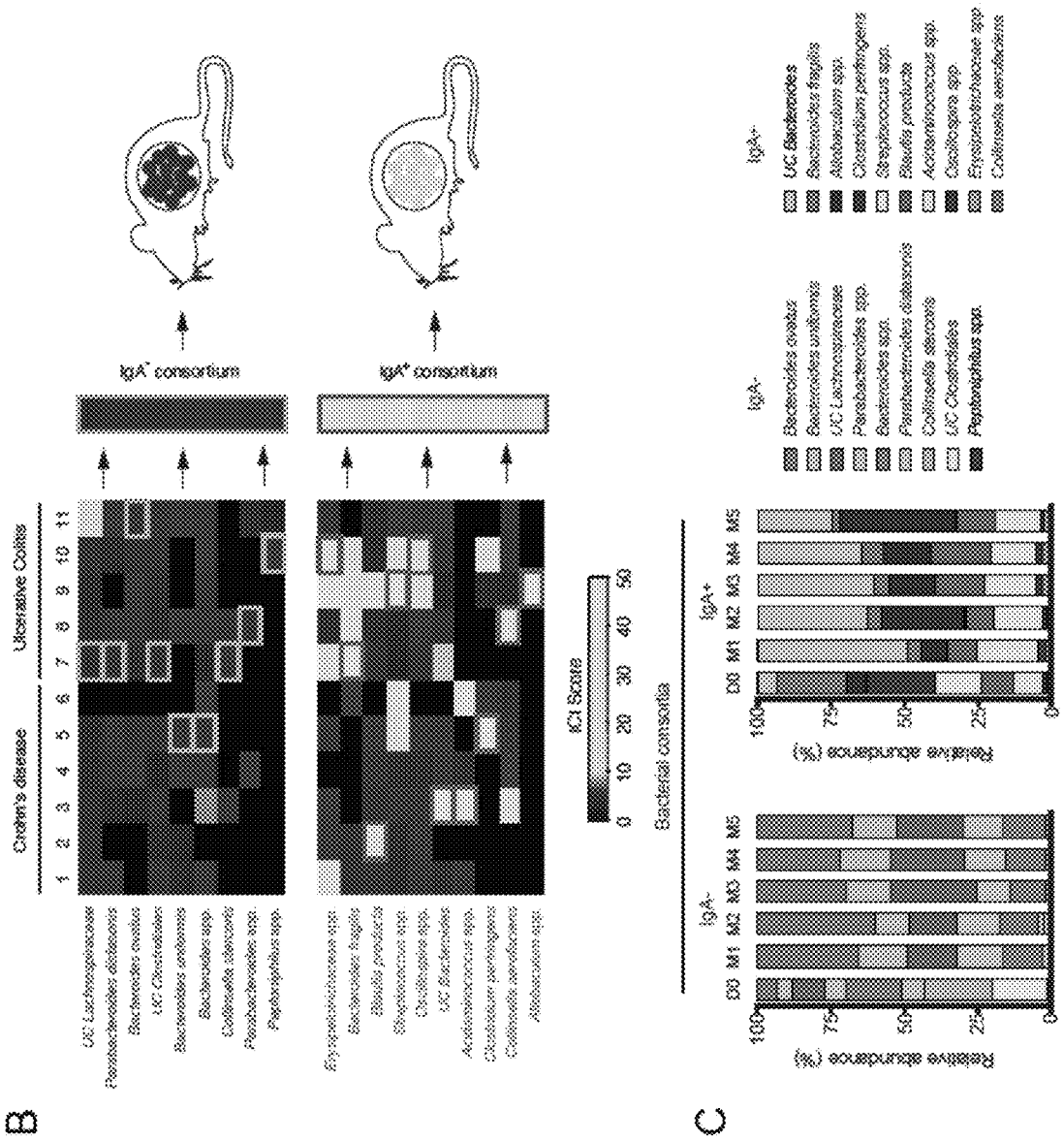

To directly test the effects of IgA+ versus IgA− bacteria from IBD patients on intestinal inflammation, germ-free mice were colonized with the assembled IgA+ or IgA− consortia. As a first test of the feasibility of this system, the composition of the intestinal microbiota in these mice was examined two weeks post-colonization and it was found that all but two bacteria, one from each consortium, were able to successfully colonize germ-free mice (FIG. 4C).

Figures 4D, 4E:
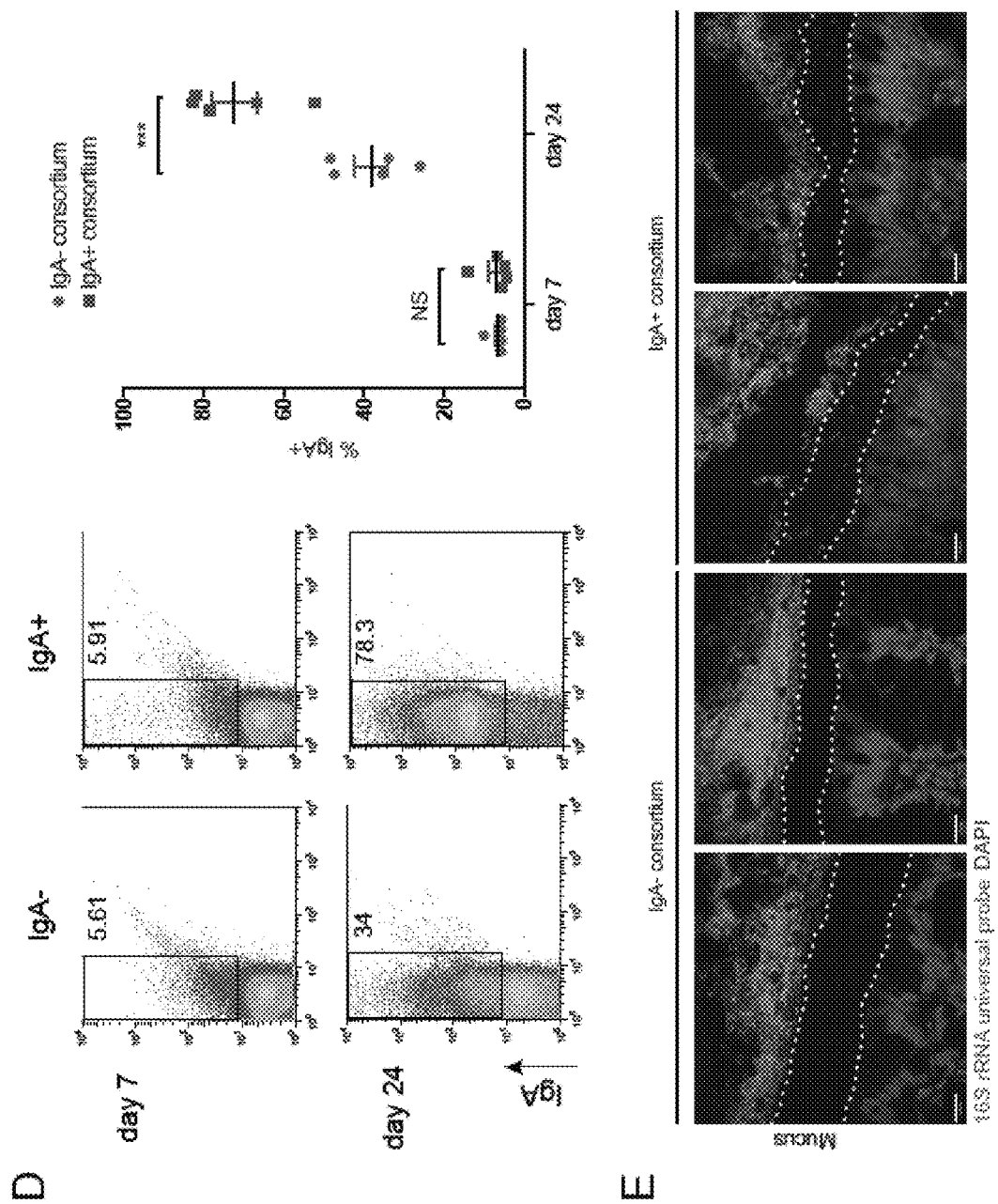

Next was tested whether the human IgA+ consortium would also preferentially induce the production of IgA when transplanted into germ-free mice. At seven days post-colonization, before the induction of a specific IgA response, fecal bacteria from mice colonized with the IgA+ or IgA− consortia was found to show equivalent low levels of IgA coating by flow cytometry (FIG. 4D). However, as compared to the IgA− consortium, the IgA+ consortium showed dramatically higher levels of IgA coating by day 24 post-colonization, which demonstrates that the IgA+ consortium had induced a strong and specific IgA response. These data show that bacteria that preferentially drive IgA responses in human IBD patients can also drive strong IgA responses in gnotobiotic mice.

The bacteria that were identified as highly coated in SPF$^{dys}$ mice are known to colonize normally sterile mucosal environments, such as the inner mucus layer and intestinal crypts (Elinav et al., 2011, Cell 145:745-757; Ivanov et al., 2009, Cell 139:485-498). To test whether the bacteria in the human IgA+ consortium also exhibit such characteristics, bacterial 16S rRNA fluorescence in situ hybridization (FISH) was performed on colons from IgA+ and IgA− consortia colonized mice. Remarkably, the presence of many bacteria was observed in the mucus layer of mice colonized with the IgA+ consortium (FIG. 4E). In contrast, in mice colonized with the IgA− consortium, the inner mucus layer remained devoid of any detectable bacteria. Thus, one mechanism by which the bacteria comprising the IgA+ consortium may selectively induce IgA responses is through the invasion or colonization of normally sterile mucosal environments.

Figures 5A, 5B, 5C, 5D:
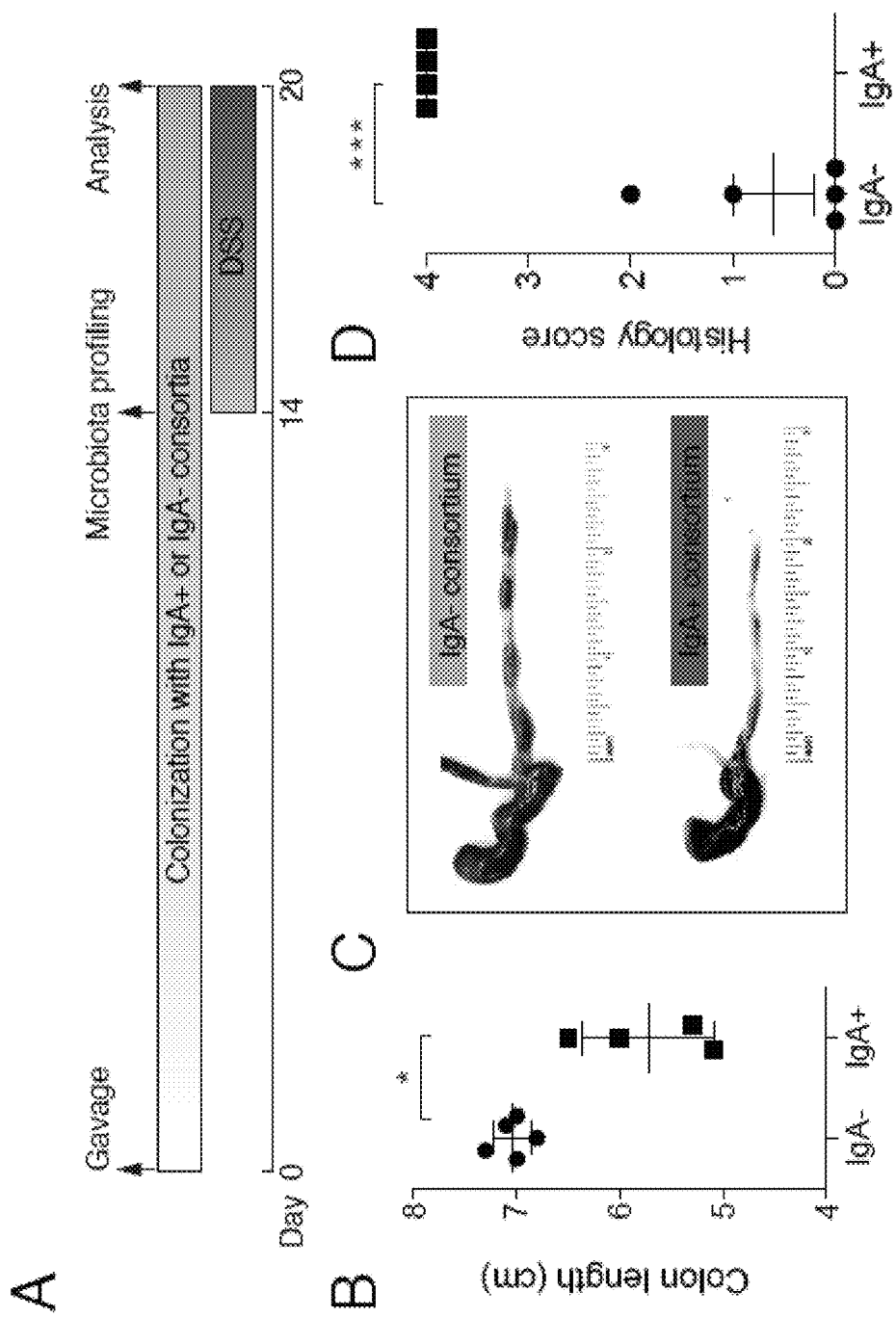
FIGS. 5A-5E, depicts the results of experiments demonstrating that IBD-associated IgA+ bacteria exacerbate DSS-induced colitis in gnotobiotic mice.
Figure 5E:
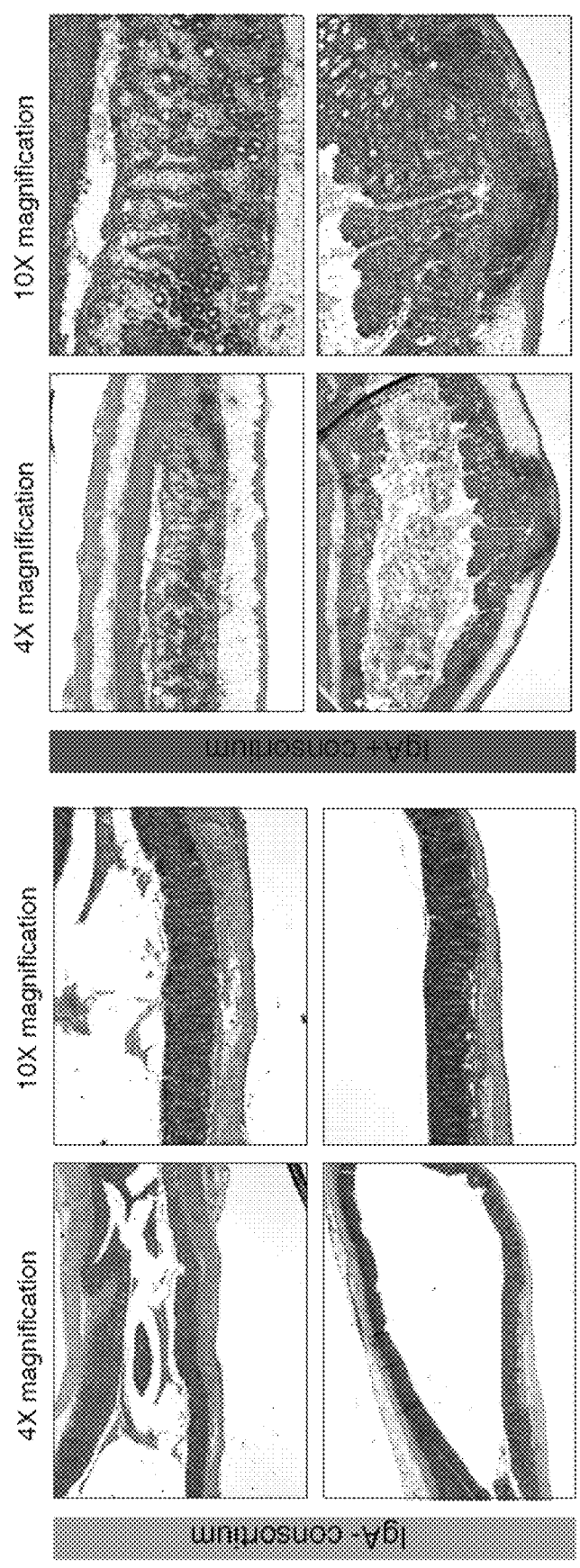

IgA Inducing Members of the Intestinal Microbiota Cultured from IBD Patients Exacerbate DSS Colitis in Gnotobiotic Mice Germ-free mice colonized with the IgA− and IgA+ consortia for two weeks showed no signs of spontaneous intestinal pathology, which is consistent with the explanation that these bacterial strains are not immediately pathogenic in wild-type mice under healthy conditions. However, after the induction of colitis with DSS, IgA+ mice exhibited obvious and severe intestinal inflammation with extensive bleeding throughout the intestine, as well as significant shortening of the colon, while the intestines of IgA− mice appeared normal (FIG. 5A-FIG. 5C). Histological examination revealed that IgA+ mice showed significant cellular infiltration and extensive loss of tissue integrity in the colon, while IgA− mice showed minimal visible inflammation (FIG. 5D and FIG. 5E). These data show that bacteria isolated from IBD patients and chosen based on high IgA coating selectively drive severe intestinal inflammation in a mouse model of IBD.

Bacterial isolates from different patients that were taxonomically assigned as the same species via 16S sequencing often showed differential IgA coating. While many factors may contribute to this phenomenon, the observation was consistent with the explanation that these isolates represent distinct bacterial strains of the same species that display divergent behaviors that lead to differential IgA induction. As a proof-of-principle test of this scenario, two isolates of *B. fragilis* from the gut microbiota culture collections were identified and characterized and showed either high (ICI=37.8) or low (ICI=0.68) IgA coating (FIG. 10F). Whole genome sequencing demonstrated that these isolates represent genetically distinct strains of the same species (i.e., *B. fragilis*) (FIG. 10G). Finally, germ-free mice were mono-colonized with these two strains and their effects on the development of DSS-induced colitis were examined. Mice colonized with the IgA+ strain of *B. fragilis* were found to exhibit more severe colitis than the mice colonized with the IgA− strain of *B. fragilis*, as measured by colon length and histopathology (FIG. 10H-FIG. 10J). These data demonstrate that different strains of the same bacterial species exhibit differential effects on the intestinal immune system and inflammatory disease and that they can be distinguished based on IgA coating.

IRA Coating of Intestinal Microbiota

Taxa-specific coating of the intestinal microbiota with the secreted immunoglobulin IgA was examined based on the hypothesis that levels of IgA coating might distinguish between members of the microbiota that impact disease susceptibility and/or severity by stimulating inflammatory responses and the remaining members of the microbiota. High coating with IgA was found to specifically mark a select group of known inflammation- and disease-driving intestinal bacteria in mice with inflammasome-mediated colitogenic dysbiosis. Bacteria isolated from patients with IBD and selected based on high IgA coating was found to induce potent IgA responses and dramatically exacerbate development of DSS-induced colitis in gnotobiotic mice. Thus, the data demonstrate that high coating with IgA selectively marks inflammatory, and therefore, potentially disease-driving commensals in mice and humans.

Bacterial cell-sorting based on IgA coating and 16S rRNA gene sequencing were combined in order to examine the intestinal immune response to the intestinal microbiota in an unbiased and comprehensive manner. Recently, FACS-based bacterial cell sorting has been combined with next-generation sequencing by others as a way to examine: the active human gut microbiota (Peris-Bondia et al., 2011, PLoS One 6:e22448); responses of the intestinal microbiota to xenobiotics (Maurice et al., 2013, Cell 152:39-50); the effect of IgA coating on bacterial gene expression (Cullender et al., 2013, Cell Host Microbe 14:571-581); and IgA coating of the healthy intestinal microbiota (D'Auria et al., 2013, Sci Rep 3:3515). This type of approach, which combines taxonomic information with functional information regarding bacterial viability, behavior, or other bacterial features, will likely become increasingly common in future studies of the microbiota and its interactions with the host. The data clearly illustrate the utility of this approach as a way to functionally classify intestinal bacteria based on their interactions with and recognition by the host immune system.

To maintain intestinal homeostasis, the mucosal immune system must selectively recognize and respond to pathogenic species while simultaneously maintaining tolerance to harmless and symbiotic members of the intestinal microbiota (Belkaid and Hand, 2014, Cell 157:121-141). Because most innate immune receptors involved in the detection of bacterial pathogens sense microbial components present in both pathogens and commensals (e.g., lipopolysaccharide), the mechanisms by which the immune system distinguishes between pathogens and commensals remain largely unknown. However, one way the immune system is thought to distinguish between pathogens and commensals is by sensing pathogen-associated activities or behaviors, such as adherence to the intestinal epithelium, tissue invasion or destruction, or the ability to colonize normally sterile mucosal environments, such as intestinal crypts (Sansonetti, 2011, Mucosal Immunol 4:8-14). The inflammatory commensals that were identified via IgA-SEQ appear to exhibit similar activities or behaviors. For example, *Prevotellaceae* species invade the mucus layer in the large intestine and colonize colonic crypts (Elinav et al., 2011, Cell 145:745-757); furthermore, SFB firmly adhere to the epithelium in the small intestine (Ivanov et al., 2009, Cell 139:485-498). Finally, members of the human IgA+ consortium were found to be observed in the colonic mucus layer. Since the invasion of normally sterile sites proximal to the epithelium would naturally lead to increased stimulation of the innate immune system and increased availability of antigen for the induction of specific T cell and antibody responses, these behaviors may at least partially explain the propensity of IgA coated bacteria to preferentially induce both IgA responses and the inflammatory responses that lead to exacerbated disease susceptibility.

A variety of specific innate and adaptive immune mechanisms are known to influence IgA responses to the intestinal microbiota. For example, the Toll-like receptors have been implicated both T-dependent and T-independent IgA responses to the gut microbiota (Tezuka et al., 2007, Nature 448:929-933). Furthermore, specific T cell subsets, including T helper type 17 cells and regulatory T cells, as well as gamma-delta T cells have been implicated in coordinating IgA responses (Cong et al., 2009, P Natl Acad Sci USA 106:19256-19261; Fujihashi et al., 1996, J Exp Med 183:1929-1935; Hirota et al., 2013, Nat Immunol 14:372-379; Kawamoto et al., 2012, Science 336:485-489). The specific responses observed by IgA-SEQ were largely T-dependent; however, T-independent responses also clearly contributed to IgA responses to specific taxa.

Since highly IgA coated bacteria are constitutive inhabitants of the intestine and can drive disease, it appears that the host's IgA response to these bacteria is insufficient to lead to bacterial clearance or complete neutralization. Nonetheless, the IgA response may still reduce the level of inflammation caused by such bacteria. Indeed, SFB expand in the absence of an effective IgA response (Kato et al., 2014, Immunol Cell Biol 92:49-56; Shinkura et al., 2004, Nat Immunol 5:707-712). Furthermore, bacterial-specific IgA has been shown to minimize intestinal inflammation through bacterial exclusion (Peterson et al., 2007, Cell Host Microbe 2:328-339). IgA inducing bacteria may drive even stronger pathological inflammatory responses in mice that are unable to mount an efficient IgA response.

The etiology of IBD involves a combination of genetic, environmental and microbial factors (Abraham and Cho, 2009, New Engl J Med 361: 2066-2078; Knights et al., 2013, Gut 62:1505-1510). Here, the microbial contribution to IBD was focused upon and attempts were made to identify members of the human gut microbiota that may preferentially impact IBD susceptibility and/or severity. One reason why it has been difficult to identify disease-driving bacteria in humans is that the strategies traditionally used to identify these bacteria in mice, including co-housing and gut microbiota transfer cannot be applied to humans (Dantas et al., 2013, Annu Rev Microbiol 67:459-475). In addition, due to the diversity of the intestinal microbiota in humans, the specific bacteria that drive disease may differ dramatically from patient to patient and, therefore, identifying these bacteria may require an individualized, rather than population-based, approach (Huttenhower and Consortium, 2012, Nature 486:207-214; Lozupone et al., 2012, Nature 489: 220-230). High IgA coating was found to be able to identify colitogenic bacteria from patients with IBD by combining: (i) a functional classification of the intestinal microbiota based on the host's individual immune response; (ii) anaerobic culturing of members of the intestinal microbiota from diseased patients; and (iii) colonization of germ-free mice with human microbial consortia selected rationally based on their propensity to induce inflammation and, therefore, become highly coated with IgA. Using this approach, a subset of the intestinal microbiota from IBD patients that is characterized by high coating with IgA was shown to selectively confer susceptibility to colitis in a mouse model of IBD. Thus, the data demonstrate that the host's individual IgA response to the intestinal microbiota can be used as a guide to identify members of the microbiota that preferentially impact disease susceptibility and/or severity. The ability to identify these important bacterial taxa in humans in an individualized manner represents a first step towards the development of personalized, microbiota-focused therapies that may reduce, reverse, or even prevent disease development through targeted elimination or replacement of disease-driving members of the intestinal microbiota.

IgA+ Bacteria from Healthy Humans, Unlike IgA+ Bacteria from Humans with IBD, are Non-Colitogenic As described above, it is shown herein that IgA coating marks colitogenic bacteria in patients with IBD. However it was found that healthy humans also harbored similar numbers of highly IgA coated bacteria. The fact that these bacteria induce high levels of specific IgA suggests that they intimately interact with the intestinal immune system, but clearly are not driving pathological intestinal inflammation since their human hosts remain healthy. Two major possibilities may explain this observation: 1) the IgA− coated bacteria in healthy humans and IBD patients are equally capable of driving intestinal inflammation but host genetics or environmental factors dictate whether disease will actually occur; or, 2) the IgA-coated bacteria in healthy humans are fundamentally different from those found in patients with IBD.

To directly test whether IgA+ bacteria from healthy humans have similar or different effects as compared to IgA+ bacteria from IBD patents, five bacterial strains, cultured from healthy subjects, were selected that were highly coated with IgA as based on IgA-SEQ analysis (ICI score >10) in the healthy subject from whom they were isolated. These healthy IgA+ strains were next assembled into a representative bacterial consortium. As an initial test of whether IgA+ bacteria from healthy humans are inflammatory or immunoregulatory, germ-free mice were colonized with either the 'IgA+ (healthy)' consortium, the colitogenic 'IgA+ (IBD)' consortium, or the non-colitogenic 'IgA−' consortium. Colitis was then induced by administration of 2.5% DSS in the water. As described previously, the 'IgA+ (IBD)' consortium induced severe colitis, as measured by colon shortening at day 6, while the 'IgA−' consortium did not induce significant colitis. However, unlike the 'IgA+ (IBD)' consortium, the 'IgA+ (healthy)' consortium appeared to result in mild protection from colitis as compared to the 'IgA−' consortium (FIG. 11). These results suggest that 'IgA+' bacteria from healthy individuals are qualitatively different from 'IgA+' bacteria in IBD and may induce immunoregulatory responses that are associated with a healthy intestine.

IgA+ Bacteria from Healthy Humans can Protect Against Bacterial-Driven Colitis

The finding that 'IgA+' bacteria from healthy individuals are non-colitogenic raises the possibility that these bacteria may be able to protect against colitis. Therefore, it was next tested whether IgA+ bacteria from healthy humans could reduce or neutralize the pathogenic effects of colitogenic IgA+ bacteria from IBD patients. Germ-free mice were colonized with either the non-colitogenic 'IgA−' consortium, the colitogenic 'IgA+ (IBD)' consortium, or a mixture of the colitogenic 'IgA+ (IBD)' consortium and the 'IgA+ (healthy)' consortium. One week after colonization, colitis was induced by administration of 2% DSS ad libitum in the drinking water. As described previously, the 'IgA+ (IBD)' consortium induced severe colitis, as measured by colon shortening at day 6, while the 'IgA−' consortium induced only mild colitis. However, the 'IgA+ (healthy)' consortium blocked the colitogenic effects of the 'IgA+ (IBD)' consortium completely (FIG. 12). These results suggest that 'IgA+' bacteria from healthy individuals can protect against colitis driven by bacteria found in IBD patients and show that IgA-SEQ can be used to identify protective bacteria in healthy individuals.

Oral Immunization can Protect Against Colitis Driven by Bacteria Found in IBD Patients It was found that specific individual IgA-inducing members of the gut microbiota isolated from patients with IBD were potently colitogenic when transferred into germ-free mice. For instance, mice colonized with the non-colitogenic 'IgA−' community did not show significant signs of colitis when treated with 2% DSS for 6 days, while the 'IgA−' community together with the IBD-associated IgA-inducing bacterium *Erysipelotrichaceae* spp. led to potent intestinal inflammation. The observation that the presence of one individual inflammatory IgA+ bacterial species can transform a 'neutral' microbiota into a dysbiotic, inflammatory microbiota suggests that neutralizing or removing this inflammatory bacterial species from the microbiota should ameliorate colitis. To test this possibility, groups of germ-free mice were colonized with the 'IgA−' community together with *Erysipelotrichaceae* spp. ('IgA− plus Ery') for one week to mimic the microbiota of IBD patients containing an individual inflammatory bacterial species amongst a majority of neutral bacterial species. Next, these mice were orally immunized with heat-killed *Erysipelotrichaceae* spp. with cholera toxin (CT) as an adjuvant. Using such low levels of CT as an adjuvant does not result in intestinal inflammation due to the toxin but rather induces a highly potent secretory IgA response to the heat-killed bacteria with which it is co-administered. After weekly immunizations for 6 weeks, these mice, along with control mice that were either non-immunized or mock-immunized with CT alone, were treated with 1.8% DSS to induce colitis. Interestingly, while non-immunized and mock-immunized mice showed severe inflammation, as demonstrated by shortening of the colon, mice immunized with heat-killed *Erysipelotrichaceae* spp. showed significant protection from intestinal pathology (FIG. 13). These results demonstrate that targeting one or more inflammatory IgA+ bacterial species through vaccination can ameliorate inflammatory responses in the intestine, and suggest that targeting similar species in IBD patients may be a feasible approach to treat or cure their disease.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating inflammatory bowel disease (IBD) in a subject, the method comprising administering to the subject non-colitogenic bacteria, wherein the non-colitogenic bacteria do not contribute to the development or progression of IBD in the subject, and wherein the subject has been diagnosed with IBD via detection of secretory antibody-bound colitogenic bacteria that do contribute to the development or progression of IBD.

2. The method of claim 1, further comprising the step of administering to the subject at least one therapy to diminish the number of at least one strain of at least one species of bacteria that is associated with the development or progression of the IBD.

3. The method of claim 1, wherein the non-colitogenic bacteria are administered in a dosage range selected from about $10^4$ to about $10^6$ CFU per administration or about $10^6$ to about $10^{10}$ CFU per administration.

4. The method of claim 1, wherein the non-colitogenic bacteria are identified from a healthy subject that does not have IBD.

5. The method of claim 1, wherein the non-colitogenic bacteria are administered as live bacteria.

6. The method of claim 1, wherein the non-colitogenic bacteria are administered in a buffering agent selected from sodium bicarbonate, milk, yogurt, infant formula, and other dairy products.

7. The method of claim 1, wherein the non-colitogenic bacteria are mixed with a carrier and applied to a liquid or to food for administration.

8. The method of claim 1, wherein the non-colitogenic bacteria are secretory antibody-bound and are derived from a subject who does not suffer from IBD.

9. The method of claim 1, wherein the non-colitogenic and/or colitogenic bacteria are selected from the group consisting of *Akkermansia muciniphila, Bacteroides acidifaciens, Bacteroides coprophilus, Bacteroides fragilis, Bacteroides ovatus, Bacteroides uniformis, Bifidobacterium adolescentis, Blautia obeum, Blautia producta, Clostridium perfringens, Collinsella aerofaciens, Collinsella stercoris, Coprococcus catus, Dorea formicigenerans, Eggerthella lenta, Eubacterium biforme, Eubacterium dolichum, Faecalibacterium prausnitzii, Haemophilus parainfluenzae, Lactobacillus reuteri, Lactobacillus mucosae, Lactobacillus zeae, Mitsuokella multacida, Parabacteroides distasonis, Peptostreptococcus anaerobius, Prevotella copri, Prevotella stercorea, Roseburia faecis, Ruminococcus bromii, Ruminococcus gnavus, Ruminococcus torques, Streptococcus anginosus, Streptococcus luteciae, Sutterella, Turicibacter, Veillonella parvula*, and *Veillonella dispar*.

10. The method of claim 9, wherein the non-colitogenic and/or colitogenic bacteria is *Bacteroides fragilis*.

11. The method of claim 1, further comprising administering to the subject at least one therapy to diminish the number or pathogenic effects of the colitogenic bacteria present in the subject.

12. The method of claim 11, wherein the at least one therapy is selected from the group consisting of a vaccine, an antibiotic, and a passive immunotherapy.

13. The method of claim 12, wherein the at least one therapy is a vaccine.

14. The method of claim 12, wherein the at least one therapy is a passive immunotherapy.

* * * * *